(12) United States Patent
Prabhakar et al.

(10) Patent No.: US 7,910,723 B2
(45) Date of Patent: Mar. 22, 2011

(54) IG20 SPLICE VARIANTS THERAPEUTICS FOR CANCER

(75) Inventors: Bellur S. Prabhakar, Oakbrook, IL (US); Nirupama Mulherkar, Bronx, NY (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/174,296

(22) Filed: Jul. 16, 2008

(65) Prior Publication Data

US 2009/0075929 A1  Mar. 19, 2009

Related U.S. Application Data

(63) Continuation-in-part of application No. PCT/US2007/060712, filed on Jan. 18, 2007.

(60) Provisional application No. 60/760,321, filed on Jan. 19, 2006.

(51) Int. Cl.
*C07H 21/04* (2006.01)
(52) U.S. Cl. .................. 536/24.5; 536/24.31; 536/24.1; 435/6; 435/325; 435/375; 514/44
(58) Field of Classification Search .................... None
See application file for complete search history.

(56) References Cited

U.S. PATENT DOCUMENTS

| 2003/0162734 A1* | 8/2003 | Miller et al. ............... 514/44 |
| 2007/0031844 A1* | 2/2007 | Khvorova et al. ............ 435/6 |
| 2008/0233645 A1 | 9/2008 | Prabhakar |

FOREIGN PATENT DOCUMENTS

| WO | WO 2005/037303 A1 | 4/2005 |
| WO | WO 2007/084954 A2 | 7/2007 |

OTHER PUBLICATIONS

Thompson et al. Applications of antisense and siRNAs during preclinical drug development. DDT Vo. 7, No. 17, 2002.*
Efimova et al., "Differential Effects of IG20 and Its Splice Isoform, DENN-SV, on Cell Proliferation and Apoptosis," *FASEB Jrnl.*, 16:5 A1083 (2002).
Hilger et al., "The Ras-Raf-MEK-ERK Pathway in the Treatment of Cancer," *Onkologie*, 25 (6), 511-518 (2002).
International Search Report issued in PCT/US2004/030986 (2005).
Al-Zoubi et al., "Contrasting Effects of IG20 and Its Splice Isoforms, MADD and DENN-SV, on Tumor Necrosis Factor alpha-induced Apoptosis and Activation of Caspase-8 and -3," *The Journal of Biological Chemistry*, 276 (50): 47202-47211 (2001).
Antignani et al., "How do Bax and Bak lead to permeabilization of the outer mitochondrial membrane?," *Current Opinion in Cell Biology*, 18: 685-689 (2006).
Barber et al., "Membrane Translocation of P-Rex1 is Mediated by G Protein Betagamma Subunits and Phosphoinositide 3-Kinase," *The Journal of Biological Chemistry*, 282 (41): 29967-29976 (2007).

Bhaskar et al., "The Two TORCS and Akt," *Developmental Cell*, 12: 487-502 (2007).
Brinkman et al., "Engagement of Tumor Necrosis Factor (TNF) Receptor 1 Leads to ATF-2-and p38 Mitogen-activated Protein Kinase-dependent TNF-alpha Gene Expression," *The Journal of Biological Chemistry*, 274 (43): 30882-30886 (1999).
Brown et al., "MADD is highly homologous to a Rab3 guanine-nucleotide exchange protein (Rab3-GEP)," *Curr. Biol.*, 8 (6): R191 (1998).
Brunet et al., "Akt Promotes Cell Survival by Phosphorylating and Inhibiting a Forkhead Transcription Factor," *Cell*, 96 (43): 857-868 (1999).
Chow et al., "DENN, a novel human gene differentially expressed in normal and neoplastic cells," *DNA Sequence—The Journal of Sequencing and Mapping*, 6: 263-273 (1996).
Chow et al., "The human DENN gene: genomic organization, alternative splicing, and localization to chromosome 11p. 11.21-p. 11.22," *Genome*, 41: 543-552 (1998).
Cuevas et al., "Role of mitogen-activated protein kinase kinase kinases in signal integration," *Oncogene*, 26: 3159-3171 (2007).
Datta et al., "Akt Phosphorylation of BAD Couples Survival Signals to the Cell-Intrinsic Death Machinery," *Cell*, 91: 231-241 (1997).
De Cesare et al., "Rsk-2 activity is necessary for epidermal growth factor-induced phosphorylation of CREB protein and transcription of c-fos gene," *Proc. Natl. Acad. Sci.*, 95: 12202-12207 (1998).
Del Villar et al., "Down Regulation of DENN/MADD, a TNF receptor binding protein, correlates with neuronal cell death in Alzheimer's disease brain and hippocampal neurons," *PNAS*, 101 (12): 4210-4215 (2004).
Dhillon et al., "MAP kinase signaling pathways in cancer," *Oncogene*, 26: 3279-3290 (2007).
Dohi et al., "Comparmentalized Phosphorylation of IAP by Protein Kinase A Regulates Cytoprotection," *Molecular Cell*, 27: 17-28 (2007).
Du et al., "Smac, a Mitochondrial Protein that Promotes Cytochrome c-Dependent Caspase Activation by Eliminating IAP Inhibition," *Cell*, 102: 33-42 (2000). Efimova et al., "IG20, a MADD Splice Variant, Increases Cell Susceptibility to gamma-Irradiation and Induces Soluble Mediators That Suppress Tumor Cell Growth," *Cancer Research*, 63: 8768-8776 (2003).
Efimova et al., "IG20, in contract to DENN-SV, (MADD Splice Variants) suppresses tumor cell survival, and enhances their susceptibility to apoptosis and cancer drugs," *Oncogene*, 23: 1076-1087 (2004).

(Continued)

*Primary Examiner* — Kimberly Chong
(74) *Attorney, Agent, or Firm* — Barnes & Thornburg LLP; Alice O. Martin

(57) ABSTRACT

Methods and compositions inhibit the growth of cancer cells by selectively down-regulating the expression of an IG20 splice variant including MADD. Specific knock-down of MADD splice variant resulted in the apoptosis of cancer cells. Interfering RNAs including small hairpin RNAs (shRNA) to down-regulate MADD expression in vivo are disclosed. Inhibition of MADD phosphorylation by Akt results in activation of cancer cell death. Down-regulation of MADD expression results in switching to apoptotic mode due to lack of MAPK activation upon TNF-α-based induction.

9 Claims, 25 Drawing Sheets

OTHER PUBLICATIONS

Garcia-Blanco et al., "Alternative splicing in disease and therapy," *Nature Biotechnology*, 22 (5): 535-546 (2004).

Gardai et al., "Phosphorylation of Bax Ser184 by Akt Regulates Its Activity and Apoptosis in Neutrophils," *The Journal of Biological Chemistry*, 279 (20): 21085-21095 (2004).

Goto et al., "A Novel Human Insulinoma-associated cDNA, IA-1, Encodes a Protein with "Zinc-finger" DNA-binding Motifs," *The Journal of Biological Chemistry*, 267 (21): 15252-15257 (1992).

Herdegen et al., "Inducible and constitutive transcription factors in the mammalian nervous system: control of gene expression by Jun, Fos and Krox, and CREB/ATF proteins," *Brain Research Reviews*, 28: 370-490 (1998).

Iwasaki et al., "The Rab3 GDP/GTP exchange factor homolog AEX-3 has a dual function in synaptic transmission," *The EMBO Journal*, 19 (17): 4806-4816 (2000).

Kalnina et al., "Alterations of Pre-mRNA Splicing in Cancer," *Genes, Chromosomes & Cancer*, 42: 342-357 (2005).

Kozielski et al., "A model of the microtubule-kinesin complex based on electron cryomicroscopy and X-ray crystallography," *Current Biology*, 8: 191-198 (1998).

Lee et al., "Interaction of HCV core protein with 14-3-3xi protein releases Bax to activate apoptosis," *Biochemical and Biophysical Research Communications*, 352: 756-762 (2007).

Levivier et al., "uDENN, DENN, and dDENN: Indissociable Domains in Rab and MAP Kinasis Signaling Pathways," *Biochemical and Biophysical Research Communications*, 287: 688-695 (2001).

Li et al., "Cytochrome c and dATP-Dependent Formation of Apaf-1/Caspase-9 Complex Initiates and Apoptotic Protease Cascade," *Cell*, 91: 479-489 (1997).

Li et al., "p53 regulates mitochondrial membrane potential through reactive oxygen species and induces cytochrome c-independent apoptosis blocked by Bcl-2," *The EMBO Journal*, 18 (21): 6027-6036 (1999).

Li et al., "Phosphorylation by Protein Kinase CK2: A Signaling Switch for the Caspase-Inhibiting Protein ARC," *Molecular Cell*, 10: 247-258 (2002).

Lim et al., "Induction of Marked Apoptosis in Mammalian Cancer Cell Lines by Antisense DNA Treatment to Abolish Expression of DENN (Differently Expressed in Normal and Neoplastic Cells)," *Molecular Carcinogenesis*, 35: 110-126 (2002).

Lim et al., "Antisense Abrogation of DENN Expression Induces Apoptosis of Leukemia Cells in Vitro, Causes Tumor Regression In Vivo and Alters the Transcription of Genes Involved in Apoptosis and the Cell Cycle," *Int. J. Cancer*, 109: 24-37 (2004).

Liu et al., "Dissection of TNF Receptor 1 Effector Functions: JNK Activation Is Not Linked to Apoptosis While NF-kappaB Activation Prevents Cell Death," *Cell*, 87: 565-576 (1996).

LoPiccolo et al., "Targeting Akt in cancer therapy," *Anti-Cancer Drugs*, 18: 861-874 (2007).

Manning et al., "AKT/PKB Signaling: Navigating Downstream," *Cell*, 129: 1261-1274 (2007).

Mayo et al., "A phosphatidylinositol 3-kinase/Akt pathway promotes translocation of Mdm2 from the cytoplasm to the nucleus," *PNAS*, 98 (20): 11598-11603 (2001).

Micheau et al., "Induction of TNF Receptor I-Mediated Apoptosis via Two Sequential Signaling Complexes," *Cell*, 114: 181-190 (2003).

Mulherkar et al., "MADD/DENN splice variant of the *IG20* gene is necessary and sufficient for cancer cell survival," *Oncogene*, 25: 6252-6261 (2006).

Mulherkar et al., "MADD/DENN Splice Variant of the IG20 Gene Is a Negative Regulator of Caspase-8 Activation," *The Journal of Biological Chemistry*, 282(16): 11715-11721 (2007).

Murakami-Mori et al., "Implication of TNF Receptor-I-Mediated Extracellular Signal-Related Kinases 1 and 2 (ERK1/2) Activation in Growth of AIDS-Associated Kaposi's Sarcoma Cells: A Possible Role of a Novel Death Domain Protein MADD in TNF-alpha-Induced ERK1/2 Activation in Kaposi's Sarcoma Cells," *The Journal of Immunology*, 162: 3672-3679 (1999).

Nomura et al., "14-3-3 Interacts Directly with and Negatively Regulates Pro-apoptotic Bax," *The Journal of Biological Chemistry*, 278 (3): 2058-2065 (2003).

Ottmann et al., "Phosphorylation-independent interaction between 14-3-3 and endoenzyme S: from structure to pathogenesis," *The EMBO Journal*, 26: 902-913 (2007).

Pan et al., "The Receptor for the Cytotoxic Ligand TRAIL," *Science*, 276: 111-113 (1997).

Ramaswamy et al., "IG20 (MADD splice variant-5), a proapoptotic protein, interacts with DR4/DR5 and enhances TRAIL-induced apoptosis by increasing recruitment of FADD and caspase-8 to the DISC," *Oncogene*, 23: 6083-6094 (2004).

Schievella et al., "MADD, a Novel Death Domain Protein That Interacts with the Type 1 Tumor Necrosis Factor Receptor and Activates Mitogen-activated Protein Kinase," *The Journal of Biological Chemistry*, 272 (18): 12069-12075 (1997).

Shumueli et al., "Mdm2: p53's Lifesaver?," *Molecular Cell*, 25: 794-795 (2007).

Susin et al., "Molecular characterization of mitochondrial apoptosis-inducing factor," *Nature*, 397: 441-446 (1999).

Tanaka et al., "Role of Rab3 GDP/GTP Exchange Protein in Synaptic Vesicle Trafficking at the Mouse Neuomuscular Junction," *Molecular Biology of the Cell*, 12: 1421-1430 (2001).

Telliez et al., "LRDD, a novel leucine rich repeat and death domain containing protein," *Biochimica et Biophysica Acta*, 1478: 280-288 (2000).

Thornberry et al., "Caspases: Enemies Within," *Science*, 281: 1312-1316 (1998).

Tsuruta et al., "JNK promotes Bax translocation to mitochondria through phosphorylation of 14-3-3 proteins," *The EMBO Journal*, 23 (8): 1889-1899 (2004).

Venables, "Aberrant and Alternative Splicing in Cancer," *Cancer Research*, 64: 7647-7654 (2004).

Verhagen et al., "Identification of DIABLO, a Mammalian Protein that Promotes Apoptosis by Binding to and Antagonizing IAP Proteins," *Cell*, 102: 43-53 (2000).

Wada et al., "Isolation and Characterization of a GDP/GTP Exchange Protein Specific for the Rab3 Subfamily Small G Proteins," *The Journal of Biological Chemistry*, 272 (7): 3875-3878 (1997).

Xin et al., "Nicotine Inactivation of the Proapoptotic Function of Bax through Phophorylation," *The Journal of Biological Chemistry*, 280 (11): 10781-10789 (2005).

Yamaguchi et al., "The protein kinase PKB/Akt regulates cell survival and apoptosis by inhibiting Bax conformational change," *Oncogene*, 20: 7779-7786 (2001).

Yamaguchi et al., "A GDP/GTP exchange protein for the Rab3 small G protein family up-regulates a postdocking step of synaptic exocytosis in central synapses," *PNAS*, 99 (22): 14536-14541 (2002).

Zha et al., "Serine Phosphorylation of Death Agonist BAD in Response to Survival Factor Results in Binding to 14-3-3 Not BCX-XL," *Cell*, 87: 619-628 (1996).

Zhai et al., "Identification of a Novel Interaction of 14-3-3 with 190RhoGEF," *The Journal of Biological Chemistry*, 276 (44): 41318-41324 (2001).

Zhang et al., "A splicing variant of a death domain protein that is regulated by a mitogen-activated kinase is a substrate for c-Jun N-terminal kinase in the human central nervous system," *PNAS*, 95: 2586-2591 (1998).

Zhang et al., "Mechanisms of resistance to TRAIL-induced apoptosis in cancer," *Cancer Gene Therapy*, 12: 228-237 (2005).

Zhou et al., "HER-2/neu induces p53 ubiquitination via Akt-mediated MDM2 phosphorylation," *Nature Cell Biology*, 3: 973-982 (2001).

International Search Report issued in PCT/US2007/060712 (2007).

Li et al., "Regulation of Apoptosis and Caspace-8 Expression in Neuroblastoma Cells by Isoforms of the *IG20* Gene," *Cancer Res.*, 68 (18): 7352-7361 (2008).

International Search Report issued in PCT/US2009/050219 (2010).

* cited by examiner

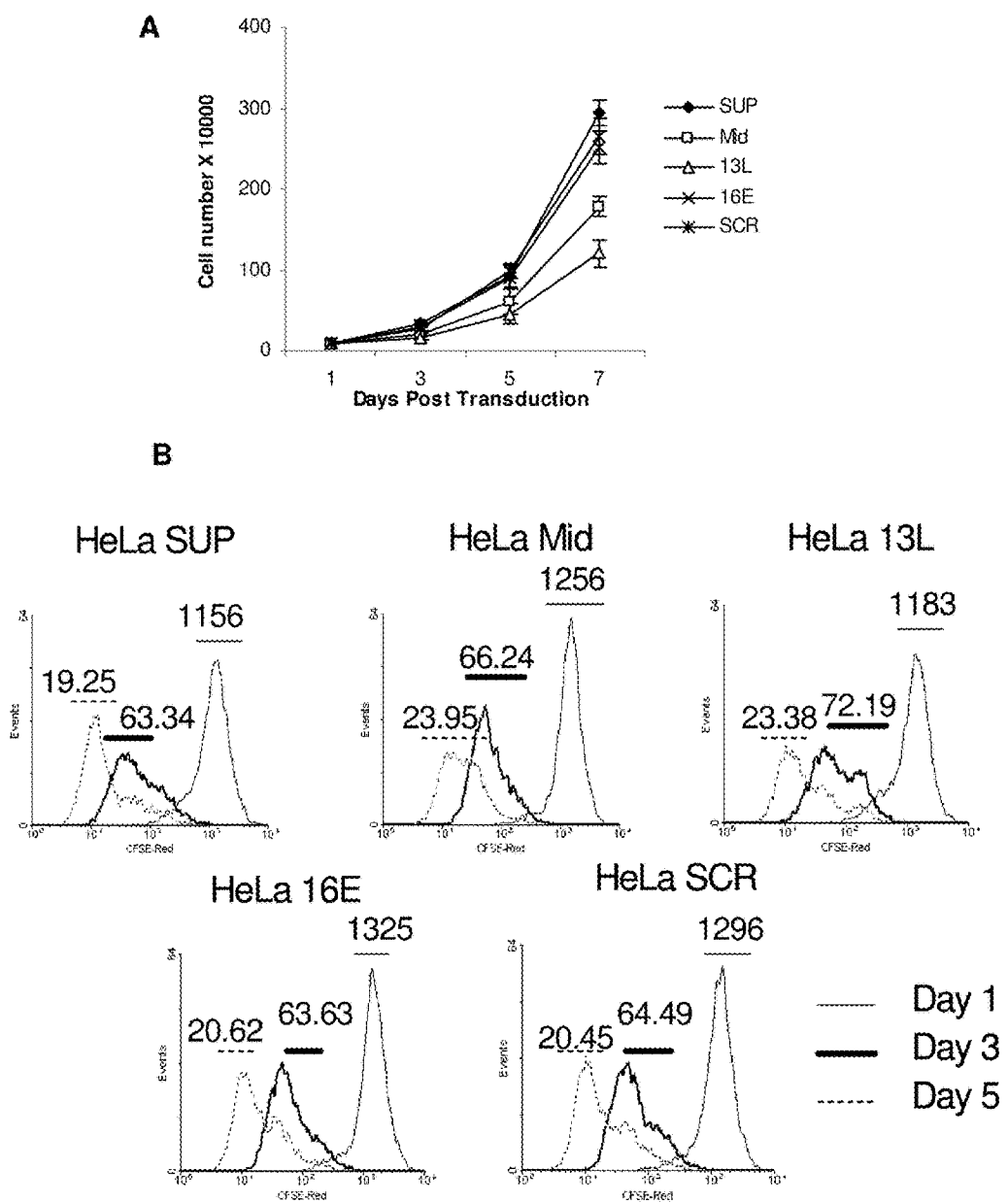
FIG. 3A-B

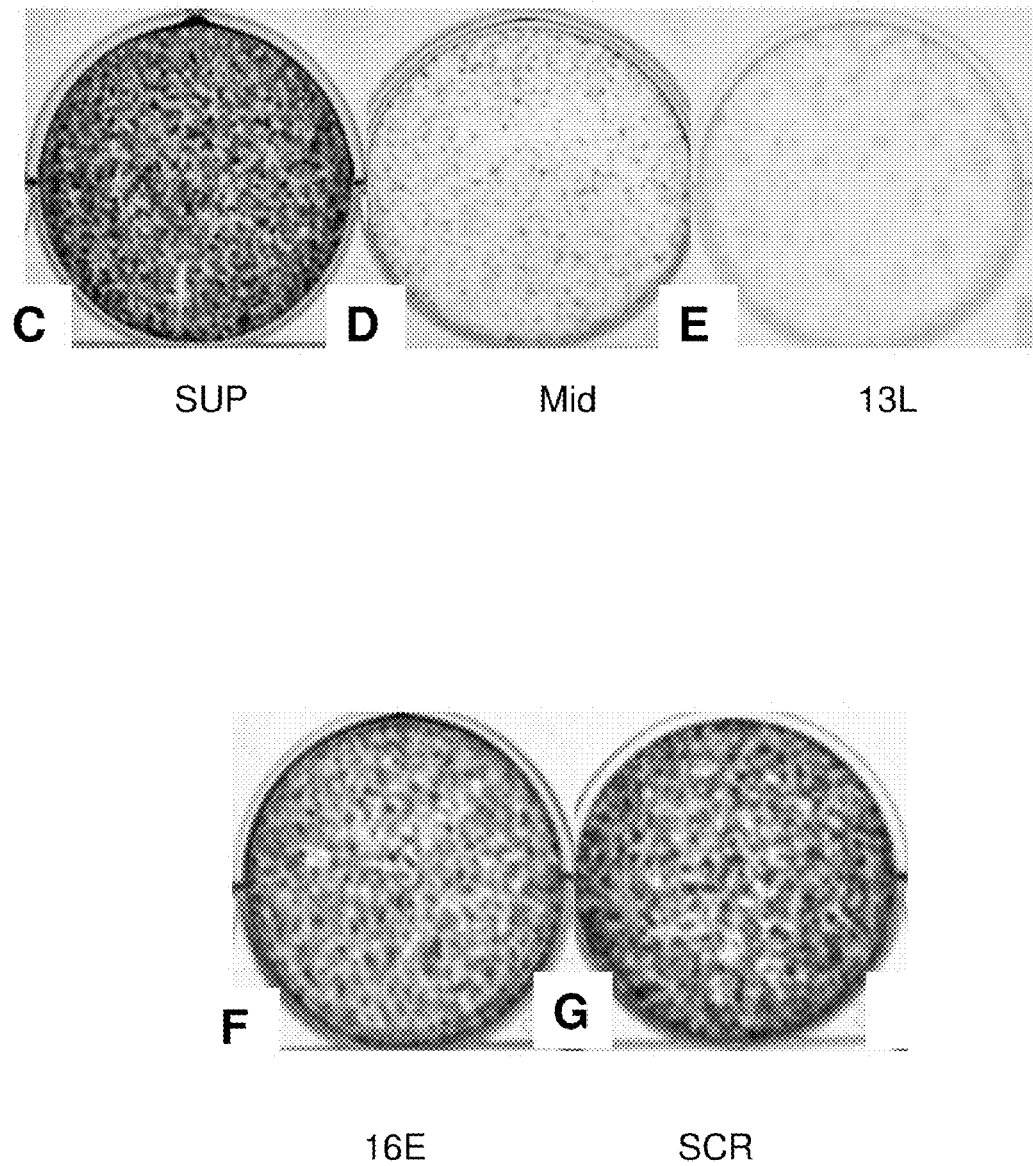
FIG. 3C-G

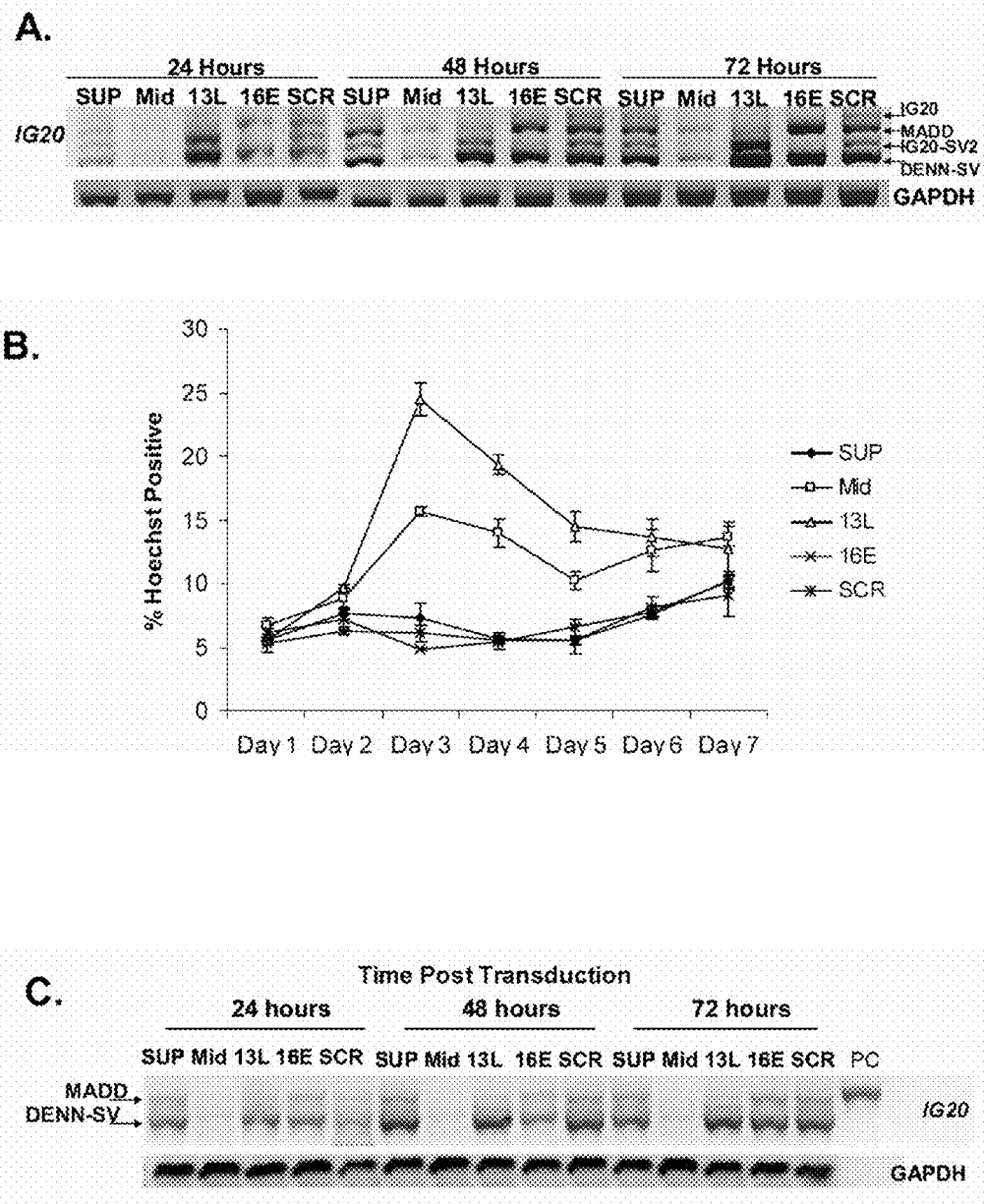
FIG. 5A-C

A

IP: anti-14-3-3

IB: Bax

IB: 14-3-3

| | | |
|---|---|---|
| wt MADD | − | + | − |
| MADD3A | − | − | + |

B

IP: anti-14-3-3

IB: Bax

IB: 14-3-3

| | | | |
|---|---|---|---|
| wtMADD | + | + | + |
| DN-Akt | − | + | − |
| pcDNA | − | − | + |

C

IP: anti-14-3-3

Bax 14-3-3

| | | | | | | | |
|---|---|---|---|---|---|---|---|
| DN-Akt | − | + | − | + | + | − | − |
| β-gal | − | − | + | − | − | − | − |
| Scrambled RNAi | − | − | − | + | − | + | − |
| MADD RNAi | − | − | − | − | + | − | + |

FIG. 17

IG20 SPLICE VARIANTS THERAPEUTICS FOR CANCER

CROSS-REFERENCE TO RELATED APPLICATIONS

This application is a continuation-in-part application under 35 U.S.C §365 of International Application No. PCT/US2007/060712, filed Jan. 18, 2007, which claims priority to U.S. Ser. No. 60/760,321, filed Jan. 19, 2006, the contents of which are hereby incorporated by reference in their entirety.

STATEMENT REGARDING FEDERALLY SPONSORED RESEARCH

The United States government has certain rights in this invention pursuant to a grant number 5R01CA107506 from the National Institutes of Health.

BACKGROUND

In eukaryotes, many genes undergo alternative splicing and encode multiple isoforms leading to the expression of related proteins that have distinct biochemical as well as biological features. The IG20 (Insulinoma-Glucagonoma) is one such gene that undergoes alternative splicing and encodes at least four different splice variants (SVs), namely IG20pa, MADD/DENN, IG20-SV2 and DENN-SV. These four IG20-SVs are distinguished by differential splicing of exons 13L and 16. Upon comparison to IG20pa, the splice variants MADD, IG20-SV2 and DENN-SV lack the expression of exon 16 or 13L, or both respectively. All four IG20-SVs express an N-terminal leucine zipper and a C-terminal death-domain homology region.

The IG20 gene plays an important role in cancer cell proliferation, apoptosis and survival, most likely through its effects on MAP kinase activation and other cell signaling pathways. Additionally, it plays an important role in neurotransmission, neurodegeneration and guanine nucleotide exchange. How IG20 is involved in these divergent functions is not yet fully known.

Expression of the IG20 gene is relatively high in cancer cells and tissues as compared to the levels of expression in their normal counterparts. While MADD and DENN-SV are constitutively expressed (DENN-SV is over-expressed relative to other SVs in cancer), expression of IG20pa and IG20-SV2 appears to be regulated in that they may or may not be expressed in certain cells. Gain of function studies through expression of individual IG20-SVs in HeLa cells showed that MADD and IG20-SV2 variants have little or no effect on cell proliferation and induced apoptosis. IG20pa increased susceptibility to both extrinsic and intrinsic apoptotic stimuli, and suppressed cell proliferation and DENN-SV conferred resistance to induced apoptosis and enhanced cell proliferation. Thus IG20pa and DENN-SV acted like a "tumor suppressor" and an "oncogene" respectively.

Knock-down of all endogenous IG20-SVs, using antisense oligonucleotides, resulted in spontaneous apoptosis of cancer cells in vitro and in vivo, but not in normal cells. Since different splice variants have different functions and the function of IG20 gene may vary depending upon the cell type, it is prudent to develop modalities that allow knockdown of specific isoforms to achieve the desired effects including altering cell growth, apoptosis, neuron-transmission. Such isoform-specifc knock-down has not yet been demonstrated. In addition, the contrasting effects of IG20-SVs noted from gain of function studies can be clarified by knocking-down individual endogenous IG20-SVs and determining the consequent effects. This poses several challenges because various IG20-SVs differ from each other only by the differential expression of very short exons 13L (130 base pairs) and 16 (60 base pairs). Therefore, knock-down of specific splice variants of IG20 gene is difficult because of availability of very short target sequences that are differentially expressed in different splice variants and is achieved through the use of specially designed small hairpin RNA molecules (shRNA) disclosed herein.

Among the IG20 isoforms, MADD-SV acts as a negative regulator of caspase-8 activation and is necessary and sufficient for cancer cell survival. Abrogation of MADD-SV, but not the other IG20-SVs rendered cancer cells more susceptible to spontaneous as well as TRAIL (tumor necrosis factor-related apoptosis-inducing ligand)-induced apoptosis. Also, the expression of MADD-SV alone in the absence of endogenous IG20-SVs is sufficient to prevent spontaneous apoptosis. MADD-SV plays a predominant role in cancer cell survival by acting as a negative regulator of caspase-8 activation. This profound effect is not due to direct association of MADD-SV with caspase-8. One possibility is that binding of MADD-SV to the receptor activates prosurvival pathways like MAP kinase or NF-kB pathway thereby antagonizing caspase-8 activation and leading to cancer cell survival.

The mitogen-activated protein kinases (MAPKs) are serine/threonine-specific protein kinases that respond to extracellular stimuli (mitogens) and regulate several important and critical cellular functions required for cell homeostasis like metabolism, cell cycle progression, expression of cytokines, motility and adherence. Hence MAP kinases influence cell survival, proliferation, differentiation, development and apoptosis. Extracellular stimuli such as cytokines, growth factors and environmental stresses lead to the sequential activation of a signaling cascade composed of MAPK kinase kinase (MAPKKK), MAPK kinase (MAPKK) and MAPK. The three main members of MAPK family are extracellular-signal-regulated kinase 1/2 (ERK1/2), c-Jun-amino-terminal kinase (JNK) and p38.

The ERK pathway is a drug target for cancer chemotherapy of all the mammalian MAPK pathways since in approximately, one-third of all human cancers there is deregulation of the pathway leading to ERK activation. When activated, ERK1/2 phosphorylates several nuclear and cytoplasmic substrates involved in a multitude of cellular processes, including transcriptional factors, signaling proteins, kinases and phosphatases, cytoskeletal proteins, apoptotic proteins and proteinases. Even though the ERK pathway can be activated by numerous extracellular signals, the pathways whereby cytokines and growth factors activate ERK signaling are of particular relevance to cancer. TNF-α, a cytokine rich in tumor stroma binds to TNFR1 (TNF receptor1) present on cancer cells and potently activates ERK MAPK. In the absence of MADD this pro-survival signaling pathway can be converted into an apoptotic signaling pathway leading to cancer cell death even in the absence of protein synthesis inhibitor like cycloheximide.

The mitogen-activated kinase activating death domain protein (MADD) is expressed at very low levels in a variety of tissues and organs under physiological conditions. However, it is over-expressed in many types of human tumors and tumor cell lines. Enforced expression of exogenous MADD has no apparent effect on cell survival, but knockdown of endogenous MADD can lead to spontaneous as well as enhanced tumor necrosis factor α-related apoptosis-inducing ligand (TRAIL) induced apoptosis, indicating that MADD is necessary for cancer cell survival. Furthermore, MADD contributes to the resistance of PA-1 ovarian carcinoma cells to TRAIL-induced apoptosis.

The extrinsic apoptotic pathway is initiated by upon death ligand (e.g. TRAIL), binding to its cognate death receptors, which undergo trimerization and recruit FADD and subsequent caspase-3 activation. MADD can bind to DRs thereby inhibit DISC formation. Knock-down of MADD causes spontaneous as well enhanced TRAIL-induced apoptosis. Thus, MADD can contribute to cell survival by blocking activation of the extrinsic apoptotic pathway.

The intrinsic pathway is initiated when a death signal induces the release of mitochondrial pro-apoptotic proteins such as cytochrome c, mitochondrial apoptosis-inducing factor and Smac/Diablo. Cytochrome c forms a complex with Apaf-1 and procaspase-9 resulting in the activation of caspase-9, while Smac/Diablo can associate with inhibitor of apoptosis proteins (IAPs) and counteract their inhibitory effects. The intrinsic pathway is regulated by the Bcl-2 family members. For example, in response to proapoptotic stimuli, the cytosolic Bax and Bad translocate to mitochondria leading to cytochrome c release into the cytosol. In contrast, Bcl-2 and Bcl-xL can associate with Bax and Bad to prevent cell death.

Apoptotic factors are controlled by a complex signaling system. For example, the pro-apoptotic function of Bad is regulated by phosphorylation that prevents Bad from inducing apoptosis. p53 function in regulating apoptosis is related to its phosphorylation status. The apoptosis repressor protein function is enabled by its phosphorylation at threonine-149. Given the important role of MADD in controlling apoptosis, there is a question whether its function is constitutive or is also regulated by other signals.

Protein kinase B (i.e. Akt) promotes cell survival by phosphorylating a variety of apoptosis-related factors containing the consensus sequence RXRXX(S/T). Akt phosphorylates mouse double minute 2 and enhances its ability to degrade p53. Akt can phosphorylate a number of apoptosis related proteins such as caspase-9, Bad, IKKα, Forkhead transcription factor, mdm2 and Yap, and play a critical role in TSC1/2, Rheb/mTOR signalling pathway. Interestingly, PI3K can also activate RAS function leading to the activation of the MAPK prosurvival pathway, in which MADD plays an important role.

Role of IG20 splice variants including MADD in cancer therapeutics was analyzed. Disruption of MADD phosphorylation by Akt results in death of cancer cells. siRNA molecules that specifically target IG20 splice variants are useful as pharmaceutical therapeutics against cancer.

SUMMARY

Methods and compositions selectively down-regulate the expression of a particular IG20 gene splice variant and thereby promote cancer cell death in cells that express the particular splice variant. For example, the MADD splice variant of IG20 gene was down regulated by the use of interfering RNA sequences that specifically down regulate MADD splice variant and the down regulation was sufficient to cause apoptotic death of cancer cells. Endogenous MADD-SV, a pro-survival IG20 splice variant plays an essential role in activating prosurvival ERK MAPK pathway upon TNF-stimulation thereby antagonizing caspase-8 activation and preventing cell apoptosis.

Using shRNAs that specifically target exon 15 that is expressed in all isoforms of IG20 and designated Mid, or exons 13L and 16 that are differentially expressed in IG20-SVs, the various splice variants of IG20 gene were selectively knocked-down in HeLa and PA-1 cells. Knock down of MADD (one of the IG20 splice variants) resulted in spontaneous apoptosis and this effect was reversible by re-expressing the MADD protein. This result indicated that MADD is required and sufficient for the survival of cancer cells. Further, knock down of MADD rendered cells more susceptible to TRAIL induced apoptosis. The increased apoptosis was associated with increased caspase-8 and caspase-3 activation. The results presented herein demonstrate that knock-down of MADD causes a significant increase in spontaneous as well as TRAIL induced cell death of cancer cells, and support the conclusion that it is MADD, and not the other three isoforms (i.e. DENN-SV, IG20-SV2 and IG20) that is required for cancer cell survival.

MADD is phosphorylated by Akt and phosphorylated MADD binds to the death receptor (DR) and prevent activation of the extrinsic apoptotic pathway. While non-phosphorylated MADD loses its binding to DR, it gains binding to 14-3-3 causing Bax disassociation from 14-3-3 and translocation to mitochondria. While loss of MADD binding to DR leads to spontaneous activation of the extrinsic pathway, Bax translocation leads to the activation of the intrinsic pathway. Moreover, TRAIL treatment causes accumulation of non-phosphorylated Akt as well as MADD, which facilitates caspase-8 activation on one hand, and Bax translocation to mitochondria on the other. These results show that MADD, depending upon Akt phosphorylation, regulates both extrinsic and intrinsic apoptotic pathways.

MADD-SV of the IG20 gene acts as a negative regulator of caspase-8 activation. The molecular mechanism of action of MADD-SV in regulating caspase-8 activation is presented herein. Down-modulation of MADD-SV facilitated caspase-8 activation without affecting TNF-α induced NF-kB activation. The ability of TNF-α, TRAIL, LPS and EGF to activate MAP kinases in the presence or absence of various IG20-SVs was analyzed. Knock-down of all IG20-SVs or MADD-SV alone resulted in a dramatic loss in ERK activation only upon TNF-α treatment. Similar effects were not seen when cells were stimulated with other ligands. Also, knock-down of MADD-SV had little or no effect on the activation of other MAP kinases such as JNK and p38 upon TNF-α treatment. Over-expression of ShRNA resistant exogenous MADD-SV followed by knock-down of all endogenous IG20-SVs restored MAP kinase activation and unequivocally demonstrated that MADD-SV is necessary and sufficient for TNF-α induced ERK activation. Down-modulation of MADD-SV, which abrogates ERK activation, rendered cancer cells more susceptible to TNF-α induced apoptosis as evidenced by enhanced caspase-3 activation and decreased activation of transcriptional factor p90RSK. These results indicate that down-modulation of endogenous MADD-SV positively regulates caspase-8 activation by abrogating ERK MAP kinase pathway.

A method of selectively inhibiting a splice variant of an IG20 (Insulinoma-Glucagonoma) gene, includes the steps of:
(a) obtaining an agent that selectively inhibits the expression of an IG20 splice variant; and
(b) contacting a cell that expresses the splice variant with the agent to inhibit the splice variant.

A suitable splice variant is MADD and a suitable agent is a molecule selected from the group that includes siRNA, shRNA and an anti-sense molecule against the IG20 splice variant.

A method of specifically down-regulating the expression of a splice variant of an IG20 (Insulinoma-Glucagonoma) gene includes the steps of:

(a) obtaining a nucleic acid molecule, wherein the nucleic acid molecule or a transcription product thereof is capable of selectively binding to a RNA molecule, the RNA molecule including a nucleic acid sequence of a MADD splice variant of the IG20 gene; and (b) contacting a cell that expresses the MADD splice variant of the IG20 gene with the nucleic acid molecule, wherein the nucleic acid molecule down-regulates the expression of the MADD splice variant.

A nucleic acid molecule includes a nucleotide sequence of CGGCGAATCTATGACAATC (SEQ ID NO: 4) or a transcribed product thereof that is sufficient to knock-down the expression of MADD splice variant or an allelic variant or a mutant thereof.

A method of inhibiting the growth of a cancer cell includes the steps of:
  (a) obtaining a nucleic acid molecule, wherein the nucleic acid molecule is capable of selectively binding to a RNA molecule of a MADD splice variant of the IG20 gene; and
  (b) contacting a cancer cell that expresses the MADD splice variant of the IG20 gene with the nucleic acid molecule, wherein the nucleic acid molecule down-regulates the expression of the MADD splice variant.

A suitable nucleic acid molecule targets exon 13L of the MADD splice variant.

A suitable nucleic acid molecule is selected from a group that includes siRNA, shRNA and anti-sense molecule against the MADD splice variant of IG20 that targets a nucleotide sequence of MADD selected from a group that includes CGGCGAATCTATGACAATC (SEQ ID NO: 4), allelic variation thereof, polymorphisms thereof, and a genetic mutation thereof.

A method of regulating the growth of a cancer cell includes the steps of:
  (a) administering a pharmaceutical composition that consists essentially of a nucleic acid that specifically down-regulates the expression of a MADD splice variant of the IG20 gene in a cancer cell; and
  (b) exposing the cancer cell to a cancer treatment selected from the group consisting of radiation therapy, chemotherapy, and antibody therapy or a combination thereof.

A method of increasing apoptotic cell death in a cancer cell includes the steps of:
  (a) administering a nucleic acid molecule capable of specifically down-regulating the expression of a MADD splice variant of an IG20 gene in a cancer cell; and
  (b) increasing the apoptotic cell death in the cancer cell.

In an aspect, the apoptotic cell death is effected by a caspase. The apoptotic cell death is also induced by a TNF-related apoptosis inducing ligand (TRAIL).

A suitable nucleic acid molecule capable of inducing apoptotic cell death includes a nucleotide sequence CGGCGAATCTATGACAATC (SEQ ID NO: 4) or an RNA equivalent thereof.

A pharmaceutical composition consists essentially of a nucleic acid sequence capable of selectively inhibiting the expression of a MADD splice variant in a cancer cell. The pharmaceutical composition includes a nucleic acid whose nucleotide sequence includes CGGCGAATCTATGACAATC (SEQ ID NO: 4) or an RNA equivalent thereof.

A vector includes a nucleic acid sequence capable of selectively inhibiting the expression of a MADD splice variant in a cancer cell, wherein the nucleic acid sequence includes CGGCGAATCTATGACAATC (SEQ ID NO: 4).

A cell includes an exogenous molecule of an interfering RNA, wherein the RNA molecule specifically down-regulates the expression of a MADD splice variant of an IG20 gene. The cell may be a cancer cell or a cell predisposed or likely to become cancerous.

An isolated nucleic acid molecule encodes a short interfering RNA, the nucleic acid includes the structure:

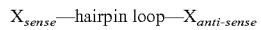

$X_{sense}$—hairpin loop—$X_{anti\text{-}sense}$ wherein X includes a nucleic acid sequence CGGCGAATCTATGACAATC (SEQ ID NO: 4). A suitable shRNA sequence is generated by a nucleic acid sequence CGGCGAATCTATGACAATCTTCAAGAGAGAT-TGTCATAGATTCGCCG (SEQ ID NO: 5), wherein the hairpin loop region is from positions 20-28 (shown as underlined). The nucleic acids may be synthetic.

An isolated RNA molecule includes a nucleic acid sequence CGGCGAAUCUAUGACAAUC (SEQ ID NO: 6).

A method of inducing cell death in a cancer cell includes:
  (a) obtaining an agent that inhibits phosphorylation of MADD at one or more sites by Akt; and
  (b) contacting a cancer cell with the agent.

Suitable agents include small molecules, peptides and peptide derivatives. For example, an agent is a MADD peptide that includes one or more phosphorylation sites for Akt. In some aspects, the agent is administered as an adjuvant therapy along with chemotherapy or radiation therapy. In some aspects, the cancer cell is resistant to TRAIL-induced apoptosis.

A method of identifying an inhibitor of the phosphorylation of MADD by Akt includes:
  (a) obtaining a candidate agent that is capable of inhibiting the phosphorylation of MADD by Akt;
  (b) testing the ability of the candidate agent to disrupt the binding of an antibody specific to a phosphorylation site of MADD selected from the group consisting of Ser (70), Thr (173) and Thr (1041); and
  (c) identifying the candidate agent as the inhibitor if the binding of the antibody to MADD is disrupted.

An antibody is generated against a peptide epitope selected from CRQRRMpSLRDDTS (SEQ ID NO: 7) (S-70), GSRSRNSpTLTSL (SEQ ID NO: 8) (T-173), and KRKRSPpTESVNTP (SEQ ID NO: 9) (T-1041), wherein Mp or Sp or Pp is a phosphorylated amino acid. In some aspects, the testing is performed in the presence of phosphorylated MADD.

A purified mutant MADD polypeptide includes one or more mutations at amino acid positions 70, 173, and 1041.

In an aspect the MADD polypeptide includes an amino acid sequence of SEQ ID NO: 3, wherein the amino acids at positions 70, 173, and 1041 are all mutated such that Akt does not phosphorylate MADD.

BRIEF DESCRIPTION OF THE DRAWINGS

FIG. 3 shows effects of IG20 down-modulation on Hela cell proliferation. Cell Growth. 24 hours post-transduction, HeLa cells were plated as described in materials and methods. Cells were then harvested and viable cells (trypan blue negative cells) were counted on indicated days. Data represent Mean+SD of triplicates. Cell proliferation. 24 hours post-transduction HeLa cells were stained with CF SE-red (SNARF-1 carboxylic acid, acetate, succinimidyl ester), harvested on indicated days and evaluated for CFSE-dilution by FACS. The numbers on the histograms indicate geometric peak mean intensities of CFSE staining in the transduced cells. Cell survival. Crystal violet staining of cells surviving upon IG20 down-modulation after transduction shown C-G.

FIG. 17 illustrates that the phosphorylation status of MADD influences the binding of 14-3-3 to Bax. (A) MADD3A but not wtMADD can cause Bax dissociation from 14-3-3. HEK293 cells were transfected with wtMADD or MADD3A, and harvested 36 h after transfection. Immunoprecipitation using an anti-14-3-3 antibody was followed by immunoblotting using an anti-Bax antibody. Protein loading was illustrated using anti-14-3-3 antibody. (B) Inhibition of Akt influences the binding of 14-3-3 to Bax. HEK293 cells were transfected with cDNAs encoding wtMADD along with DN-Akt or the empty vector pcDNA3.1. Immunoprecipitation using an anti-14-3-3 antibody was followed by immunoblotting using an anti-Bax antibody. (C) Knockdown of MADD can influence the binding of Bax to 14-3-3. HeLa cells were transduced with MADD shRNA, the scrambled shRNA, DN-Akt or β-galactosidase (β-gal). Immunoprecipitation using an anti-14-3-3 antibody was followed by immunoblottings using an anti-Bax antibody.

DETAILED DESCRIPTION

Figure 1:
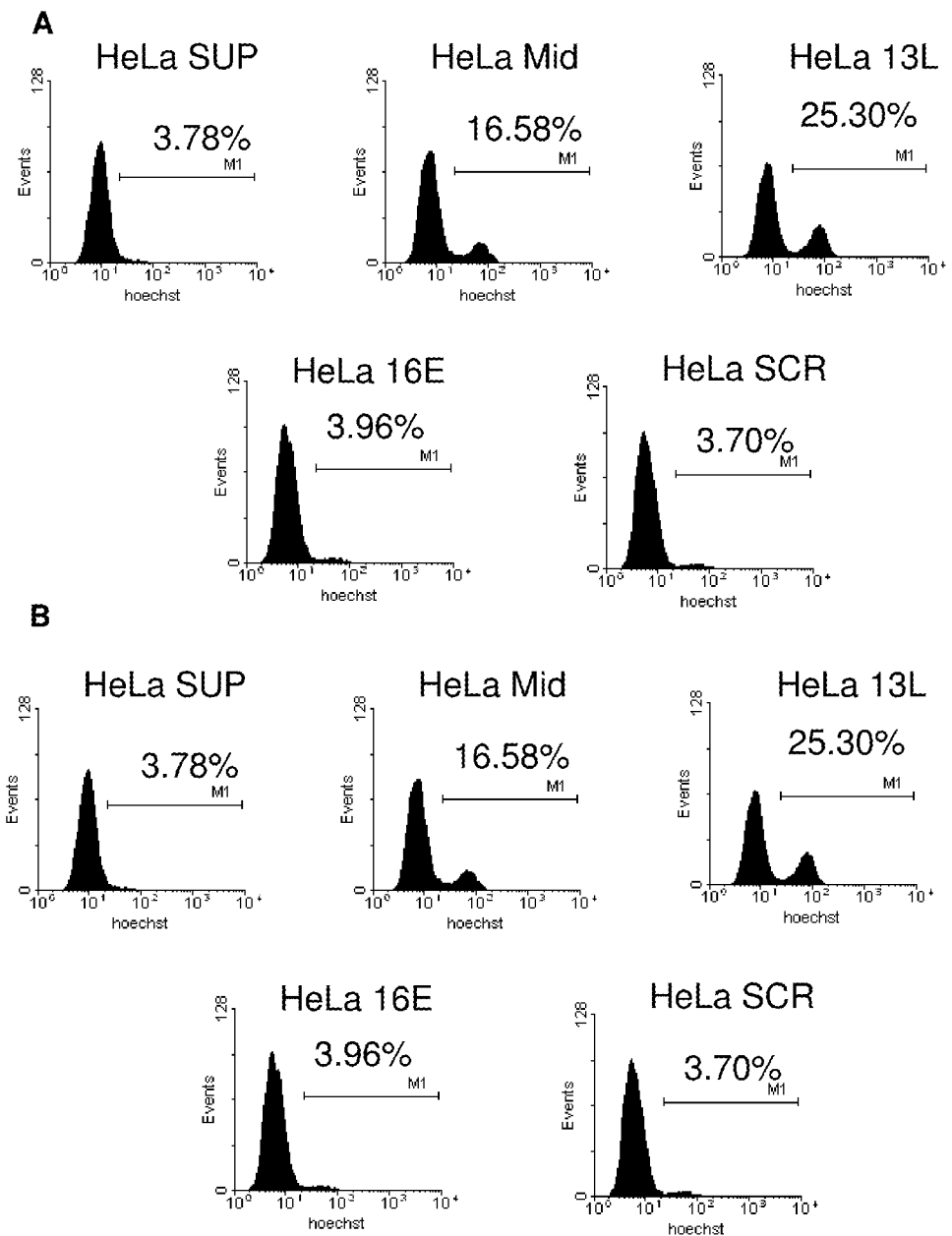
FIG. 1 illustrates effect of down-modulation of IG20-SVs in HeLa cells. (A) Summary of results showing percentage of cells with increased nuclear condensation as measured by Hoechst staining from three independent experiments. The P value was <0.005 for all test groups. Hoechst Staining-72 hours post-transduction was performed and HeLa cells were collected and stained with 1 μg/mL of Hoechst and subjected to FACS analysis. Percentages of highly positive cells (apoptotic cells) are indicated on the histograms. (B) Summary of results showing percentage of cells with increased mitochondrial depolarization from three independent experiments. The P value was <0.005 for all test groups. The data were collected from only GFP positive cells. Mitochondrial Depolarization-72 hours post-transduction was performed, HeLa cells were collected, and stained with TMRM. Loss of staining as a marker of mitochondrial depolarization was detected by FACS.

Methods and compositions described herein relate selective down-regulation of a specific IG20 splice variant to promote apoptosis of cancer cells. Through the use of specific small hairpin RNA (shRNA) molecules, knock-down of an IG20 splice variant, e.g., MADD is demonstrated. This knock-down of MADD splice variant in cancer cells resulted in apoptotic cell death. Cell death of cancer cells is further characterized by activation of caspases that are responsible for apoptotic cell death.

Down-regulation of MADD splice variant is accomplished by a number of ways. For example knock-down of MADD splice variant is accomplished through shRNA, siRNA, antisense expression, small-molecules that specifically lower the RNA levels of MADD or inactivate the activity of MADD protein, and synthetic peptide nucleic acid (PNA) oligomers (e.g., containing repeating N-(2-aminoethyl)-glycine units linked by peptide bonds).

Agents capable of down-regulating MADD expression are delivered directly to tumors, administered by a viral vector capable of transcribing and producing an interfering RNA (RNAi) molecule, liposome, and as pharmaceutical compositions. shRNAs and siRNAs can also be delivered as synthetic molecules.

The IG20 gene is over-expressed in human tumors and cancer cell lines, and encodes at least four splice variants (SVs) namely, IG20 (here referred to as IG20pa), MADD, IG20-SV2 and DENN-SV. Gain of function studies showed that IG20-SVs can exhibit diverse functions and play a critical role in cell proliferation and apoptosis. Expression of exogenous IG20pa or DENN-SV rendered cells either susceptible or resistant to induced apoptosis, respectively; while MADD and IG20-SV2 had no apparent effect.

The contrasting effects of the IG20-SVs in a more physiologically relevant system are analyzed herein by using exon-specific shRNAs to selectively knock-down specific IG20-SVs. Knock-down of all IG20-SVs resulted in spontaneous apoptosis of HeLa and PA-1 cells. Simultaneous knock-down of all the splice variants of IG20 may not be therapeutically as effective as selective knock-down because down-regulation of all the splice variants result in unexpected and undesirable outcomes because different splice variants exhibit different physiologically relevant functions such as cell growth, cell growth inhibition, neurotransmission and the like. Moreover, the IG20 gene through its splice variants, can exert different functional effects on different tissues (e.g. neurotransmission in neuronal cells). Also, knock down of all splice variants may be harmful as evidenced by the inability of IG20 gene knock-out mice to survive. Therefore, knock-down of select isoforms facilitates induction of the intended effect and minimizes harmful effects, e.g., death of normal cells.

Knock-down of MADD can render cells susceptible to spontaneous apoptosis but had no discernible effect on cell proliferation, colony size, or cell cycle progression. The utility of shRNAs for selective knock-down of particular IG20-SVs is demonstrated. MADD isoform expression is required for cancer cell survival, and therefore the methods and compositions disclosed herein are therapeutically valuable in targeting specific IG20-SVs to reduce cancer growth and thereby promoting selective cancer cell death.

MADD abrogation, in addition to causing spontaneous apoptosis, also enhances TRAIL-induced apoptosis. MADD interacts with the death receptors (DRs) but not with either the FADD or caspase-8, and the spontaneous as well as enhanced TRAIL induced apoptosis result from activation of caspase-8 at the DRs without an apparent increase in the recruitment of DISC components. Under physiological conditions, MADD acts as a negative regulator of caspase-8 activation.

Gain of function studies using exogenous IG20-SVs showed that MADD and IG20-SV2 have little or no effect on cell proliferation and susceptibility to induced apoptosis. However, IG20pa rendered cells highly susceptible to apoptosis induced by different death signals including TRAIL, and suppressed cell proliferation. In contrast, it is found that DENN-SV was over expressed in tumor tissues and cancer cell lines, and expression of exogenous DENN-SV confers resistance to apoptosis and enhance cell proliferation.

Down-modulation of select combinations of IG20-SVs using siRNAs is demonstrated herein. Synthetic siRNA duplexes or expressed shRNAs binds to the target mRNA and lead to its degradation. Specific and the most effective shRNAs against IG20-SVs were identified by screening 5 different shRNAs targeting all isoforms, and 2 each targeting exons 13L and 16 and cloned into a lentivirus vector. Use of lentivirus resulted in stable expression of shRNAs that is detected through GFP expression. Expressed shRNA down-modulated the targeted IG20-SVs as early as 24 hours post transduction and lasted at least for 15 days.

Significant increase in spontaneous apoptosis of HeLa cells with knock-down of all IG20-SVs was noted when assayed for nuclear condensation and mitochondrial depolarization; hallmarks of apoptosis. Earlier studies failed to identify the specific IG20-SV responsible, for cancer cell survival.

Significant spontaneous apoptosis was observed at 72 hours although the relevant IG20-SV transcripts were down-modulated at 24 hours. This is likely due to persistence of pre-formed proteins, although the possibility that this duration is required for either accumulation of apoptotic, or down-modulation of anti-apoptotic, molecules cannot be ruled out.

Isolated siRNA nucleic acids that selectively down-regulate the expression of a splice variant of an IG20 (Insulinoma-Glucagonoma) gene, wherein the splice variant is MADD are disclosed. In an embodiment, the nucleic acid encodes a short interfering RNA, that includes the structure:

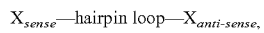

$X_{sense}$—hairpin loop—$X_{anti\text{-}sense}$, wherein X includes or consists essentially of a nucleic acid sequence CGGCGAATCTATGACAATC (SEQ ID NO: 4).

In an embodiment, the siRNA nucleic acid sequence is CGGCGAATCTATGACAATCTTCAA-GAGAGATTGTCATAGATTCGCCG (SEQ ID NO: 5), wherein the hairpin loop region is from positions 20-28 of the sequence. The hairpin loop region may contain any suitable sequence. In an embodiment, siRNA or shRNA molecules disclosed herein are synthetic and may include nucleic acid modifications to enhance stability.

RNA molecules that include a nucleic acid sequence CGGCGAAUCUAUGACAAUC (SEQ ID NO: 6) are disclosed. RNA molecules that are transcribed in vitro or in vivo, e.g., in a cancer cell or tumors are also included.

A method of specifically down-regulating the expression of a splice variant of an IG20 (Insulinoma-Glucagonoma) gene includes:
(a) obtaining the nucleic acid molecule that is capable of blocking MADD expression, wherein the nucleic acid molecule or a transcription product thereof is capable of selectively binding to a RNA molecule, the RNA molecule that includes a nucleic acid sequence of a MADD splice variant of the IG20 gene; and
(b) contacting a cell that expresses the MADD splice variant of the IG20 gene with the nucleic acid molecule, wherein the nucleic acid molecule down-regulates the expression of the MADD splice variant.

Specifically down-regulating may refer to a substantial down-regulation for example, more than 90% or 95% reduction of the endogenous MADD transcript. In some aspects, the acid molecule molecules specifically target exon 13L of the MADD splice variant. Thus, based on the target sequence and the siRNA sequences disclosed herein a variety of specific siRNA or shRNA nucleic acid molecules are designed for therapeutics.

Nucleic acid molecules that consist essentially of a nucleotide sequence CGGCGAATCTATGACAATC (SEQ ID NO: 4) or a transcribed product thereof are sufficient to knock-down the expression of MADD splice variant or an allelic variant or a mutant thereof. Natural variations of MADD including specific SNPs, allelic variants that may appear in one or more of sub-groups of the cancer types are also targeted by the nucleic acid molecules disclosed herein. Accordingly, one or more nucleic acid changes are adopted by those skilled in the art.

A method of inhibiting the growth of a cancer cell includes:
(a) obtaining the nucleic acid molecule that selectively down-regulates MADD expression, wherein the nucleic acid molecule is capable of selectively binding to a RNA molecule of a MADD splice variant of the IG20 gene; and
(b) contacting a cancer cell that expresses the MADD splice variant of the IG20 gene with the nucleic acid molecule, wherein the nucleic acid molecule down-regulates the expression of the MADD splice variant.

In some aspects, the nucleic acid molecule is selected from a group that includes siRNA, shnRNA and anti-sense molecule against the MADD splice variant of IG20 that targets a nucleotide sequence of MADD selected from CGGC- GAATCTATGACAATC (SEQ ID NO: 4), allelic variation thereof, polymorphisms thereof, and a genetic mutation thereof.

A method of regulating the growth of a cancer cell includes:
(a) administering a pharmaceutical composition consisting essentially of one or more of the nucleic acid molecules disclosed herein that specifically down-regulate the expression of a MADD splice variant of the IG20 gene in a cancer cell; and
(b) exposing the cancer cell to a cancer treatment selected from radiation therapy, chemotherapy, and antibody therapy or a combination thereof.

A method of increasing apoptotic cell death in a tumor includes:
(a) administering the nucleic acid molecule disclosed herein, the nucleic acid capable of specifically down-regulating the expression of a MADD splice variant of an IG20 gene in the tumor; and
(b) providing conditions for increasing the apoptotic cell death in the tumor.

In some aspects, the apoptotic cell death is affected by a caspase. In an aspect, the apoptotic cell death is induced by a TNFα-related apoptosis inducing ligand (TRAIL). For example, in an aspect, the down-regulation of MADD abrogates prosurvival function of TNFα-induced MAPK activation, such that apoptosis is triggered when MADD is not available for MAPK phosphorylation. The tumor may be a solid tumor. TNFα usually activates MAPK in tumor stroma and facilitates neovasculogenesis required for tumor survival (nutrition). However, upon MADD knock-down this prosurvival function is switched to apoptosis.

A method of selectively inhibiting a splice variant of an IG20 (Insulinoma-Glucagonoma) gene includes:
(a) obtaining a siRNA that selectively inhibits the expression of an IG20 splice variant; and
(b) contacting a cell that expresses the splice variant with the siRNA to inhibit the splice variant.

Pharmaceutical compositions consisting essentially of the nucleic acid, e.g., CGGCGAATCTATGACAATC (SEQ ID NO: 4) or an RNA equivalent thereof capable of selectively inhibiting the expression of a MADD splice variant in a cancer cell are disclosed. Pharmaceutical compositions may also include pharmaceutical carriers, incipients and any other ingredients suitable for nucleic acid or peptide delivery.

Vectors that include the nucleic acid molecule having a sequence CGGCGAATCTATGACAATC (SEQ ID NO: 4) capable of selectively inhibiting the expression of a MADD splice variant in a cancer cell are disclosed. The vectors are capable of delivering the nucleic acid molecules to a plurality of tumor cells. The vectors may also be part of a liposome or any suitable carrier.

Cells including host cells, transformed cells, transformed tumor cells include the nucleic acid molecule e.g., having a sequence CGGCGAATCTATGACAATC (SEQ ID NO: 4) or an RNA equivalent thereof, wherein the nucleic acid specifically down-regulates the expression of a MADD splice variant of an IG20 gene.

A method of inducing cell death in a cancer cell includes:
(a) obtaining an agent that inhibits phosphorylation of MADD at one or more sites by Akt; and
(b) contacting a cancer cell with the agent.

In an embodiment, an agent is selected from small molecules, peptides and peptide derivatives. For example, a suitable agent is a MADD peptide that includes one or more phosphorylation sites for Akt, and the MADD-derived peptide is capable of interacting with Akt and serves as a phosphorylation substrate, thereby competing with the endogenous MADD and prevents MADD phosphorylation by Akt. Suitable MADD-derived peptides or polypeptides include for example one or more of the phosphorylation sites of MADD and in some aspects include all 3 phosphorylation sites. In an aspect, the MADD-derived peptides compete for Akt phosphorylation and thereby prevents or minimizes MADD phosphorylation by Akt. In some aspects, the MADD-derived peptides block Akt-MADD phosphorylation by for example, binding to a kinase active site of Akt or through steric hindrance to phosphorylation. Suitable lengths of MADD-derived peptides or polypeptides include for example, 25, 50, 75, 100, 200, 300, 400, 500, 600, 750, 1000, or full-length MADD with one or more mutations that render the MADD incapable of binding to DR. In some aspects amino acid sequences comprising contiguous sequences from MADD e.g., amino acid positions 70-1041, 50-1100, 173-1041, 70-173, 50-200, 150-1100, 1-173, 1-1041 and 1-200 of MADD are suitable such that interact with Akt to prevent Akt phosphorylation of MADD and thereby preventing pro-survival functions of MADD in a cancer cell.

In certain embodiments, the compositions disclosed herein e.g., nucleic acid molecules that selectively down-regulate MADD expression of peptide molecules that block Akt-phosphorylation of MADD may be administered as an adjuvant therapy along with chemotherapy or radiation therapy. The compositions may also be administered prior to a standard cancer therapy and may optionally be administered along with or after cancer therapy. Examples of cancer therapy include for example, doxorubicin, cisplatin, antibody-therapy, and radiation therapy. In some aspects, the compositions disclosed herein sensitize resistant cancer cells, e.g., wherein the cancer cell is resistant to TRAIL-induced apoptosis.

A method of identifying an inhibitor of the phosphorylation of MADD by Akt includes:
(a) obtaining a candidate agent that is capable of inhibiting the phosphorylation of MADD by Akt;
(b) testing the ability of the candidate agent to disrupt the binding of an antibody specific to a phosphorylation site of MADD selected from the group consisting of Ser (70), Thr (173) and Thr (1041); and
(c) identifying the candidate agent as the inhibitor if the binding of the antibody to MADD is disrupted.

Suitable inhibitors include for example, small molecules and peptides. Antibody for identifying an inhibitor is generated against a peptide epitope selected from the group e.g., CRQRRMpSLRDDTS (SEQ ID NO: 7) (S-70), GSRSRNSpTLTSL (SEQ ID NO: 8) (T-173), and KRKRSPpTESVNTP (SEQ ID NO: 9) (T-1041), wherein Mp or Sp or Pp is a phosphorylated amino acid. In an embodiment, the testing is performed in the presence of phosphorylated MADD.

Suitable assays to identify inhibitors of MADD phosphorylation include for example, a high throughput screening system for agents that can bind to MADD and prevent its prosurvival function and thus result in enhanced apoptosis. In an aspect, the screening method may include two steps. For example, first to screen for the compound that can enhance apoptosis and second to determine the compound's binding to phosphorylated MADD. Alternatively, screening for compounds that can bind only to phospho MADD followed by testing to determine the compounds' abilities to induce/enhance apoptosis. Standard assays techniques are used to determine the binding efficiency to the phosphopeptides of MADD.

In another aspect, in vitro assays are designed to monitor/ identify the ability of the inhibitors to block either MAPK's or Akt's ability to phosphorylate MADD by analyzing the binding of anti-phospho-MADD antibodies. If, in the presence of a candidate agent (e.g., inhibitor), the phosphorylation of MADD does not account at one or more of the positions at 70, 173 or 1041 as compared to the control, as determined by e.g., lack of detection by the phospho antibodies, then the candidate agent is further evaluated for its ability to induce apoptosis in a cancer cell.

Phosphor peptides derived from MADD are used in NMR based screening for compounds. For example, each of these peptides has a particular NMR spectrum that may change upon binding of a small molecule or a compound. Based on the alterations in the NMR spectrum upong being exposed or contacted with a candidate agent (e.g., small molecule), a large number of candidate agents for example, from a commercially available library (e.g., SPECS) or any other collection, is screened in a high-through put fashion to identify agents that selectively bind or interact with the phosphorylated MADD or a peptide thereof.

A purified mutant MADD polypeptide includes one more mutations at amino acid positions 70, 173, and 1041. In an embodiment, the MADD polypeptide includes an amino acid sequence of SEQ ID NO: 3 that has amino acids at positions 70, 173, and 1041, which are all mutated such that Akt does not phosphorylate MADD.

To determine the requirement of DENN-SV in cancer cell growth and proliferation, exon 13L- and 16-specific shRNAs were expressed in HeLa cells. Significant increase in spontaneous apoptosis was observed when IG20pa/MADD, but not when IG20pa/IG20-SV2, were down-modulated (FIG. 1) without affecting the levels of DENN-SV expression. These observations were further substantiated by the observed caspase activation, including caspase-8 and -9 (FIG. 2), and indicated that abrogation of MADD expression alone can induce spontaneous apoptosis of HeLa cells.

Cancer cells die as a consequence of apoptosis due to prolonged arrest in either G1/S or G2/M phases of cell cycle or due to their inability to replicate. Diminished viability of cells upon Mid- and 13L-shRNA expression (FIG. 3) was not a consequence of defective cell proliferation or perturbed cell cycle progression, but was a direct consequence of spontaneous apoptosis. Microscopic examination revealed similar colony size indicating no significant changes in cell growth due to knock-down of various IG20-SVs.

Figure 2:
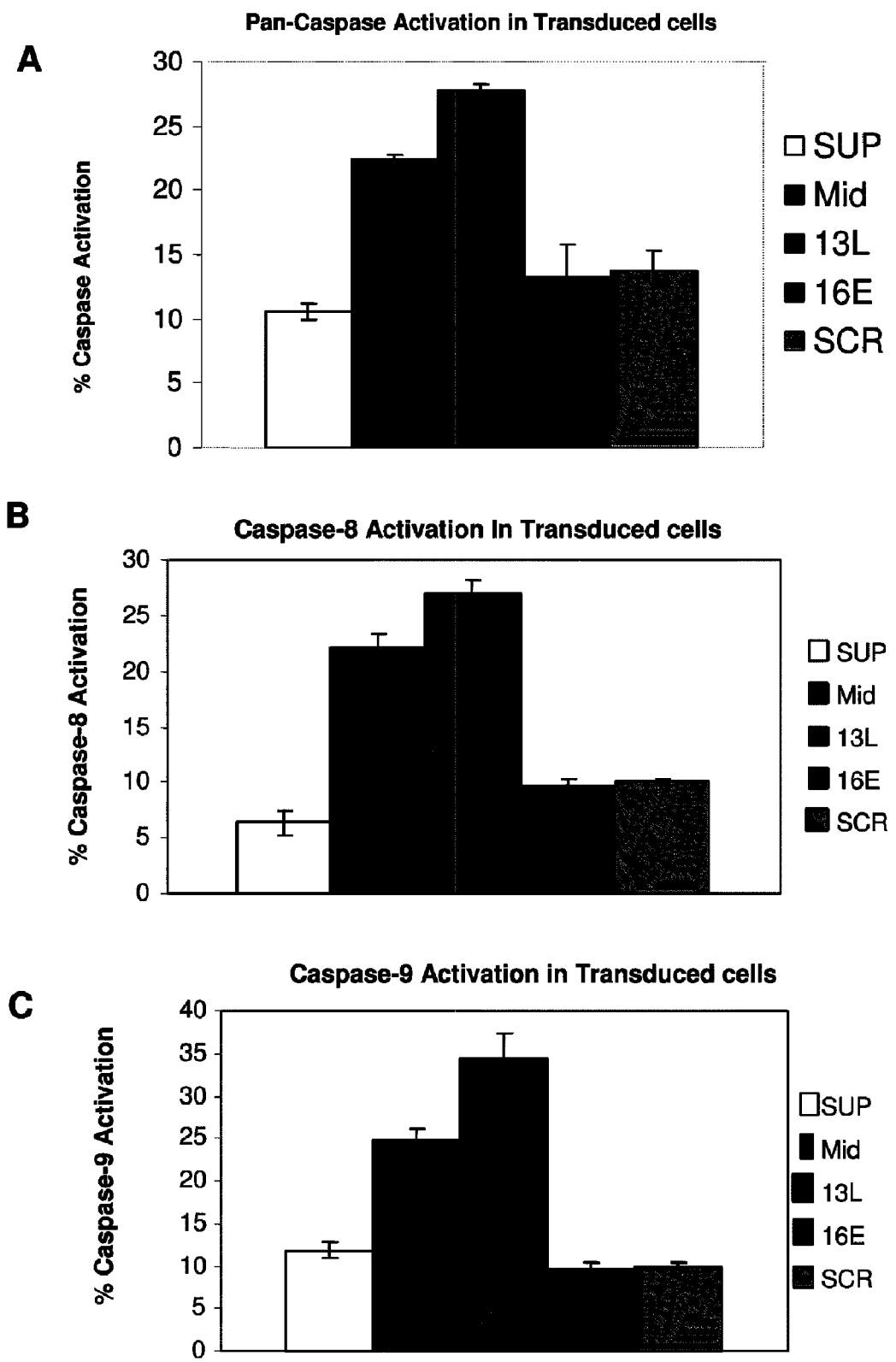
FIG. 2 shows activation of caspases upon down-modulation of IG20-SVs. (A) General activation of caspases-60 hours post-transduction, HeLa cells were collected and stained for all activated caspases using Red-z-VAD-FMK; (B) for Caspase-8 with RedIETD-FMK; and (C) for Caspase-9 with Red-LEHD-FMK, and analyzed by FACS. Percentage caspase activation in GFP-positive cells is shown (Mean+SD of triplicates).

Apoptosis was consistently higher in 13L-treated, relative to Mid-treated, cells (FIG. 1). However, this difference was obscured when a larger amount of MidshRNA virus was used suggesting that relative to the amount of 13LshRNA required to target IG20pa/MADD a larger amount of Mid-shRNA is required to knock-down all 4 SVs.

Unlike HeLa cells that express all 4 IG20-SVs, the PA-1 (ovarian carcinoma) cell line expresses predominantly MADD and DENN-SV. This cell line was used to unambiguously demonstrate the role of MADD in promoting cancer cell survival. The results obtained on cell proliferation and cell cycle progression with PA-1 cells were very similar to the observations made in HeLa cells, and thereby supported the finding that MADD but not any of the other three IG20-SVs can promote cancer cell survival.

Down-modulation of MADD alone can cause spontaneous apoptosis. However, over-expression of exogenous MADD had no discernible effect on induced apoptosis or cell proliferation. Although the mode of action of MADD is not known, it can bind to death receptors (DRs) and thus might prevent spontaneous oligomerization of DRs that leads to apoptosis. If the endogenous MADD (a pro-survival molecule) was sufficient to prevent DR oligomerization, expression of exogenous MADD might have had little or no effect. On the other hand, either down-modulation of MADD or expression of exogenous IG20pa (a pro-apoptotic molecule), which might act as a dominant negative, renders cells susceptible to apoptosis by facilitating DR oligomerization. In contrast, expression of exogenous DENN-SV (an anti-apoptotic molecule) stabilizes or synergizes MADD and prevent apoptosis. While IG20pa enhanced TRAIL-induced apoptosis was accompanied by increased recruitment of death-inducing signaling complex (DISC) and caspase activation; DENN-SV induced resistance was characterized by enhanced NFkB activation. Data presented herein demonstrate the requirement of MADD for cancer cell survival and the clinical implication of selective abrogation of MADD.

Data presented herein also demonstrated that MADD abrogation can lead not only to spontaneous apoptosis but also to enhanced TRAIL-induced apoptosis resulting from caspase-8 activation at the DRs and strongly indicated that MADD acts as a negative regulator of caspase-8 activation in cancer cells.

The levels of expression of DRs and DcRs, or their ligands were unperturbed. Expression of CrmA, a known inhibitor of caspase-1 and -8, or DN-FADD that competes with endogenous FADD conferred resistance to spontaneous apoptosis. Increased activation of caspase-8 at the DISC was evident from an increase in the p43/p41 fragments. Caspase-8 activation resulting from MADD abrogation was not accompanied by an increase in the recruitment of FADD or caspase-8 to the DISC (FIG. 5).

Figure 5D:
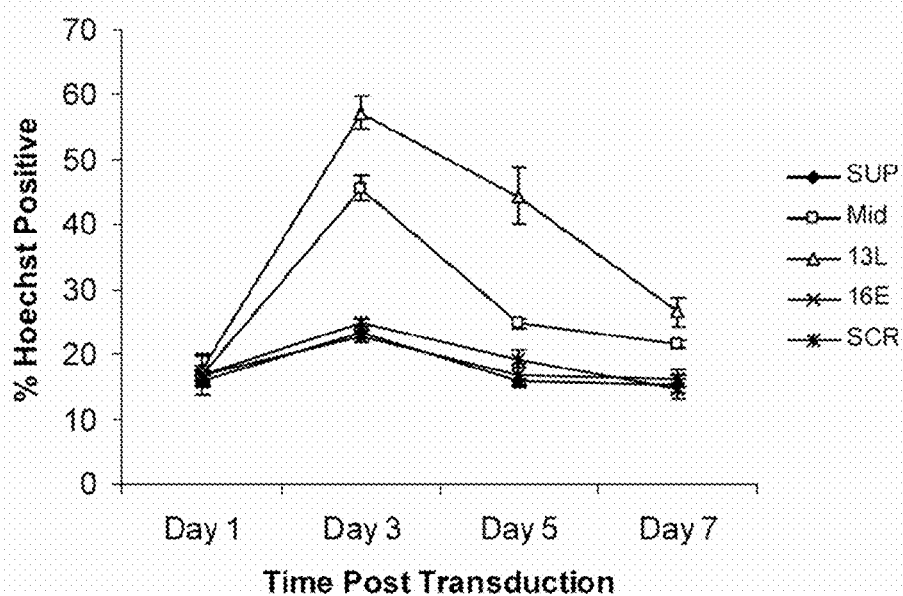
FIG. 5 shows MADD down-modulation in HeLa and PA-1 cells results in spontaneous apoptosis. (A) and (C) show RT-PCR profile of IG20-SVs at 24, 48 and 72 hours post shRNA-transduction in HeLa and PA-1 cells respectively. (B) and (D) show spontaneous apoptosis as measured by Hoechst staining in transduced HeLa and PA-1 cells respectively. Data shown represent Mean±SD of triplicates.

Although MADD transcripts are depleted by 24 h post-transduction of shRNAs, it takes 72 h for spontaneous apoptosis to set in (FIG. 5). This enabled to determine susceptibility to TRAIL-induced apoptosis of MADD-depleted cells. These results showed that MADD abrogation can cause increased caspase-8 activation at the TRAIL-DISC and result in caspase-3 activation, again, without enhancing the DISC formation.

Over-expression studies failed to indicate a role for MADD in enhanced cell survival. This would suggest that endogenous MADD might be sufficient to fully exert its function and the effects of exogenous MADD, if any, thus may not be apparent. Similarly, although exogenous IG20pa can enhance induced-apoptosis, IG20pa knock-down failed to confer resistance to TRAIL-induced apoptosis. Since IG20pa can be a part of TRAIL-induced DISC, it may act as a dominant-negative MADD and render cells more susceptible to induced-apoptosis. Similarly, over-expression of DENN-SV enhanced cell proliferation and resistance to apoptosis and expression of DENN-SV in the absence of MADD did not prevent apoptosis. DENN-SV, due to its ability to enhance NFκB-activation, might complement the pro-survival function of MADD and thus, upon over expression, can enhance cell survival and proliferation.

Figure 10:
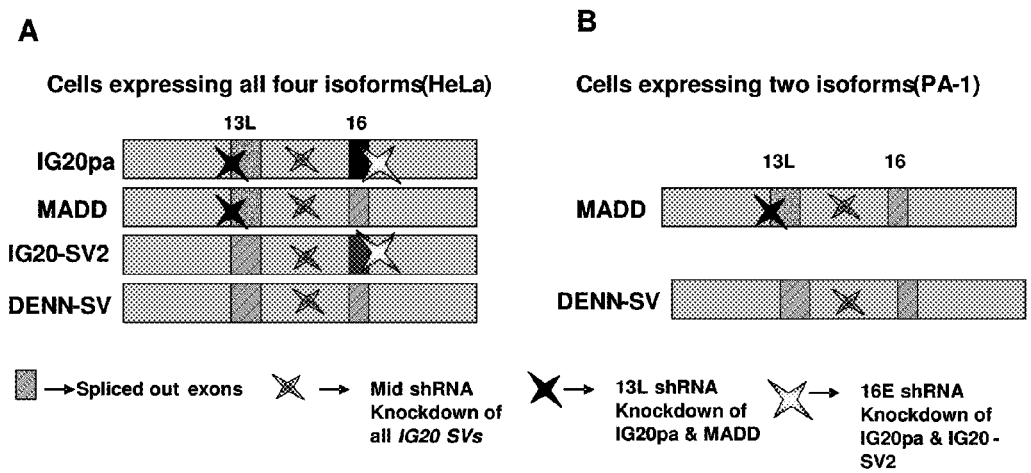
FIG. 10 is a schematic illustration of the targets of some of the shRNAs used to knock-down specific IG20 splice variants (isoforms).

Although the mode of action of MADD is not yet known, it can bind to DRs, but not to FADD or caspase-8, and prevent activation of caspase-8 without affecting DR-FADD or FADD-caspase-8 interactions (FIG. 10). The proximity-induced dimerization model for caspase-8 activation suggests that increased proximity of pro-caspase-8 molecules at the receptor allows them to dimerize and undergo activation. Therefore, MADD sterically hinders caspase-8 homodimerization and/or activation through its interaction with the DRs. It is also possible that MADD association with the DRs can lead to recruitment of other molecules that can either antagonize caspase-8 (e.g. c-FLIP) or are required for the activation of an alternate survival pathway (e.g. MAPKs) that may counteract caspase-8. Nevertheless, results show that MADD can constitutively bind to DRs, and not to FADD or caspase-8, and prevent caspase-8 activation. The fact that loss of endogenous MADD can induce significant spontaneous apoptosis of cancer cells and also enhance their ability to undergo TRAIL-induced apoptosis makes this pathway a therapeutic target that is useful either alone or in conjunction with TRAIL for cancer therapies.

Breast cancer is a leading cause of cancer related deaths among women. Current therapies, such as paclitaxel, can be toxic and may result in severe side effects including hypotension, bradycardia and peripheral neuropathies. Therefore, new safer treatments are desirable. The IG20 gene plays a critical role in cell proliferation and apoptosis and is highly over-expressed in human tumors and cancer cell lines. It encodes four splice variants (SVs) IG20pa, MADD, IG20-SV2 and DENN-SV. Earlier, over-expression studies showed that IG20pa can act as a tumor suppressor, while DENN-SV can act as an oncogene. More recently, selective knock-down of IG20 SVs revealed that the MADD isoform alone is necessary and sufficient for HeLa and PA-1 cell survival. Knock-down approach involves using a GFP-tagged lentivirus to deliver siRNAs into cells and measuring apoptosis by TMRM staining followed by flow cytometry. Interestingly, normal cells are relatively unaffected by the down-modulation of MADD. MADD protects these cancer cells by acting as a negative regulator of caspase-8 activation and therefore, suggests that MAD knock-down might synergize therapies for breast cancer. Knock-down of MADD, in MCF-7 human breast cancer cell line, and not other isoforms resulted in enhanced spontaneous apoptosis compared to cells treated with a scrambled siRNA. Moreover, knock-down of MADD in MCF-7 cells followed by treatment with sub-optimal doses of TRAIL resulted in enhanced cell death compared to either treatment alone. These data support the notion that knock-down of MADD may synergize with different modalities of breast cancer therapy resulting in reduced side effects and improved quality of life.

The MADD cDNA sequence is available on the GenBank database using accession number: NM_130470. The interfering RNAs disclosed herein that down-regulate MADD are intended to target any allelic variants and naturally occurring mutants of MADD, and polymorphisms that occur in MADD that are found in a particular segment of the population. In other words, sequences that are highly similar (e.g., about 95% at the amino acid level and about 75% at the nucleic acid level) that represent naturally occurring variations in MADD are within the scope of the disclosure, wherein the shRNAs and siRNAs disclosed herein are capable of down-regulating the expression of such sequences. The shRNA sequences presented herein provide a framework and the specification provides guidance to design additional nucleic acid sequences capable of producing interfering RNAs to down-regulate MADD splice variant. MADD sequences that are about 80% or 90% or 95% similar at the nucleic acid level to the MADD sequence disclosed herein are also down-regulated. Accordingly, nucleic acid sequences that generate shRNAs can be redesigned to accommodate the variations if those variations occur within the target region.

Data presented herein demonstrate that MADD has a dual apoptosis-regulating function depending on its phosphorylation status. It prevents apoptosis when it is phosphorylated by Akt, but when non-phosphorylated, it triggers apoptosis. Furthermore, phosphorylated MADD quenches the extrinsic apoptotic pathway, while nonphosphorylated MADD triggers apoptosis by releasing the extrinsic pathway on hand, and activating the intrinsic pathway on the other. Therefore, phosphorylation-dependent dual functions of MADD play an important role in cellular homeostasis. MADD has three potential Akt phosphorylation sites, serine-70, threonine-173 and threonine-1041. Data demonstrate that Akt can phosphorylate MADD at these three sites. And only phosphorylated MADD binds to DR4 and inhibits both spontaneous and TRAIL-induced activation of the extrinsic apoptotic pathway. This binding is significantly weak when any of the three phosphorylation sites is mutated. This indicates that phosphorylation of all three sites contributes to MADD binding to DRs. Non-phosphorylated MADD neither binds to DR nor can prevent activation of the extrinsic apoptotic pathway. In contrast, non-phosphorylated MADD now binds to the protein 14-3-3 and dislodges Bax from 14-3-3 resulting in Bax translocation to mitochondria leading to the activation of the intrinsic apoptotic pathway. Furthermore, TRAIL-induced apoptosis was dependent upon reduced levels of Akt and MADD phosphorylation. Thus, Akt phosphorylated MADD, contributes to cell survival, while the non-phosphorylated MADD allows activation of extrinsic and intrinsic apoptotic pathways leading to cell death.

MADD has a dual function in regulating apoptosis depending on its phosphorylation by Akt. Akt can phosphorylate the proapoptotic protein Bad and facilitates its binding to 14-3-3 in the cytosol and prevents translocation to mitochondria where it can exert its proapoptotic effect. Bax is also regulated by Akt signaling pathway in that it phosphorylates Bax on Ser184 and prevents its translocation to mitochondria. In contrast, phosphorylation of MADD by Akt not only allows it to bind to DR and block activation of the extrinsic pathway, but it also prevents its interaction with 14-3-3 which is required for Bax release leading to activation of the intrinsic pathway. Thus, MADD can be either anti-apoptotic or pro-apoptotic depending on its phosphorylation by Akt.

The extrinsic apoptotic pathway is quenched by MADD upon phosphorylation. MADD may exert its anti-apoptotic effect by binding to DR4, and preventing death receptor oligomerization. Present data show that only phosphorylated MADD can bind to DR4 and attenuate TRAIL-induced DISC formation. It is possible that phosphorylation facilitates MADD association with DR4 and/or controls MADD cellular localization.

The intrinsic apoptotic pathway is provoked by the non-phosphorylated MADD Mitochondria play a pivotal role in apoptosis by releasing various apoptotic molecules into the cytoplasm triggered by the translocation of proapoptotic proteins into mitochondria. For example, Bax resides predominantly in the cytoplasm of healthy cells, but upon treatment with apoptotic stimuli it translocates to mitochondria where it forms oligomers and causes cytochrome c release. Akt can suppress Bax translocation to mitochondria by facilitating its interaction with 14-3-3 in the cytosol. Other proapoptotic proteins, such as hepatitis C virus core protein, can interact with 14-3-3 thereby allowing Bax to dissociate from 14-3-3 and translocate to mitochondria leading to apoptosis. Similarly, non-phosphorylated form of MADD can interact with 14-3-3 causing release of Bax from Bax/14-3-3 complex and its translocation to mitochondria. Since 14-3-3 can also bind to other proapoptotic proteins (e.g. Bad), it is possible that MADD can similarly disrupt those associations.

Although only phosphorylated forms of some apoptotic proteins such as Bad and FOXO3a can bind to 14-3-3, the findings presented here are consistent data that show protein binding to 14-3-3 that is not necessarily dependent on phosphorylation.

How can nonphosphorylated MADD influence the association of 14-3-3 with Bax? c-Jun NH2-terminal kinase (JNK) promotes Bax translocation to mitochondria through phosphorylation of 14-3-3. Phosphorylation of 14-3-3 leads to Bax dissociation and translocation to mitochondria. A C-terminal fragment of MADD (amino acids 1396-1588) without the three phosphorylation sites is able to activate JNK, whereas the intact MADD is unable to activate JNK. This may explain why only the non-phosphorylated MADD can dissociate Bax from 14-3-3.

TRAIL initiates apoptosis by reducing MADD phosphorylation levels. TRAIL is able to induce apoptosis in a wide variety of cancer cells with minimal cytotoxity to most normal cells and tissues, and thus considered a promising cancer therapy. Resistance to TRAIL-mediated apoptosis induction in cancer cells exists. Data presented herein show that TRAIL could not only reduce Akt activity but also the levels of MADD phosphorylation, and indicates that MADD can act as a key regulator of TRAIL induced apoptosis through Akt phosphorylation.

The association of phosphorylated MADD with DR4 can quench the TRAIL-induced death signal mediated through the extrinsic pathway. However, upon TRAIL treatment the levels of nonphosphorylated MADD increases resulting in its dissociation from DR4, which allows for the activation of the extrinsic apoptotic pathway. TRAIL can also initiate the intrinsic pathway by increasing the levels of non-phosphorylated MADD, which upon binding to 14-3-3 causes Bax release and translocation to mitochondria. Thus MADD can be a downstream target of TRAIL that facilitates TRAIL-induced activation of the intrinsic pathway.

The pathophysiological significance of MADD phosphorylation by Akt. One of the major obstacles for effective cancer therapy is the development of resistance to chemotherapy and radiation therapy. The molecular mechanisms by which the resistance develops appear different for different cancers. Activation of Akt is common in many cancers, and promotes cell survival. Akt is activated in multiple myeloma, lung cancer, breast cancer, brain cancer, gastric cancer, acute myelogenous leukemia, endometrial cancer, melanoma, renal cell carcinoma, colon cancer, ovarian cancer, and prostate cancer and may contribute to less than optimal outcome following radiation and chemotherapy resulting in poor prognosis. Thus, targeting PI3K and Akt is an effective adjuvant therapy for cancers. Similarly, TRAIL may be an effective treatment for a variety of cancers. However, the possibility that the treatment itself can quickly induce resistance and promote metastasis can limit its potential usefulness. Therefore, by blocking PI3K or Akt, or modulating Akt substrates, resistance may be minimized and could serve as effective adjuvant therapies. The results provided herein indicate that modulating the Akt-MADD signaling pathway represents an effective adjuvant therapeutic approach to treat cancer.

MADD-SV acts as a negative regulator of caspase-8 activation and promotes cancer cell survival and prevents cell apoptosis. The effect of MADD-SV on caspase-8 activation is not due to the direct association of MADD-SV with caspase-8. How MADD-SV of the IG20 gene acts a negative regulator of caspase-8 activation is analyzed herein.

Figure 21:
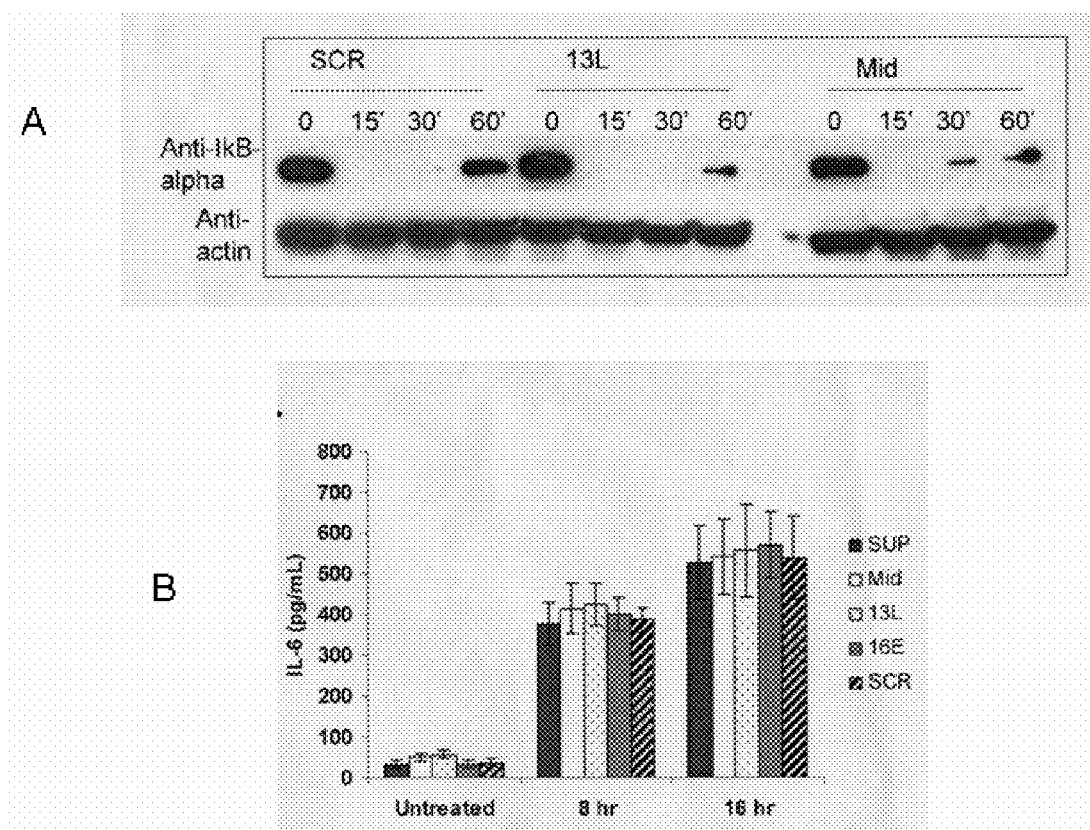
FIG. 21 shows that down-modulation of IG20-SVs or MADD-SV alone does not have any apparent effect on NF-kB activation. (A) Thirty-six hours post-transduction, HeLa cells were treated with TNF-α (50 ng/mL) and at indicated time-points post-stimulation, the cells were collected, lysed and probed for IkB-α and actin. (B) HeLa cells transduced with respective lentiviral vectors for 36 h were either left unstimulated or stimulated with TNF-α (50 ng/mL) for 8 and 16 h respectively. The supernatant media were collected from the HeLa plates and an ELISA for IL-6 was carried out.

One possible mechanism is that binding of MADD-SV to the receptor results in the activation of a prosurvival pathway which can antagonize caspase-8 activation. It was tested whether NF-kB pathway, which is a well characterized survival pathway, is involved in negative regulation of caspase-8 activation by MADD-SV. Since over-expression of MADD-SV did not have any role in the NF-kB pathway, this possibility was tested using the knock-down approach employing TNF-α stimulation. Inability to activate NF-kB pathway can render cells extremely susceptible to apoptosis. Data presented in FIG. 21A indicate that the pattern of IKB-α degradation upon MADD-SV or all IG20-SVs down-modulation was no different from the SCR control. This was further confirmed by measuring the levels of IL-6 secretion which is an NF-kB responsive gene (FIG. 21B). These data indicate that the down modulation of MADD-SV does not result in the inability to activate NF-kB and it facilitates caspase-8 activation without impairing NF-kB activation. This indicated that NF-kB pathway is not involved in the regulation of caspase-8 activation by MADD-SV.

Whether the activation of MAP kinase pathway which is another important survival pathway, plays a role in antagonizing caspase-8 activation by MADD-SV was examined. Over-expression studies have shown that MADD-SV binds to TNFR1 and can activate ERK1/2 MAP kinases. It was determined whether endogenous MADD-SV plays an essential role in TNF-α induced ERK activation pathway thereby antagonizing caspase-8 activation. This phenomenon was studied in a physiologically more relevant system by using ShRNA to knock-down endogenous isoforms of the IG20 gene including MADD-SV.

Figure 22:
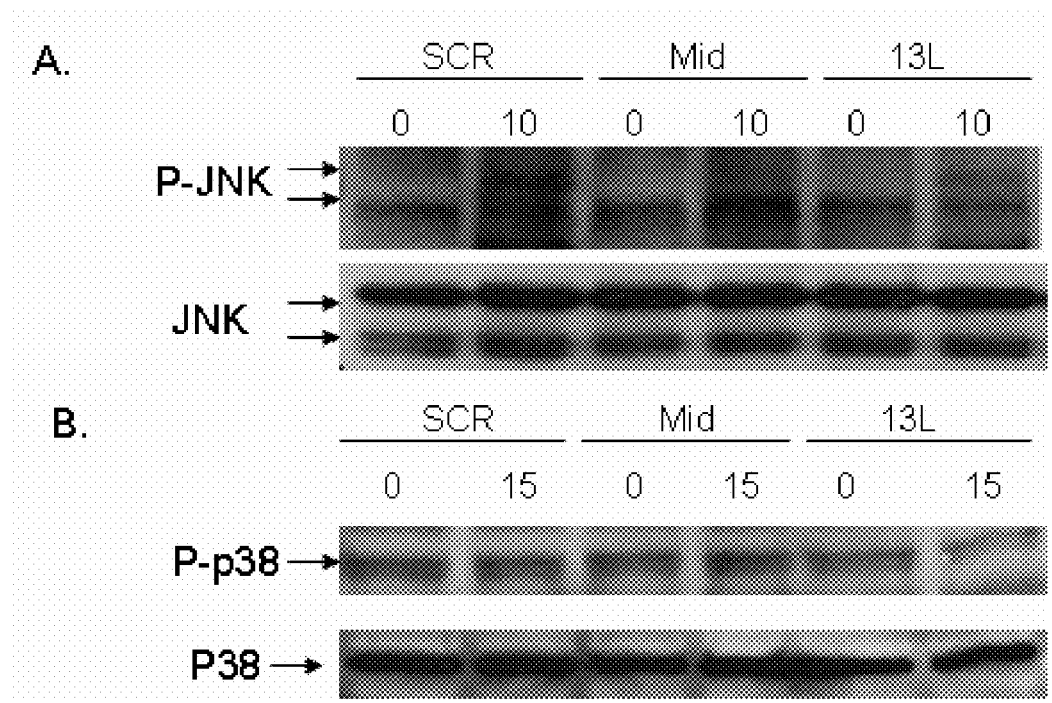
FIG. 22 shows that IG20-SVs do not affect TNF-α induced activation of other MAP kinases like JNK and p38. (A)&(B) TNF-α induced JNK and p38 phosphorylation in HeLa. HeLa cells ($3 \times 10^6$ per 100 mm dish) were transduced with different lentiviruses expressing SCR, Mid and 13L ShRNA for 48 h. The cells were then serum starved for 6 h and were either left unstimulated or stimulated with TNF-α (50 ng/mL) for 15 min. Cell lysates were analyzed for phosphorylated JNK and total JNK (A) or phosphorylated-p38 and p38 (B) by immunoblot. The data presented is representative of at least 3 independent experiments.
Figure 23:
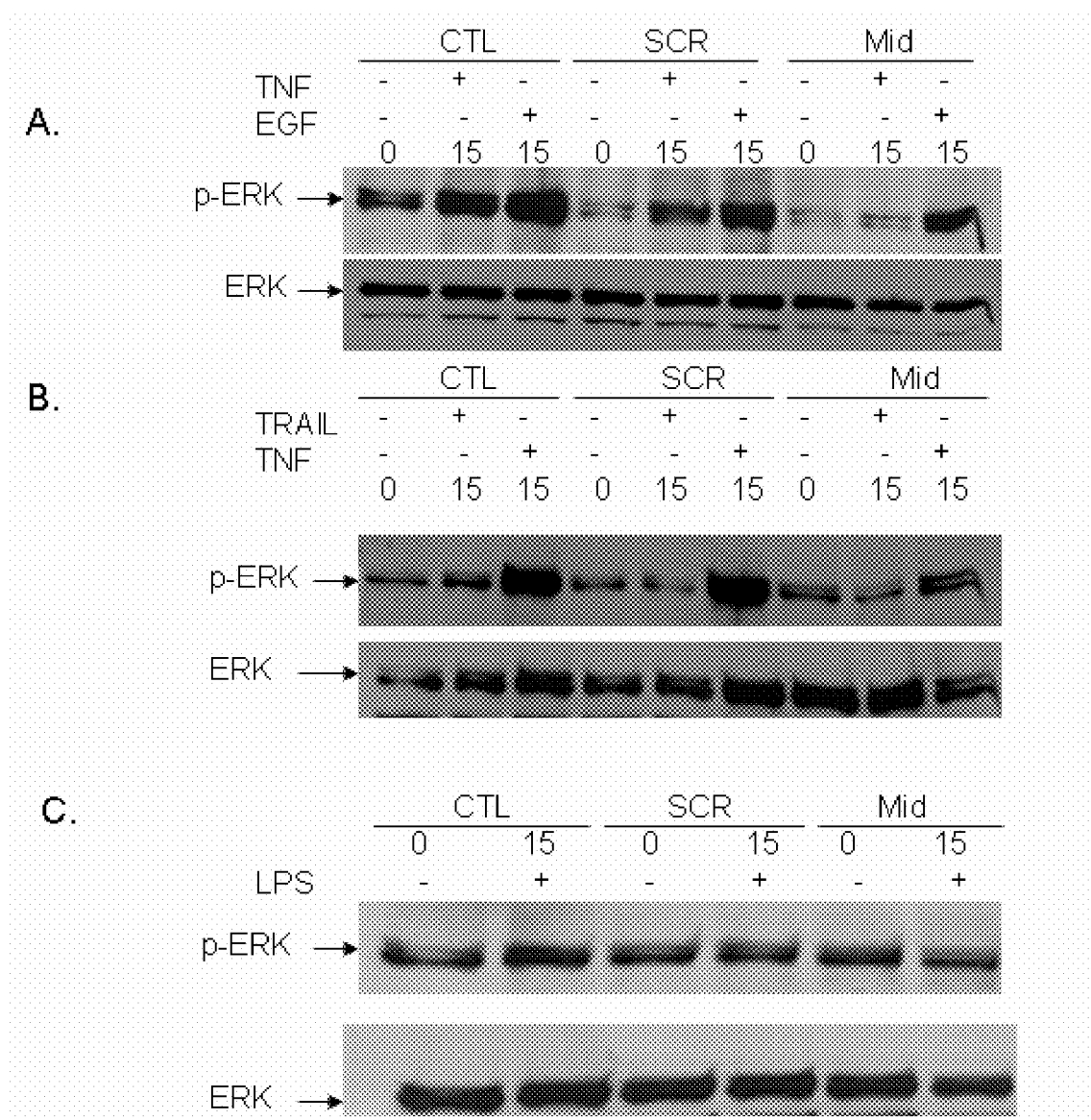
FIG. 23 shows that IG20 gene knock down has no role in EGF, TRAIL or LPS mediated ERK phosphorylation. (A), (B) & (C) HeLa cells ($3 \times 10^6$ per 100 mm dish) were transduced with different lentiviruses expressing SCR and Mid ShRNA for 48 h. The cells were then serum starved for 6 h and were either left unstimulated or stimulated with (A) 100 ng/mL EGF or 50 ng/mL TNF-α for 15 min, (B) 250 ng/mL TRAIL or 50 ng/mL TNF-α for 15 min or (C) 1 μg/mL LPS for 15 min. Cell lysates were analyzed for phosphorylated ERK and total ERK by immunoblot. The data are representative of at least 3 independent experiments.
Figure 24:
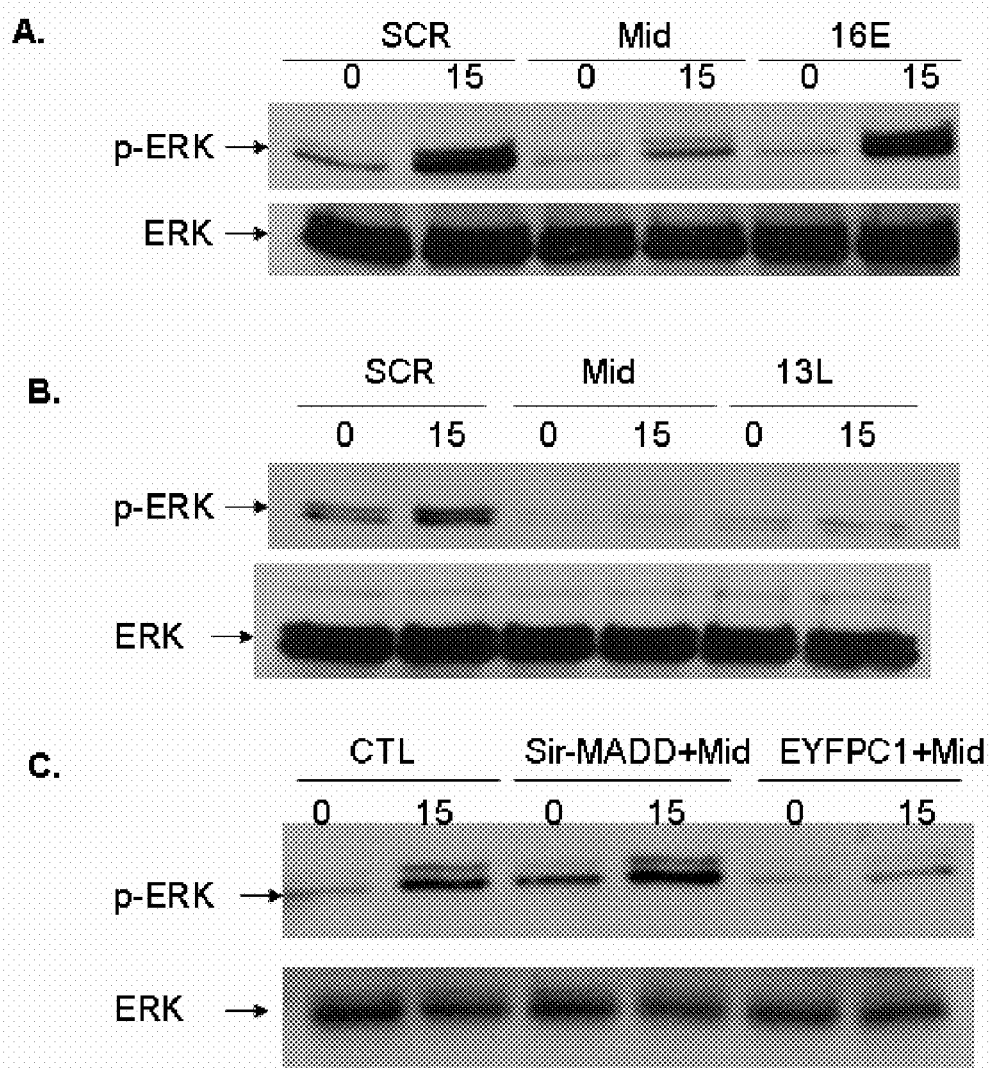
FIG. 24 shows that MADD-SV is essential for TNF-α induced ERK activation. (A) HeLa cells ($3 \times 10^6$ per 100 mm dish) were transduced with different lentiviruses expressing SCR, Mid and 16E ShRNA for 48 h. The cells were then serum starved for 6 h and were either left untreated or treated with TNF-α (50 ng/mL) for 15 min. Cell lysates were analyzed for phosphorylated ERK or total ERK by immunoblot. (B) PA-1 cells ($5 \times 10^6$ per 100 mm dish) were transduced with different lentiviruses expressing SCR, Mid and 13L ShRNA for 48 h. The cells were then serum starved for 6 h and were either left unstimulated or stimulated with TNF-α (50 ng/mL) for 15 min. Cell lysates were analyzed for phosphorylated ERK or total ERK by immunoblot. (C) HeLa cells ($3 \times 10^5$ per 60 mm dish) were either left untransfected or transfected with either SirMADD or EYFPC1 plasmids. Twenty-four hours post-transfection, the cells were infected with Mid ShRNA. Forty-eight hours post transduction, the cells were either left unstimulated or stimulated with TNF-α (50 ng/mL) for 15 min. Cell lysates were analyzed for phosphorylated ERK or total ERK by immunoblot. The data presented is representative of at least 3 independent experiments.

The four IG20-SVs (IG20pa, MADD-SV, IG20-SV2 and DENN-SV) show a very high degree of sequence homology and can only be differentiated by the differential splicing of exons 13L (130 base pairs) and 16E (60 base pairs). Hence delineating the roles of individual isoforms of IG20 is often difficult. This intricate task of identifying which IG20 isoform is critical for TNF-α induced ERK activation was undertaken by taking advantage of the differential splicing of exons 13L and 16E and the post-transcriptional sequence-specific mode of action of ShRNA which can down-modulate all or specific combination of IG20 isoforms. The knock-down of all IG20-SVs (FIGS. 20C, 24 (A&B) or MADD-SV along with IG20pa (FIG. 20C) in HeLa or knockdown of MADD-SV alone sparing DENN-SV in PA-1 cells (FIG. 24B) have resulted in a substantial decrease in TNF-α induced ERK phosphorylation. Sparing of MADD-SV along with DENN-SV (FIG. 24A) or over-expression of Mid ShRNA resistant MADD followed by the knockdown of all endogenous IG20 isoforms have resulted in considerable ERK phosphorylation compared to un-transduced or vector control (SCR) in HeLa cells (FIG. 24C). Also, the role of MADD-SV was found to be highly specific to TNF-α induced ERK activation. It is not involved in the activation of other MAP kinases like JNK or p38 (FIG. 22) or activation of ERK1/2 by growth factors (FIG. 23A). These results demonstrate that MADD-SV plays an essential role in TNF-α induced ERK activation and down-modulation of endogenous MADD-SV alone is necessary and sufficient to abrogate TNF-α induced ERK phosphorylation.

Figure 25:
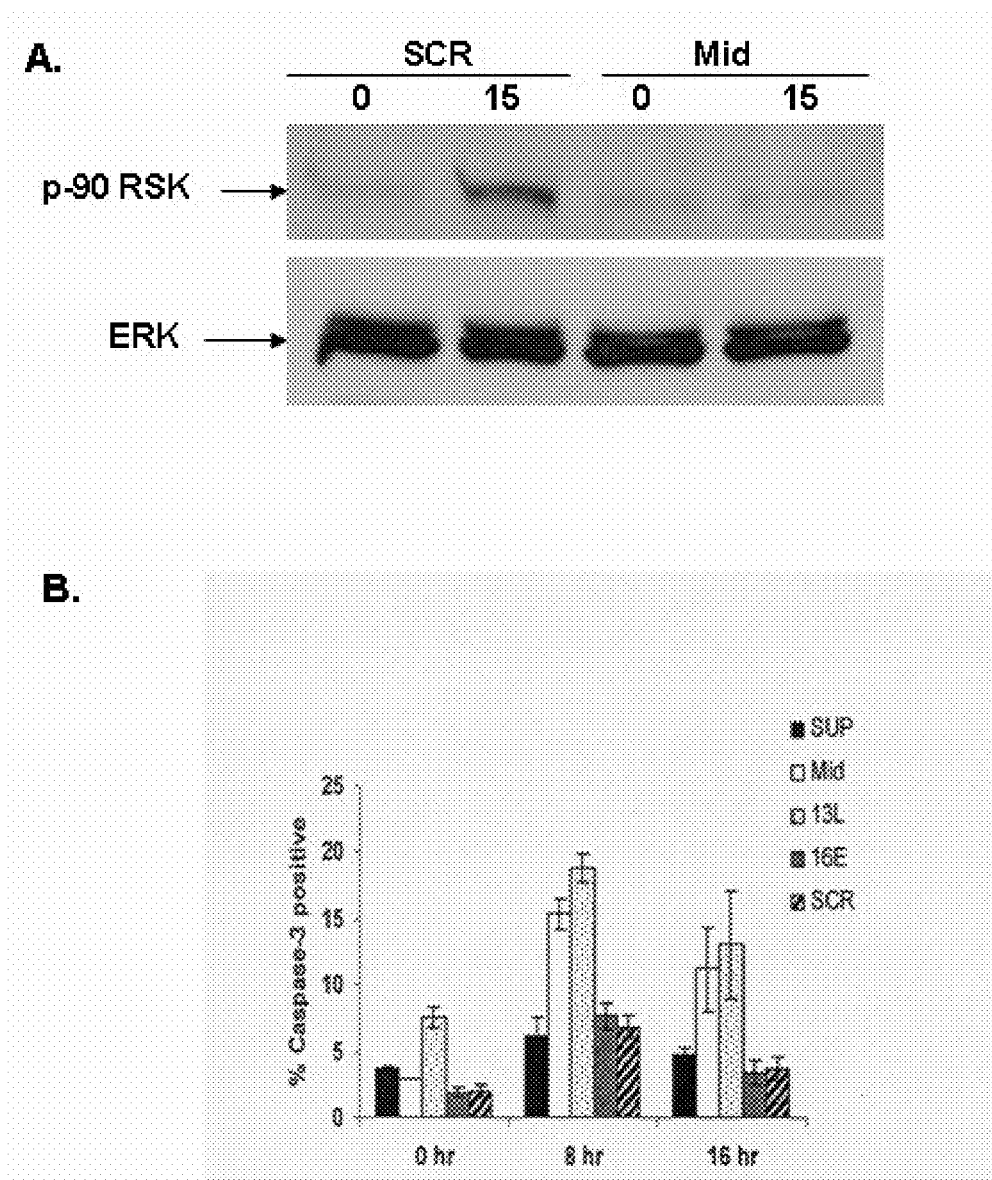
FIG. 25 shows that down-modulation of MADD-SV impair p90RSK phosphorylation and sensitizes cells to undergo apoptosis. (A) HeLa cells ($3 \times 10^6$ per 100 mm dish) were transduced with different lentiviruses expressing SCR and Mid ShRNA for 48 h. The cells were then serum starved for 6 h and were either left untreated or treated with TNF-α (50 ng/mL) for 15 min. Cell lysates were analyzed for phosphorylated p90RSK or total ERK by immunoblot. (B) Thirty-six hours post-transduction, HeLa cells were treated with 50 ng/mL of TNF-α for 8 h and 16 h respectively and active caspase-3 was detected by FACS.

The effects of down-modulation of IG20-SVs esp. MADD-SV were analyzed on the phosphorylation of the down-stream substrate of ERK like p90RSK. The kinase, p90RSK upon phosphorylation by ERK1/2, with which it is physically associated in the cytoplasm, translocates to the nucleus and activates transcriptional factors like CREB and c-FOS which play a critical role in cancer cell growth, differentiation and development. The down-modulation of MADD-SV has resulted in near complete absence of p90RSK phosphorylation (FIG. 25A). Hence down-modulation of MADD-SV can be exploited as a strategy to control cancer cell growth mediated by down-stream substrates of ERK. Also, down-modulation of MADD-SV alone has sensitized the cells to undergo apoptosis upon TNF-α stimulation as evidenced by enhanced caspase-3 activation (FIG. 25B).

TNF-α does not induce apoptosis by default but is known to cause apoptosis when the survival pathway is inhibited (for instance by addition of protein synthesis inhibitor like cycloheximide). Down-modulation of MADD-SV alone was sufficient to render HeLa cells susceptible to TNF-α induced apoptosis in the absence of inhibition of transcription/translation of pro-survival factors.

Two major problems of cancer chemotherapy are toxicity to normal cells and failure to kill cancer cells. The damage is caused to both normal and cancer cells, and this damage is then passed through multiple steps into cell death, likely through activation of caspases and apoptosis. When these steps are compromised by antiapoptotic events, such as p53 mutation or overexpression of Bcl-2, the therapy fails. An alternative strategy is to design a treatment that activation caspases directly by activating the death receptor complexes, resulting in activation of their corresponding initiator caspases like caspase-8. Down-modulation of MADD-SV of the IG20 gene provides a tool for molecular targeted therapies. First, down-modulation of MADD-SV does not after the growth of normal cells since it is a protein over-expressed in cancer cells and plays a prominent role only in cancer cell growth. Second, down-modulation of endogenous MADD-SV abrogates ERK1/2 phosphorylation and prevents the cancer growth mediated by TNF-α induced ERK MAP kinase activation. Third, down-modulation of MADD-SV alone is sufficient to directly activate caspase-8 and subsequently the effector caspase-3 upon TNF-α stimulation and thereby promote apoptosis of cancer cells. Down-modulation of endogenous MADD-SV works like a double-edged weapon in preventing cancer growth mediated by TNF-α induced ERK activation. In one way it abrogates pro-survival ERK activation and in other way it activates caspases and brings about apoptosis.

Specific down-regulation of MADD splice variant or inhibition of its activity is also possible by agents such as a small molecule, a peptide nucleic acid, an antibody, inhibitor compound, and synthetic nucleic acids that specifically bind to RNA. RNA/DNA hybrids and down-regulate MADD isoform expression.

Nucleic acid or nucleic acid sequence or polynucleotide or polynucleotide sequence refers to the sequence of a single- or double-stranded DNA or RNA molecule of genomic or synthetic origin, i.e., a polymer of deoxyribonucleotide or ribonucleotide bases, respectively.

An isolated nucleic acid sequence is substantially separated or purified from other nucleic acid sequences with which the nucleic acid is normally associated in the cell of the organism in which the nucleic acid naturally occurs. The term includes nucleic acids that are biochemically purified so as to substantially remove contaminating nucleic acids and other cellular components. The term also includes recombinant nucleic acids and chemically synthesized nucleic acids. The term "substantially purified", as used herein, refers to a molecule separated from other molecules normally associated with it in its native state. For example, a substantially purified molecule is the predominant species present in a preparation, such as, isolated BTI nucleic acid after a PCR. In one embodiment, a siRNA molecule includes a double stranded RNA wherein one strand of the RNA is complimentary to the RNA of MADD splice variant. In another embodiment, a siRNA molecule of the invention includes a double stranded RNA wherein one strand of the RNA comprises a portion of a sequence of RNA having MADD or IG20 gene splice variant sequence. In another embodiment, a siRNA molecule includes a double stranded RNA wherein both strands of RNA are connected by a non-nucleotide linker. Alternately, a siRNA molecule includes a double stranded RNA wherein both strands of RNA are connected by a nucleotide linker, such as a loop or stem loop structure.

Short hairpin RNA (shRNA) contains complementary sense and antisense sequences of a target gene linked by a loop structure. The target sequence starts as a dsDNA cloned into an expression vector that is transcribed to form an shRNA. In the cytoplasm, shRNA is cleaved by Dicer generating short sequences of RNA that can inhibit gene expression by RNAi. The benefit to shRNA is stable transfection of cell lines and enables a single gene in each cell to be targeted. To construct shRNA vectors, see McIntyre and Fanning (2006), Design and cloning strategies for constructing shRNA expression vectors, *BMC Biotechnol.* 2006; 6: 1, incorporated herein by reference in its entirety.

In one embodiment, a single strand component of a siRNA molecule is from about 14 to about 50 nucleotides in length. In another embodiment, a single strand component of a siRNA molecule is about 15-20, 15-21, 14-25, 16-30 or 20-25 nucleotides in length. In yet another embodiment, a single strand component of a siRNA molecule is about 23 nucleotides in length. In one embodiment, a siRNA molecule is from about 20 to about 40 nucleotides in length.

In an embodiment, an antisense nucleic acid molecule, decoy RNA, dsRNA, siRNA, shRNA, or aptamer, nucleic acids include at least one nucleic acid base modification.

In another embodiment, an antisense nucleic acid molecule, decoy RNA, dsRNA, siRNA, shRNA, or aptamer, nucleic acids of the invention comprises at least one phosphate backbone modification.

Methods for treatment of cancer are described wherein cancer includes for example breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancer, comprising administering to a subject, a nucleic acid molecule or antisense nucleic acid molecule or other nucleic acid molecule capable of down-regulating MADD expression or other splice variant of IG20 gene under conditions suitable for said treatment. Any cancer cell that expresses one or more of the IG20 splice variants including MADD is suitable for cancer therapeutics using the compositions disclosed herein.

In another embodiment, conventional or other known drug therapies to be used along with the down-regulation of MADD or prior to or after MADD down-regulation include monoclonal antibodies, specific inhibitors, chemotherapy, or radiation therapy or a combination thereof for cancer.

Specific chemotherapy include paclitaxel, docetaxel, cisplatin, methotrexate, cyclophosphamide, 5-fluoro uridine, Leucovorin, Irinotecan (CAMPTOSAR™ or CPT-11 or Camptothecin-11 or Campto), Paclitaxel, Carboplatin, doxorubicin, fluorouracil carboplatin, edatrexate, gemcitabine, or vinorelbine or a combination thereof can be administered along with agents capable of down-regulating MADD or prior to or after down-regulation of MADD.

Antisense nucleic acid refers to a nucleic acid molecule that binds to target RNA by means of RNA-RNA or RNA-DNA or RNA-PNA (peptide nucleic acid) interactions and alters the activity of the target RNA. Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

Double stranded RNA or dsRNA refers to a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression. The term "double stranded RNA" or "dsRNA" as used herein refers to a double stranded RNA molecule capable of RNA interference "RNAi", including short interfering RNA "siRNA".

Splice variant refers to a specific isoform of IG20 gene that is expressed in one or more cell type by alternate splicing.

Consisting essentially of means that the nucleic acid molecule includes a nucleic acid sequence capable of down-regulating a specific splice variant of IG20 gene. Other sequences can be present which do not interfere with the activity.

In another aspect nucleic acid molecules or antisense molecules that interact with target RNA molecules and down-regulate MADD activity are expressed from transcription units inserted into DNA or RNA vectors. The recombinant vectors are preferably DNA plasmids or viral vectors. Enzymatic nucleic acid molecule or antisense expressing viral vectors can be constructed based on adeno-associated virus, retrovirus, adenovirus, or alphavirus. Preferably, the recombinant vectors capable of expressing the nucleic acid molecules are delivered as described herein, and persist in target cells. Alternatively, viral vectors can be used that provide for transient expression of shRNA/siRNA/anti-sense nucleic acid molecules. Such vectors can be repeatedly administered as necessary. After being expressed, the interfering nucleic acid molecules bind to the target RNA and down-regulate its function or expression. Delivery of nucleic acid molecule or antisense expressing vectors can be systemic, such as by intravenous or intramuscular administration, by administration to target cells explanted from the patient or subject followed by reintroduction into the patient or subject, or by any other means that would allow for introduction into the desired target cell. Antisense DNA can also be expressed via the use of a single stranded DNA intracellular expression vector.

In addition, the term "pharmaceutically effective amount" or "therapeutically effective amount" refers to an amount (dose) effective in reducing tumor growth or tumor size or cancer metastasis of a patient, having, for example, cancer. It is also to be understood herein that a "pharmaceutically effective amount" may be interpreted as an amount giving a desired therapeutic effect, either taken in one dose or in any dosage or route, taken alone or in combination with other therapeutic agents. In the case of the present disclosure that relates to down-regulation of IG20 splice variants, a "pharmaceutically effective amount" may be understood as an amount of shRNA or siRNA that specifically down-regulates one or more of the IG20 splice variants including MADD which may for example, suppress (e.g., totally or partially) the expression of IG20 splice variants. The dose may be of any suitable form.

Nucleic acid molecules can be administered to cells by a variety of methods known to those familiar to the art, including, but not limited to, encapsulation in liposomes, by iontophoresis, or by an incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other approaches include the use of various transport and carrier systems, for example, through the use of conjugates and biodegradable polymers.

The molecules disclosed herein can be used as pharmaceutical agents. Pharmaceutical agents prevent, inhibit the occurrence, or treat (alleviate a symptom to some extent, preferably all of the symptoms) of a disease state in a subject.

The negatively charged polynucleotides can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions can also be formulated and used as tablets, capsules or elixirs for oral administration; suppositories for rectal administration; sterile solutions; suspensions for injectable administration; and the other compositions known in the art.

Pharmaceutically acceptable formulations of the compounds are described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Systemic administration refers to in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue, e.g., tumor tissue. The use of a liposome or other drug carrier comprising the compounds of the instant invention can potentially localize the drug, for example, in certain tissue types. A liposome formulation which can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

The nucleic acid molecules disclosed herein and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule and a pharmaceutically acceptable carrier. One or more nucleic acid molecules can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs. Pharmaceutical compositions that consist essentially of the nucleic acid sequences to knock-down a specific IG20 splice variant may include about 0.1 µg to 1 mg of nucleic acid per kg of body weight. Variations in dosage and effects can be optimized using skills known to a skilled artisan.

In another aspect nucleic acid molecules include an expression vector that includes nucleic acid sequence encoding at least one of the nucleic acid molecules, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein the sequence is operably linked to said initiation region and said termination region, in a manner which allows expression and/or delivery of said nucleic acid molecule.

EXAMPLES

The following examples are to be considered as exemplary and not restrictive or limiting in character and that all changes and modifications that come within the spirit of the disclosure are desired to be protected.

Example 1 siRNAs can Selectively Knock-Down Expression of Exogenous IG20-SVs

Figure 9:
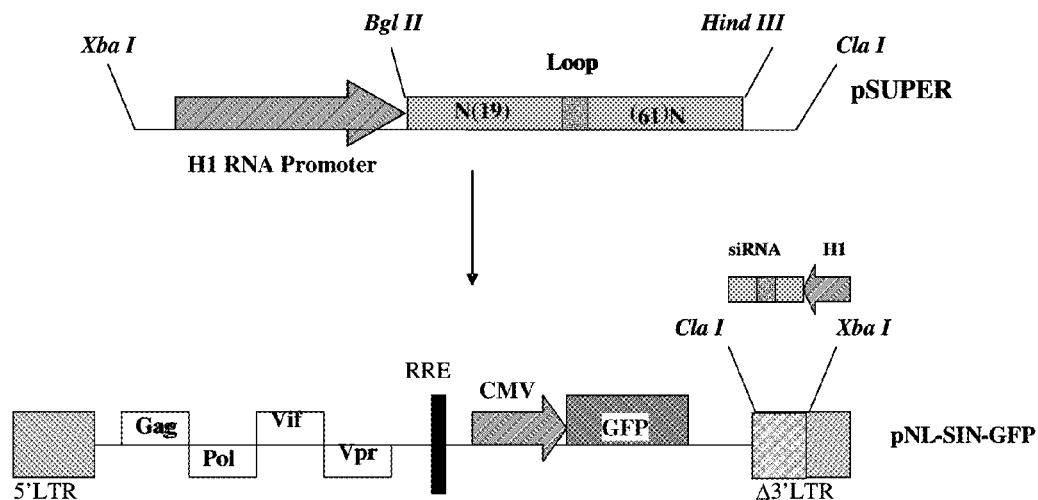
FIG. 9 is an illustration of a shRNA vector used herein that is capable of stable expression of shRNAs.

In order to determine which of the IG20-SVs contribute to apoptosis and cell proliferation, siRNA (small inhibitory RNA) approach was used to selectively knockdown IG20-SVs (Table 1). The siRNAs were cloned into the pSUPER vector to allow for expression of shRNAs (small hairpin RNAs). An aspect of such a vector is shown in FIG. 9. 293T cells were co-transfected with YFPIG20pa, YFP-MADD or YFP-DENN-SV along with different shRNA-expressing pSUPER vectors at ratios of 1:1, 1:3 and 1:7. Knock-down of protein expression was assessed by a reduction in YFP expression using flow cytometry. Several shRNAs were screened. Knock-down of expression of exogenous IG20-SVs were analyzed. 293T cells were plated onto 12-well plates and cotransfected with the indicated IG20-SV-YFP and pSUPER-shRNA constructs. YFP expression was represented as Mean Fluorescence Intensity. Specificity of Mid-shRNA was analyzed. The inability of Mid-shRNA to suppress the expression of mutant-IG20pa, -MADD, and -DENN-SV constructs was analyzed. The 13L-shRNA that targets exon 13L down-modulated IG20pa/MADD, leaving the expression of IG20-SV2 and DENN-SV unaltered was studied. In contrast, 16E-shRNA that targets exon 16, down-modulated IG20pa/IG20-SV2, but not MADD and DENN-SV. The Mid-shRNA targeted at exon 15 down-modulated all IG20-SVs. Vector alone or a control shRNA had little or no effect on the expression of IG20-SVs. The sequences provided in Table 1 are exemplary and other sequences that specifically target MADD or any other isoform can be designed by those of skill in the art based on the information given in Table 1 and the disclosure in general.

Figure 11:
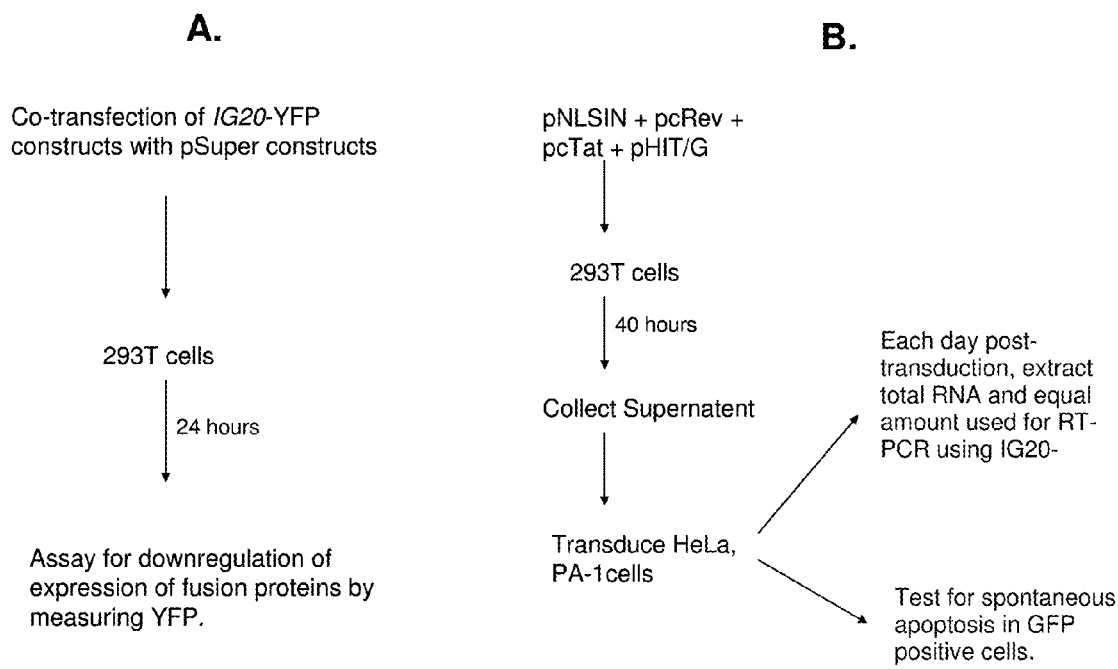
FIG. 11 provides schematic illustration of screening for shRNAs (A) and lentivirus production that contain the shRNA expressing vectors (B).
Figure 12:
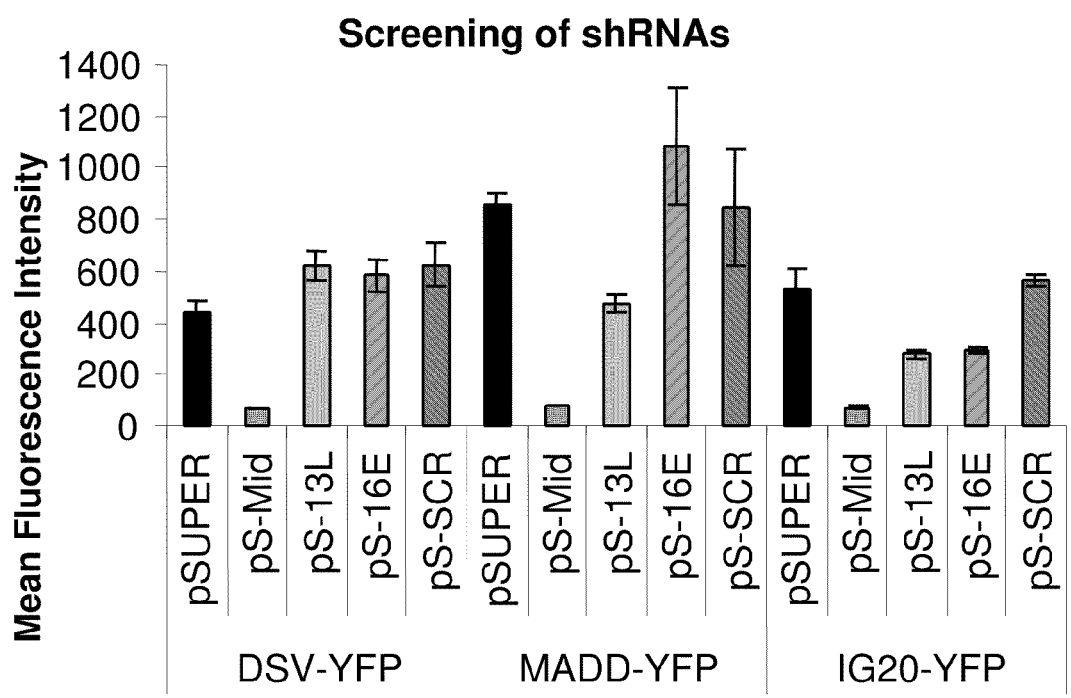
FIG. 12 is a chart demonstrating the knock-down effects of the respective shRNAs directed against IG20 splice variants, as measured by mean fluorescent intensity.
Figure 18:
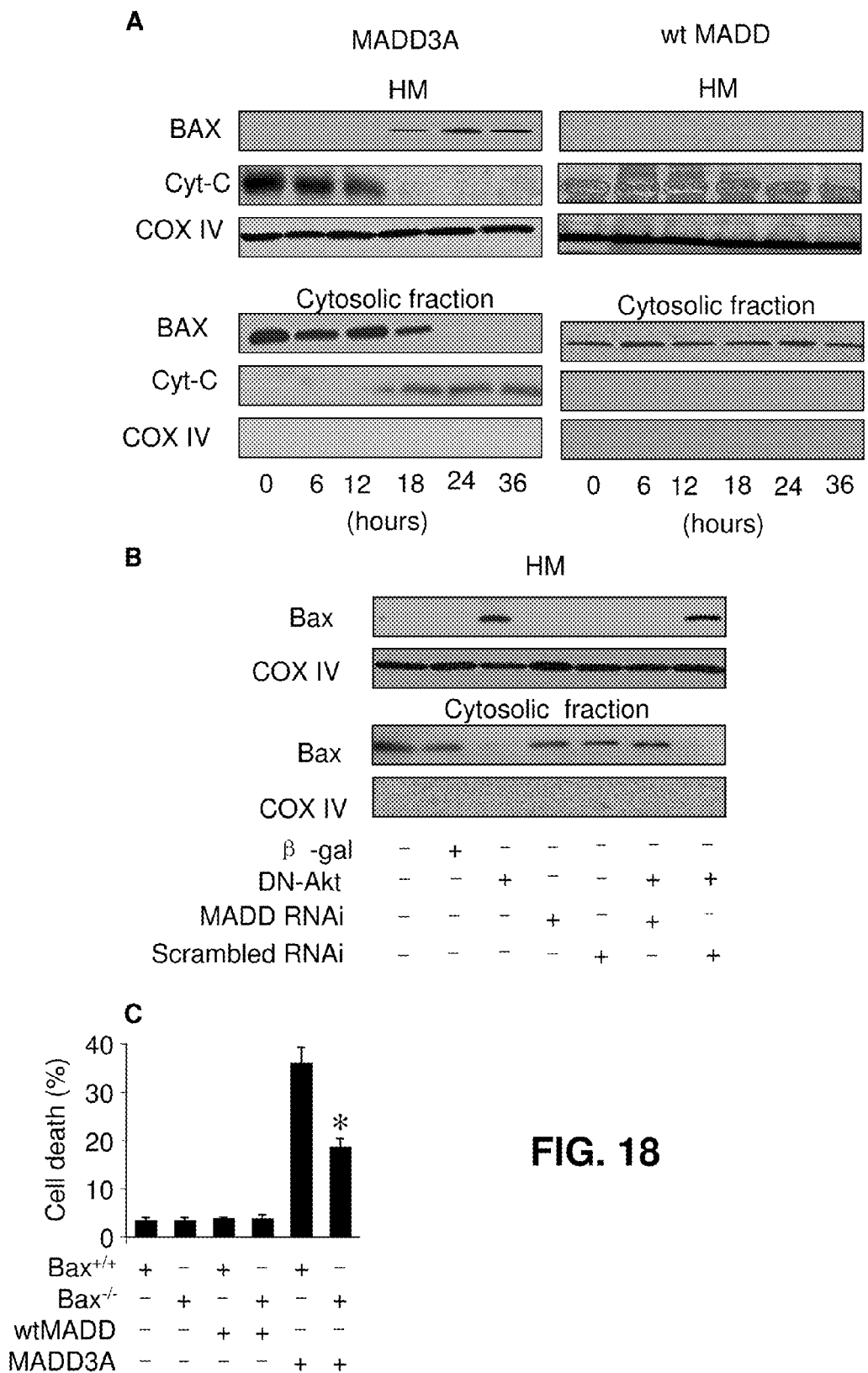
FIG. 18 demonstrates that nonphosphorylated MADD triggers Bax translocation to the mitochondria. (A) MADD3A but not wtMADD is able to induce Bax translocation and cytochrome c release. HEK293 cells were transfected with MADD3A or wtMADD. The distributions of Bax and cytochrome c in mitochondria-enriched heavy membrane (HM) and cytosolic fractions were analyzed by immunoblotting using antibodies against Bax or cytochrome c. COX IV served as a mitochondrial marker. (B) Endogenous MADD is required for Bax translocation. HeLa cells were transduced with β-galactosidase (β-gal), DN-Akt, MADD shRNA or scrambled shRNA and 24 h later the cells were harvested and Bax distributions in mitochondria and cytosol was determined by immunoblotting using an anti-Bax antibody. (C) Bax can mediate the death signal of MADD3A. HCT116Bax$^{-/-}$ and HCT116Bax$^{+/+}$ cells were transfected with cDNAs encoding wtMADD or MADD3A, and 48 h later the cell death was determined by Trypan Blue exclusion. *p<0.05 vs Bax$^{+/+}$+MADD3A.

The 13L- or 16E-shRNAs were highly specific and had little or no effect on IG20-SVs devoid of the targeted exon. To further confirm specificity of Mid-shRNA, silent mutations were created in cDNAs encoding IG20-SVs at sites corresponding to the $5^{th}$, $7^{th}$, $11^{th}$ and $14^{th}$ nucleotides of the Mid-shRNA. These mutations neither affected the amino acid sequence nor protein expression. Mutant-IG20-SV constructs were cotransfected with the pSUPER-shRNA and assessed for their expression. Mid-shRNA failed to down-modulate the mutant-proteins (FIG. 1B) further indicating the high specificity of the shRNA to the intended target. FIG. 18 is a schematic illustration of the targets of some of the shRNAs used to knock-down specific IG20 splice variants (isoforms). FIG. 11 provides schematic illustration of screening for shRNAs (A) and lentivirus production that contain the shRNA expressing vectors (B). Fluorescence values were measured from cells transfected with the respective shRNAs (FIG. 12).

Example 2 shRNAs Effectively Knock-Down Endogenous IG20-SVs

The shRNAs described herein were cloned into a self-inactivating lentivirus vector (pNL-SINGFP) and generated SUP (vector control), Mid, 13L, 16E and SCR (negative control shRNA) constructs to target specific combinations of endogenous IG20-SVs. An illustration of such a vector is shown in FIG. 9. This enabled identification of expression of double copy cassettes likely resulting in enhanced silencing.

Differential down-modulation of endogenous IG20-SVs in HeLa cells was analyzed. 1 µg total RNA obtained from HeLa cells at 72 hours post-transduction was used for RT-PCR. The products were separated on a 2% agarose gel. Amplification of all four IG20-SVs using F2-B2 primers was performed. Amplification of IG20pa and MADD using 13L-Forward and B2-Reverse primers was performed. The transduction efficiency was over 80% as determined by GFP expression. Relative to controls (SUP and SCR), HeLa cells expressing Mid-shRNA showed decrease in all IG20-SVs. While, 13L-shRNA caused near complete abrogation of only IG20pa and MADD, 16E-shRNA decreased expression of only IG20pa and IG20-SV2, without affecting the expression of the other variants. This was confirmed using 13L-forward and B2-reverse primers, and F2-forward and 16E-reverse primers, that amplify only IG20pa and MADD, and not DENN-SV. The effects of loss of various endogenous IG20-SV transcripts on the ability of cancer cells to survive were investigated.

Example 3

Down-Modulation of IG20-SVs in HeLa Cells Leads to Spontaneous Apoptosis

Spontaneous cell death was determined by nuclear condensation (Hoechst 33342) and loss of mitochondrial membrane potential (TMRM staining) (FIG. 1A-B). Down-modulation of all IG20-SVs using the Mid-shRNA resulted in significant spontaneous apoptosis. While down-modulation of IG20pa and IG20-SV2 had no effect, abrogation of MADD and IG20pa led to increased spontaneous apoptosis similar to the levels observed in Mid-shRNA expressing HeLa cells.

Whether the underlying cause of increased spontaneous apoptosis was similar to that noted after induction of apoptosis by the extrinsic (caspase-8 activation) or the intrinsic (caspase-9 activation) pathway was analyzed by determining the percentage of cells that harbored active caspases 8 and 9 using flow cytometry.

Example 4

Abrogation of MADD and IG20pa Leads to Increased Caspase Activation

Using a pan-caspase inhibitor, a general increase in caspase activation was observed in cells that had reduced MADD expression (FIG. 2A). Increased levels of both active-caspases-8 and -9 were detected in cells treated with either Mid- or 13LshRNA as early as 60 hours (FIGS. 4B and C), and peaked 72 hours, post-shRNA transduction; indicating activation of both extrinsic and intrinsic apoptotic pathways in cells lacking MADD.

Example 5

Down-Modulation of IG20-SVs has no Apparent Effect on HeLa Cell Proliferation In order to assess the effects on cell growth and proliferation, various shRNA-expressing viable cells were counted. Relative to controls, a significant decrease in the numbers of viable cells expressing Mid- and 13L-shRNA was observed (FIG. 3). The cells were stained with CFSE and cell division was monitored. Lack of difference in CFSE-dilution with time between the control, Mid- and 13L-shRNA treated cells indicated that the differences in cell numbers were not due to decreased proliferation but spontaneous cell death. Further confirmation was obtained by plating equal numbers of HeLa cells expressing various shRNAs and determining the number and size of colonies after 12 days. Although significantly fewer colonies were formed by Mid- and 13LshRNA expressing cells, the size of the colonies however were comparable to that of controls. Further, cell cycle analysis of shRNA-treated cells failed to show significant differences and indicated that the primary effect of MADD abrogation is spontaneous apoptosis.

Example 6

MADD Knock-Down in PA-1 Ovarian Carcinoma Cells Results in Spontaneous Apoptosis In HeLa cells, down-modulation of all four, or a combination of IG20pa/MADD or IG20pa/IG20-SV2 variants was demonstrated. To unequivocally demonstrate that MADD is required for cell survival, PA-1 ovarian carcinoma cells were used that essentially express only MADD and DENN-SV and thereby facilitate exclusive down-modulation of MADD. The effects of IG20 down-modulation in PA-1 cells were analyzed. Down-modulation of endogenous IG20 in PA-1 cells was analyzed. RT-PCR of IG20-SVs using F2-B2 primers from PA-1 cells 72 hours post-transduction was performed. Amplification of only IG20pa and MADD using 13L-F and B2 primers was performed. Nuclear Condensation was also determined. 72 hours post-transduction, PA-1 cells were stained with Hoechst stain and analyzed by FACS. Mitochondrial Depolarization was performed. 72 hours post transduction, PA-1 cells were stained with TMRM and analyzed by FACS.

While treatment with Mid-shRNA down modulated both MADD and DENN-SV, treatment with 13L-shRNA abrogated only MADD expression. Further confirmation was obtained by using a different set of primers to amplify MADD and IG20pa. Seventy two hours post-transduction with 13L-shRNA 50% of the cells underwent spontaneous apoptosis.

Figure 4:
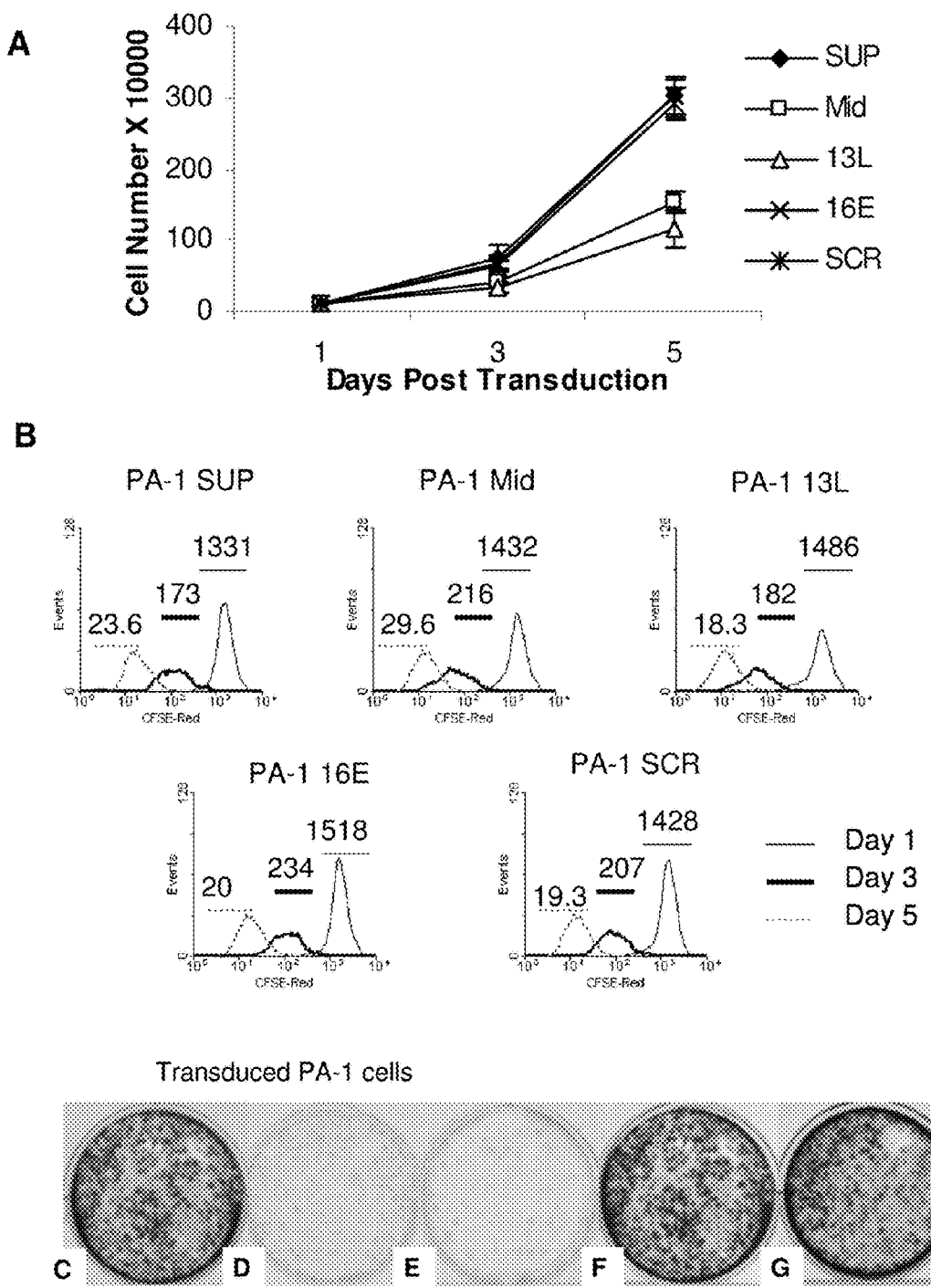
FIG. 4 shows effects of IG20 down-modulation on PA-1 cell proliferation. (A) Cell Growth (B) Proliferation (C-G) Cell Survival. Experiments were carried out as described previously with HeLa cells (see FIG. 3 legend). Data shown are representative of three different experiments.

The ability of cells to proliferate was also determined. Equal numbers of PA-1 cells (24 hr post-transduction) were cultured and the number of viable cells determined at various time points (FIG. 4A). As seen in HeLa cells, loss of MADD resulted in a significant drop in cell numbers. There was, however, neither a significant difference in CFSE-dilution nor in the size of colonies (FIGS. 4B-G). These results clearly demonstrate that endogenous MADD protects cancer cells from spontaneous apoptosis; however, it does not affect their ability to proliferate.

Example 7

MADD Abrogation Results in Spontaneous as well as Enhanced TRAIL-Induced Apoptosis Without Affecting Expression of Death (DR) or Decoy Receptors (DcR), or Their Cognate Ligands Down modulation of IG20 transcripts upon treatment of cells with lentiviruses expressing different shRNAs was monitored by RT-PCR. The IC20 transcripts were significantly down-modulated by 24 h (FIGS. 5A, C). These cells were tested for spontaneous apoptosis at 72 h post-transduction by Hoechst staining (FIGS. 5B, D) or mitochondrial depolarization. Abrogation of MADD, but not other isoforms, resulted in spontaneous apoptosis.

Figure 6:
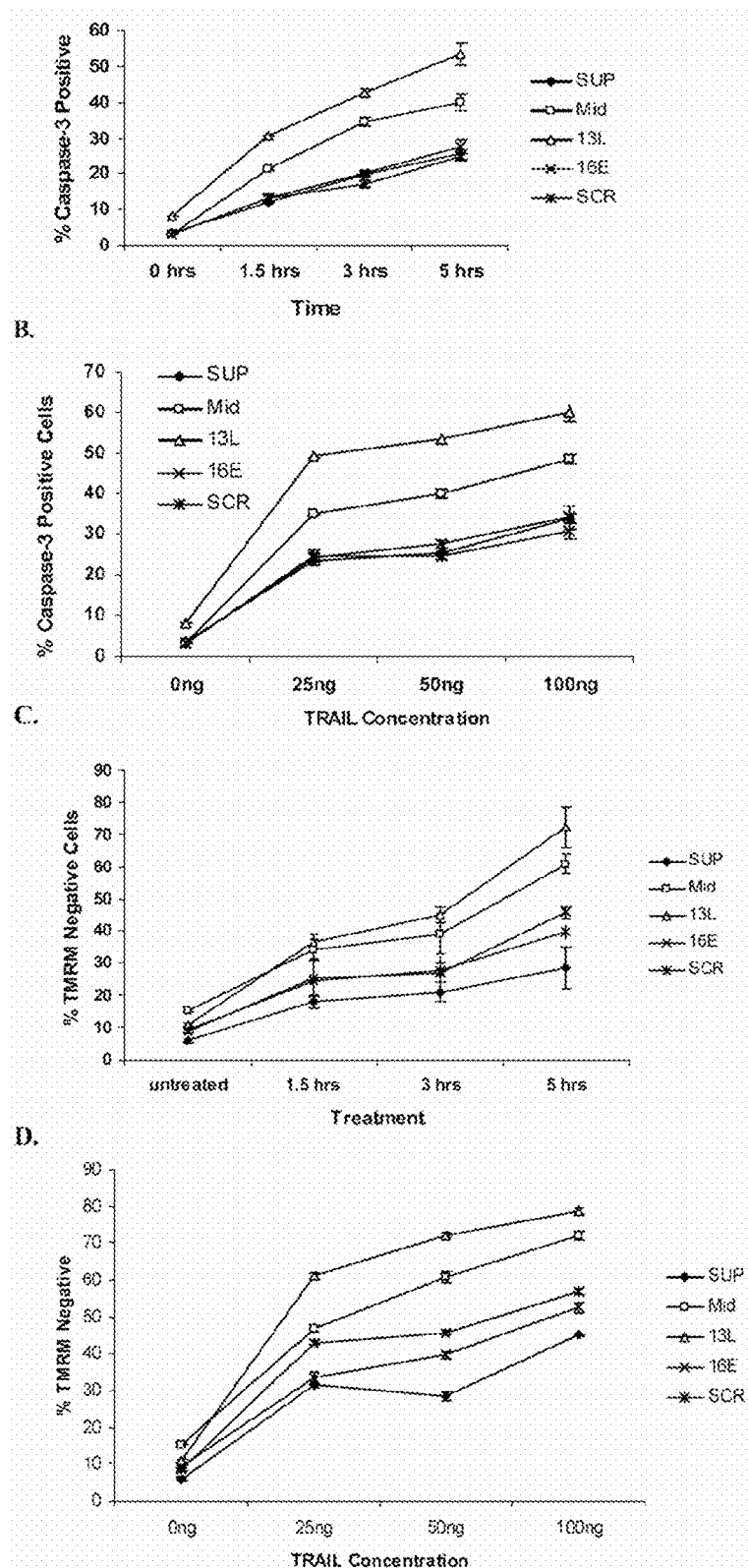
FIG. 6 represents down-modulation of MADD enhances susceptibility to TRAIL. Kinetics of response (A) and (C). Thirty-six hours post-transduction, HeLa cells were treated with 50 ng of TRAIL for different durations. Dose response (B) and (D). HeLa cells were treated for five hours with the indicated concentrations of TRAIL. (A and B) Active-caspase-3 was detected using a PE-conjugated antibody specific for active-caspase-3 by FACS. Data presented are representative of three different experiments and the P-value was <0.005. (C and D) Apoptosis was also measured by TMRM exclusion using FACS. Data shown represent mean±SD of triplicates.

Although the IG20 transcripts are significantly down-modulated by 24 hrs, the cells do not undergo spontaneous apoptosis until 72 hours post shRNA induction. This is most likely due to the time required for complete degradation of the remaining endogenous proteins. Therefore, at thirty-six hours post-shRNA transduction when there is no indication of spontaneous apoptosis, HeLa cells were treated with various concentrations of TRAIL for different durations and assayed for apoptosis. Cells devoid of MADD showed enhanced TRAIL-induced apoptosis as indicated by significant increases in caspase-3 activation (FIGS. 6A, B) and mitochondrial depolarization (FIGS. 6C, D). Similar results were obtained in PA-1 ovarian carcinoma cells.

Since increases in the levels of expression of DRs and their ligands, or decreases in DcRs can result in oligomerization of death receptors followed by apoptotic cell death, the levels of their expression in HeLa and PA-1 cells were tested. No significant difference in the levels of expression in various sh-RNA transduced cells relative to control cells was observed, and indicated that spontaneous apoptosis resulting from MADD down-modulation was not due to perturbations in the levels of DR4, DR5, Fas, FasL, TRAIL, DcR1 and DcR2 expression on the cell surface. Surface expression of DRs, DcRs, and their ligands are not altered upon MADD abrogation. HeLa cells transduced with the indicated shRNAs for 48 h were collected in enzyme-free cell dissociation buffer and stained with antibodies (specific to DR4, DR5, DcR1, DcR2, TRAIL, Fas and FasL or isotype controls) conjugated to PE.

Example 8

Down-Modulation of MADD Results in Activation of Caspase-8 at the DRs that can be Inhibited by DN-FADD and CrmA Only MADD-depleted HeLa and PA-1 cells (Mid and 13L cells) showed higher amounts of the intermediate activecaspase-8 proteins (p43/41). To gain insight into the mechanism underlying MADD-mediated cell survival, whether caspases were activated upon abrogation of MADD expression examined. HeLa cells and PA-1 cells were collected 48 h post-transduction and probed for caspase-8 and FADD, which are components of the DISC. As observed, the cleaved intermediate fragments of caspase-8 (early indication of caspase-8 activation) were detected only upon MADD abrogation, although the levels of pro-caspase-8, FADD, and actin were comparable in all cells. Only MADD-depleted HeLa and PA-1 cells (Mid and 13L cells) showed processing of pro-caspase-8 (p55/53), as indicated by the higher amounts of the intermediate active caspase-8 proteins (p43/41). Similarly, HeLa cells treated with 100 ng of TRAIL for different durations showed sustained caspase-8 activation and subsequent caspase-3 activation. TRAIL treatment results in recruitment of procaspase-8 to the receptors followed by its cleavage resulting in its activation. The cleaved intermediate fragments (p43/p41) and the catalytically active subunits of caspase-8 (p18) were detected upon TRAIL treatment. Caspase-8 is the initiator caspase that can cause activation of the effector caspase-3. A decrease in the amount of pro-caspase-3 indicates its cleavage to form active caspase-3 only in MADD-depleted cells. These results indicated that as early as 48 h after MADD abrogation, pro-caspase 8 (p55/53) is processed and cleaved into its intermediate (p43/41) active fragments. Similarly, HeLa cells treated with 100 ng of TRAIL for the indicated durations showed sustained caspase-8 activation and subsequent caspase-3 activation as evident from the increased levels of p43/p41 and p18 subunits of caspase-8, and a concomitant decrease in pro-caspase-3 levels only in MADD-depleted cells.

To more specifically analyze the DISC associated with TRAIL-bound death receptors, TRAIL-induced DISC was immunoprecipitated from HeLa cells using a biotinylated-antibody specific for TRAIL from HeLa cells that were either left untreated or treated with 250 ng of TRAIL for 30 min. Complexes were separated on 12% SDS-PAGE and subjected to immunoblotting with various antibodies that can specifically react with specific DISC components. Increased recruitment of FADD and pro-caspase-8 was observed after TRAIL treatment. Relative to control cells (SCR), TRAIL immunoprecipitates from MADD-depleted cells (13L and Mid) showed increased levels of intermediate fragments of caspase-8 (p43/41). However, increased caspase-8 activation (p43/41) was more apparent only upon MADD down-modulation.

Figure 7:
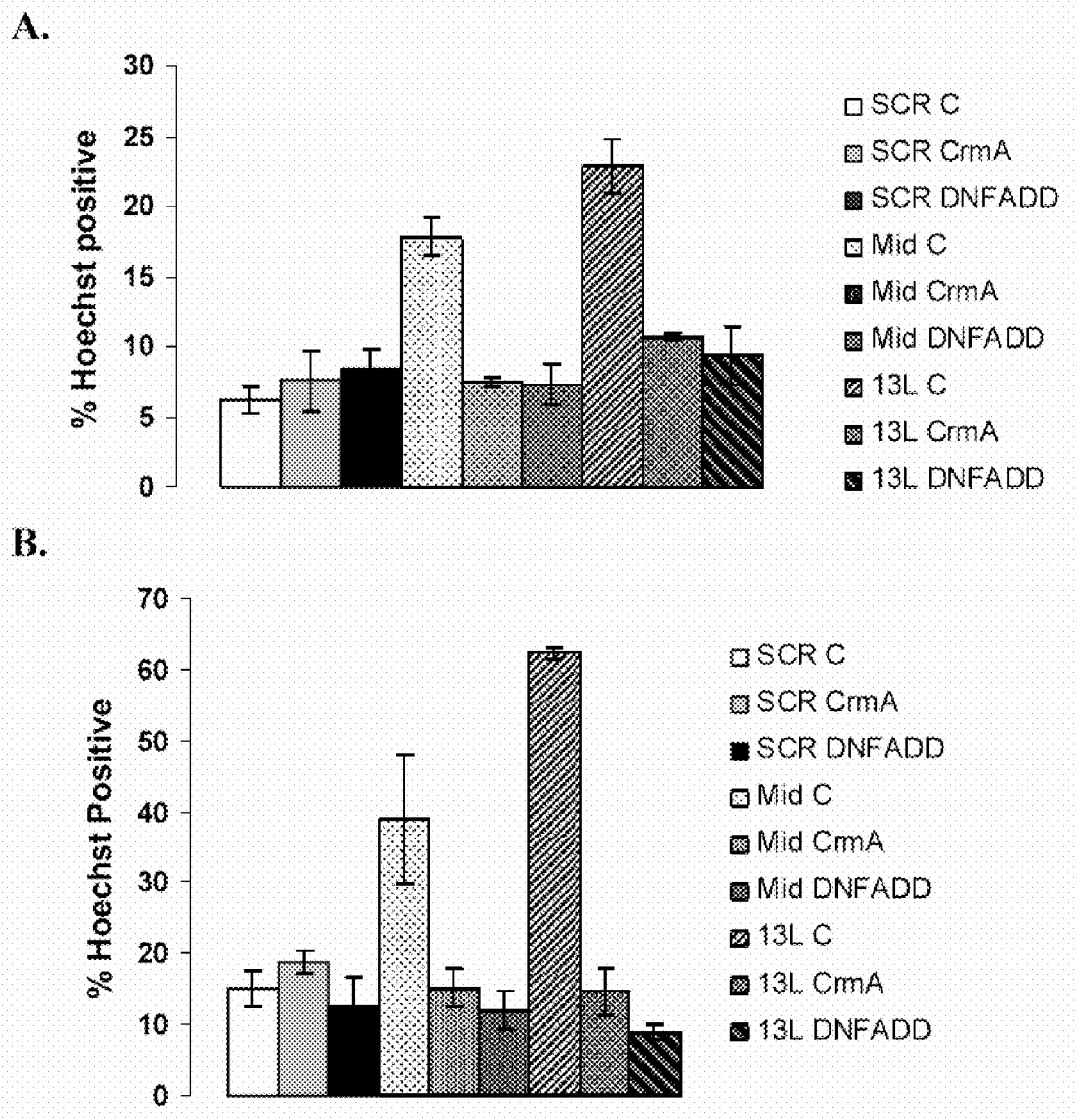
FIG. 7 shows that CrmA and DN-FADD inhibit the onset of spontaneous apoptosis. (A) HeLa and (B) PA-1 cells stably expressing control vector, CrmA or DN-FADD were transduced with SCR, Mid and 13L shRNAs. Spontaneous apoptosis was assessed by Hoechst staining 72 h post-transduction. Data shown are representative of three different experiments. P-value in each case was <0.005.
Figure 8:
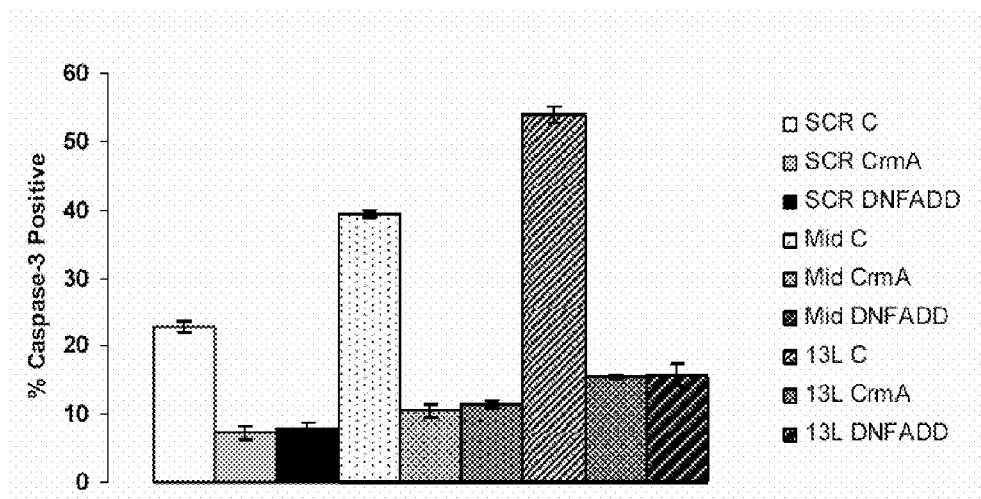
FIG. 8 shows DN-FADD and CrmA inhibit TRAIL-induced apoptosis. HeLa cells stably expressing control vector, CrmA or DN-FADD were transduced with SCR, Mid and 13L shRNAs. Thirty-six hours post-transduction, cells were treated with 50 ng of TRAIL for 5 hours. Apoptosis was measured by active-caspase-3 staining. Data shown are representative of three different experiments. Error bars indicate mean±SD of triplicates.

Further evidence in support of caspase-8 activation in apoptosis induced by MADD abrogation was gained from experiments carried out with HeLa and PA-1 cell lines stably expressing DN-FADD (Dominant-negative FADD) or CrmA. The spontaneous cell death that occurs due to abrogation of endogenous MADD is dramatically inhibited by both CrmA and DN-FADD. These inhibitors of DISC formation also rendered MADD-depleted HeLa cells (36 hours post-ShRNA transduction) resistant to TRAIL-induced apoptosis (FIGS. 7-8).

Since caspase-8 plays an essential role in receptor-mediated apoptosis that is characterized by DISC formation, the status of DISC in cells undergoing apoptosis due to loss of endogenous MADD expression was examined. DR4 and DR5 from HeLa and PA-1 cells respectively were immunoprecipitated and probed for known DISC components. As caspase-8 plays an essential role in receptor-mediated apoptosis characterized by DISC formation, the status of DISC in cells undergoing apoptosis due to loss of endogenous MADD expression was examined. Forty-eight-hour transduced HeLa cells and PA-1 cells were collected and lysed. Lysates were normalized for protein concentration, and DR4s/DR5s were immunoprecipitated using specific antibodies. Separated immune complexes were immunoblotted using antibodies specific for caspase-8, FADD, and DR4/DR5. The caspase-8 and FADD and the DR4/DR5 immunoblots were exposed for 4 h and for 30 min, respectively. FADD and pro-caspase-8 were found to be associated constitutively with the DRs in cells with and without MADD abrogation. However, the intermediate cleaved fragments of caspase-8 (p43/p41) were detected only in MADD-depleted cells, which indicated that activation of caspase-8 at the DRs was associated with spontaneous apoptosis resulting from MADD abrogation.

FADD and pro-caspase-8 were found to be constitutively associated with the DRs in cells with and without MADD abrogation. However, the intermediate cleaved fragments of caspase-8 (p43/p41) were detected only in MADD-depleted cells, which suggested that activation of caspase-8 at the DRs was associated with spontaneous apoptosis.

TRAIL induced DISC was immunoprecipitated from HeLa cells using a TRAIL-specific antibody and subjected to SDS-PAGE followed by western blotting. Staining for various TRAIL-DISC components revealed co-precipitation of DR4, FADD and caspase-8. Relative to control cells (SCR), immunoprecipitates from MADD-depleted cells (13L and Mid) showed increased levels of intermediate fragments of caspase-8 (p43/41). This observation correlated with enhanced caspase-8 activity observed earlier in these cells upon TRAIL treatment (FIG. 8).

Example 9

MADD Binds to DR4, but not Caspase-8 or FADD

To examine whether MADD confers resistance to apoptosis by interacting with caspase-8, MADD-YFP were expressed in HeLa cells and immunoprecipitated it using an IG20-specific antibody from lysates of cells that were left either untreated or treated with TRAIL (250 ng) for 30 minutes. These proteins were separated by SDS-PAGE and subjected to western blot analysis to probe for DISC components. DR4 but not caspase-8 co-precipitated with MADD in both untreated and TRAIL-treated cells. On the other hand, FADD co-precipitated with caspase-8 upon TRAIL treatment, while MADD and DR4 were not be co-precipitated with caspase-8 under either condition.

To determine whether MADD prevents caspase-8 activation by directly binding to caspase-8, HeLa cells were transfected with MADD-YFP. Thirty-six hours post-transduction, cells were either left untreated or treated with 250 ng of TRAIL for 30 min. Samples were lysed, and the lysates were normalized for protein concentration and pre-cleared. Equal amounts of proteins were incubated with either anti-IG20 or anti-caspase-8 antibody. Complexes were subjected to immunoblotting (WB, Western blot). Interestingly, endogenous DR4 but not caspase-8 co-precipitated with MADD in both untreated and TRAIL-treated cells. On the other hand, immunoprecipitation using a caspase-8-specific antibody followed by Western blotting showed co-precipitation of FADD with caspase-8 upon TRAIL treatment; whereas MADD and DR4 could not be co-precipitated with caspase-8 under either condition. The above results demonstrated that MAD D may exert its anti-apoptotic effect by directly binding to DR4 but not to caspase-8 or FADD.

Example 10

Akt Phosphorylates MADD in Vitro and in Vivo

Figure 13:
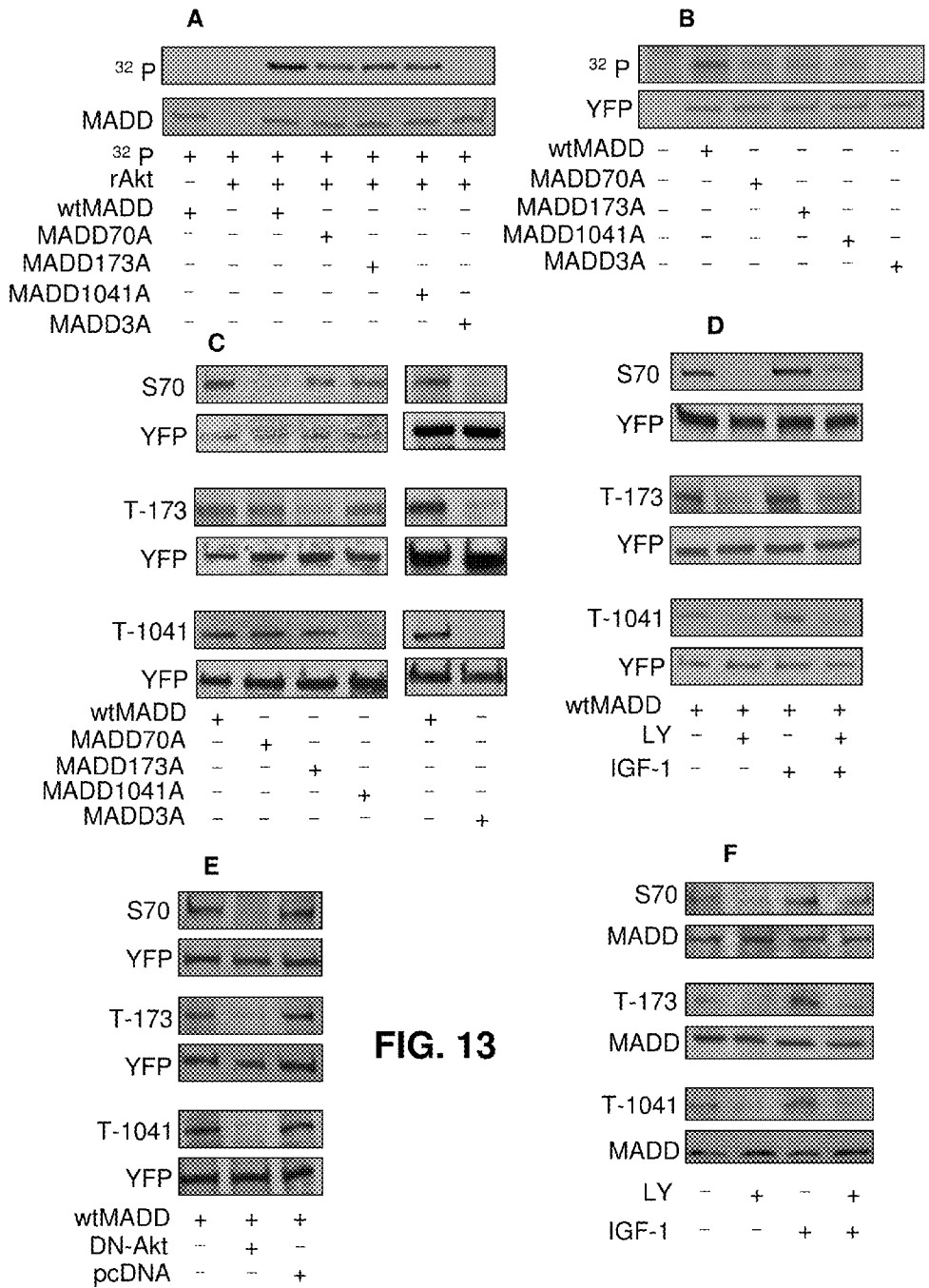
FIG. 13 shows that MADD is phosphorylated by Akt. (A) In vitro phosphorylation of rMADD by Akt. GST-wtMADD or -MADD mutants were expressed in bacteria, purified, and then incubated with rAkt and γ[$^{32}$P] ATP. After 1 h incubation at 30° C., the products were resolved on SDS-PAGE and $^{32}$P-labeled proteins were visualized by autoradiography. (B) MADD is labeled by [$^{32}$P]orthophosphate in vivo. HEK293 cells were transfected with wtMADD or MADD mutant constructs. Twenty-four hours after transfection cells were incubated with 0.3 mCi/ml [32P]orthophosphate for 6 h. MADD was immunoprecipitated with an anti-YFP antibody. The precipitated MADD was separated by SDS-PAGE, transferred to a nitrocellulose membrane, and subjected to autoradiography. Loaded MADD was visualized by staining the same membrane with an anti-YFP antibody. (C) HEK293 cells were transfected with cDNAs for wtMADD or MADD mutants and. 36 h later the cells were harvested for immunoblotting using the anti-phospho-S-70, -T-173 or -T-1041 antibodies. An anti-YFP antibody was used to detect exogenous MADD. (D) HEK293 cells were transfected with wtMADD and 24 hours later cells were serum starved for 20 h. Subsequently, they were treated with LY (10 μM) for 1 h and/or IGF-1 (150 ng/ml) for 20 minutes. The cell lysates were immunoblotted and probed with anti phospho-specific antibodies or an anti-YFP antibody. (E) HEK293 cells were co-transfected with wtMADD along with dominant negative Akt (DN-Akt) or the empty vector pcDNA3.1 (pcDNA). Immunoblots were probed with the anti phospho-specific antibodies or an anti-YFP antibody. (F) HeLa cells were serum starved for 20 h, treated with LY (10 μM) for 1 h, IGF-1 (150 ng/ml) for 20 minutes. Immunoblot was probed with the anti phospho-specific antibodies or an anti-MADD antibody.

To test whether MADD is a substrate of Akt, an in vitro assay was employed to test whether Akt could directly phosphorylate MADD. As shown in FIG. 13A, recombinant wild-type MADD (wtMADD) was phosphorylated by Akt. To understand which of the three sites is phosphorylated by Akt, MADD mutants including MADD70A (S70A), MADD173A (T173A), MADD1041A (T1041A) and MADD3A (all three residues were converted to alanine) were produced. The phosphorylation levels of MADD mutants including MADD70A, MADD173A and MADD1041A were reduced or absent. These results suggested that all three sites can be phosphorylated by Akt. It was tested whether MADD could be phosphorylated in vivo. First, it was tested whether MADD could be phosphorylated in vivo and found that WtMADD but not MADD3A could be metabolically labeled with [$^{32}$P]orthophosphate. A reduction in the levels of phosphorylation was observed in MADD with a single mutation (FIG. 13B). Second, three antibodies that specifically reacted with phosphorylated S70 (anti-phospho S70), T173 (anti-phospho T173) or T1041 (anti-phospho T1041) were raised, respectively. The phosphopeptides, CRQRRMpSLRDDTS (SEQ ID NO: 7) (S-70), GSRSRNSpTLTSL (SEQ ID NO: 8) (T-173), and KRKRSPpTESVNTP (SEQ ID NO: 9) (T-1041) were used to immunize the rabbits. Antisera were depleted of antibodies that recognize non-phosphorylated MADD by negatively selecting the antibodies using an identical non-phosphorylated peptide affinity column. Antibodies in the flow through were tested to ensure that they specifically bind only to the corresponding phosphorylated peptide and not the non-phosphorylated couterpart. WtMADD could be recognized by each of the three anti-phospho antibodies, whereas MADD70A, MADD173A and MADD1041A could not be recognized by the corresponding anti-phospho antibody. The residual signals noted most likely represent phopshorylated endogenous MADD (FIG. 13C). Third, Akt activation is controlled by phosphatidylinositol 3-kinase (PI3K), and it forms a signaling axis (PI3K-Akt axis). To understand whether MADD phosphorylation in vivo is controlled by PI3K-Akt axis, the PI3K activity was tested using insulin-like growth factor-1 (IGF-1). The S70, T173 and T1041 phosphorylation levels were increased upon IGF-1 stimulation. In contrast, their phosphorylation levels were decreased in the presence of PI3K inhibitor LY (FIG. 13D). These data suggested that PI3K is involved in the regulation of MADD phosphorylation. Fourth, it was tested whether Akt is responsible for in vivo MADD phosphorylation. As shown in FIG. 13E, dominant negative Akt (DN-Akt) inhibits MADD phosphorylation. These data suggest that MADD can be phosphorylated by Akt. Endogenous MADD is phosphorylated at all three sites upon IGF-1 stimulation, but was decreased considerably in the presence of LY (FIG. 13F). Taken together, these data indicate that the three sites of MADD can be phosphorylated by Akt.

Example 11

Figure 14:
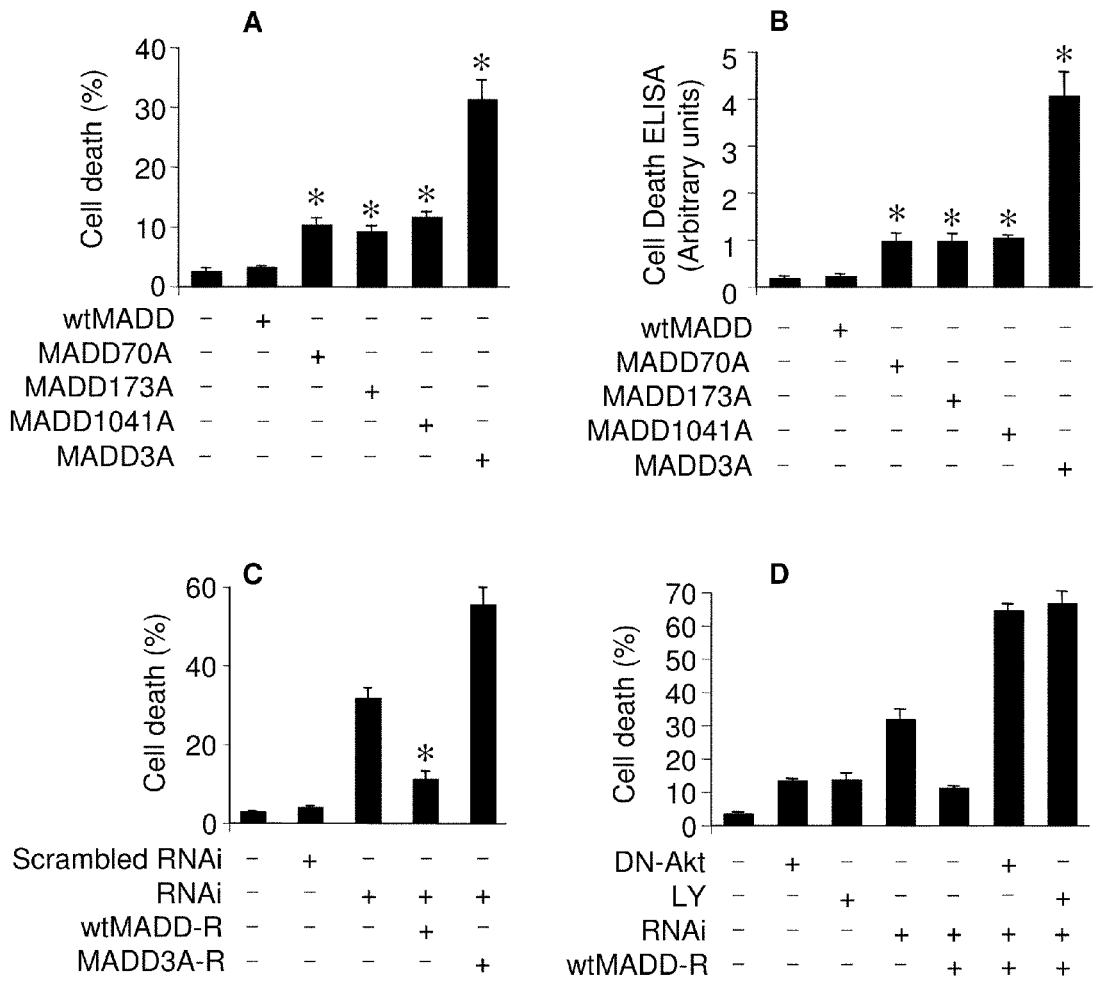
FIG. 14 demonstrates that phosphorylation is required for MADD to inhibit apoptosis. (A) HEK293 cells were transfected with various MADD constructs. Cell death was determined 48 h after transfection by Trypan Blue exclusion. *p<0.05 vs control. (B) Apoptosis analyzed by Cell Death Detection ELISA. *p<0.05 vs control. (C) Phosphorylatable but not the nonphosphorylatable MADD could rescue cell death upon endogenous MADD knockdown. HeLa cells were infected with the lentivirus harboring MADD shRNAi (RNAi) or its scrambled form (Scrambled RNAi). 24 h after infection, cells were transfected with the constructs of wtMADD-R or MADD3A-R. 48 h after transfection, cell death was determined by Trypan Blue exclusion. *p<0.05 vs RNAi alone. (D) Inhibition of Akt or PI3K could abolish the ability of wtMADD-R to rescue cell death upon endogenous MADD knockdown. HeLa cells were infected with the lentivirus harboring MADD shRNA (RNAi). 24 h after infection, cells were infected with the adenovirus harboring DN-Akt, and transfected with wtMADD-R. LY (10 μM) was added 6 h after transfection. 48 h after transfection, cell death was determined by Trypan Blue exclusion. Data are expressed as the mean±SEM of three independent experiments.

Lack of Phosphorylation Switches MADD from a Prosurvival to a Proapoptotic Protein To see whether phosphorylation is required for the prosurvival function of MADD, WT and mutant MADD were tested. Enforced expression of exogenous wtMADD alone could not induce cell death. Surprisingly, enforced expression of MADD70A, MADD173A or MADD1041A had minimal effects on cell death, MADD3A could induce a significant cell death (FIG. 14A). Detection of histone-associated DNA fragments showed an increase in oligonucleosomes in cells expressing MADD mutants (FIG. 14B) indicating that non-phosphorylatable MADD-induced apoptotic cell death. Since knockdown of endogenous MADD can cause cell death, it was tested whether the wtMADD or MADD3A could rescue this cell death. Only the shRNA resistant wtMADD (wt-MADD-R) and not the MADD3A-R could rescue cell death upon endogenous MADD knockdown (FIG. 14C), which was abrogated in the presence either LY or DN-Akt (FIG. 14D). Taken together, the prosurvival function of MADD is dependent upon its phosphorylation by Akt.

Example 12

Phosphorylation is Required for MADD to Bind to DR4

Figure 15:
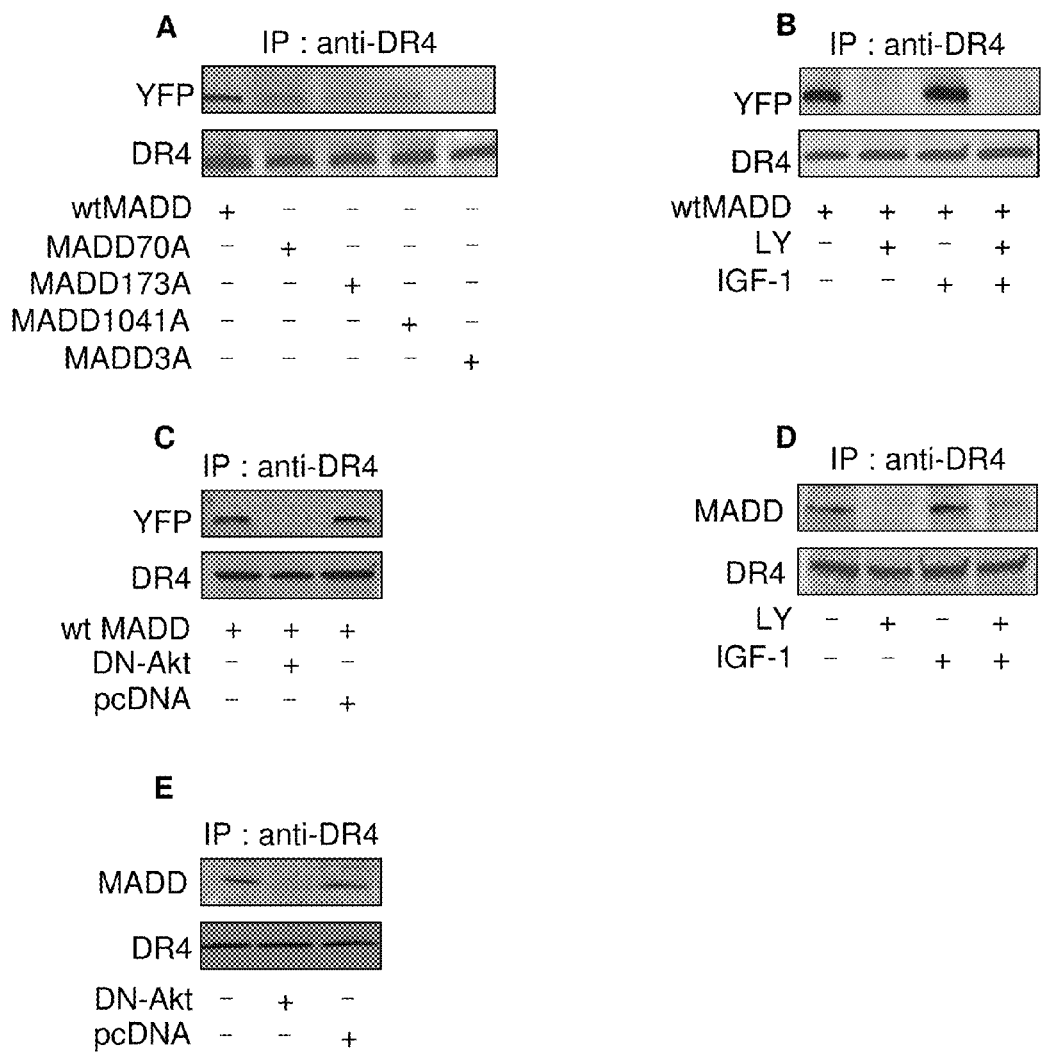
FIG. 15 shows that phosphorylation of MADD by Akt influences its binding to DR4. (A) Phosphorylation status of MADD could influence its binding to DR4. HEK293 cells were transfected with wtMADD or MADD mutants. 36 h after transfection, the cells were harvested for immunoprecipitation using an anti-DR4 antibody followed by immunoblotting using an anti-YFP antibody to detect exogenous MADD. The membrane was reprobed with an anti-DR4 antibody to show the protein loading. (B) PI3K can influence the association of exogenous MADD with DR4. HEK293 cells were transfected with wtMADD. Twenty four hours after transfection, the cells were serum starved for 20 h. Further, they were treated with LY (10 µM) for 1 h, IGF-1 (150 ng/ml) for 20 minutes. Immunoprecipitation using an anti-DR4 antibody was followed by immunoblotting using anti-YFP or anti-DR4 antibody. (C) Akt can influence exogenous MADD association with DR4. HEK293 cells were co-transfected with wtMADD along with DN-Akt or the empty vector pcDNA3.1 (pcDNA). Thirty six hours after transfection, the cells were harvested for immunoprecipitation using anti-DR4 antibody followed by immunoblotting with an anti-YFP or an anti-DR4 antibody. (D) PI3K can influence the association of endogenous MADD with DR4. HeLa cells were serum starved for 20 h, then treated with LY (10 µM) for 1 h, IGF-1 (150 ng/ml) for 20 minutes. Immunoprecipitation using an anti-DR4 antibody was followed by immunoblotting with an anti-MADD or an anti-DR4 antibody. (E) Akt can influence the association of endogenous MADD with DR4. HeLa cells were transfected with DN-Akt or pcDNA. Thirty six hours after transfection, the cells were collected for immunoprecipitation using an anti-DR4 antibody followed by immunoblotting with an anti-MADD antibody.

MADD can bind to DR4 and thereby block the activation of the extrinsic apoptotic pathway. Results presented herein show that WtMADD can associate with DR4. While the association of DR4 with MADD single mutants was reduced, it was almost non-existant with MADD3A (FIG. 15A). Stimulation of PI3K by IGF-1 increased, while inhibition by LY reduced, the association between wtMADD and DR4 (FIG. 15B). A similar inhibition was noted in cells expressing the DN-Akt (FIG. 15C). Testing for a similar interaction between endogenous MADD and DR4 revealed considerable interaction between the two proteins. This interaction was reduced in the presence of LY (FIG. 15D) or DN-Akt (FIG. 15E). These results demonstrated that Akt phosphorylation of MADD is required for its interaction with DR4.

Example 13

Nonphosphorylated MADD Cannot Bind to DR4, but can Bind to 14-3-3

Figure 16:
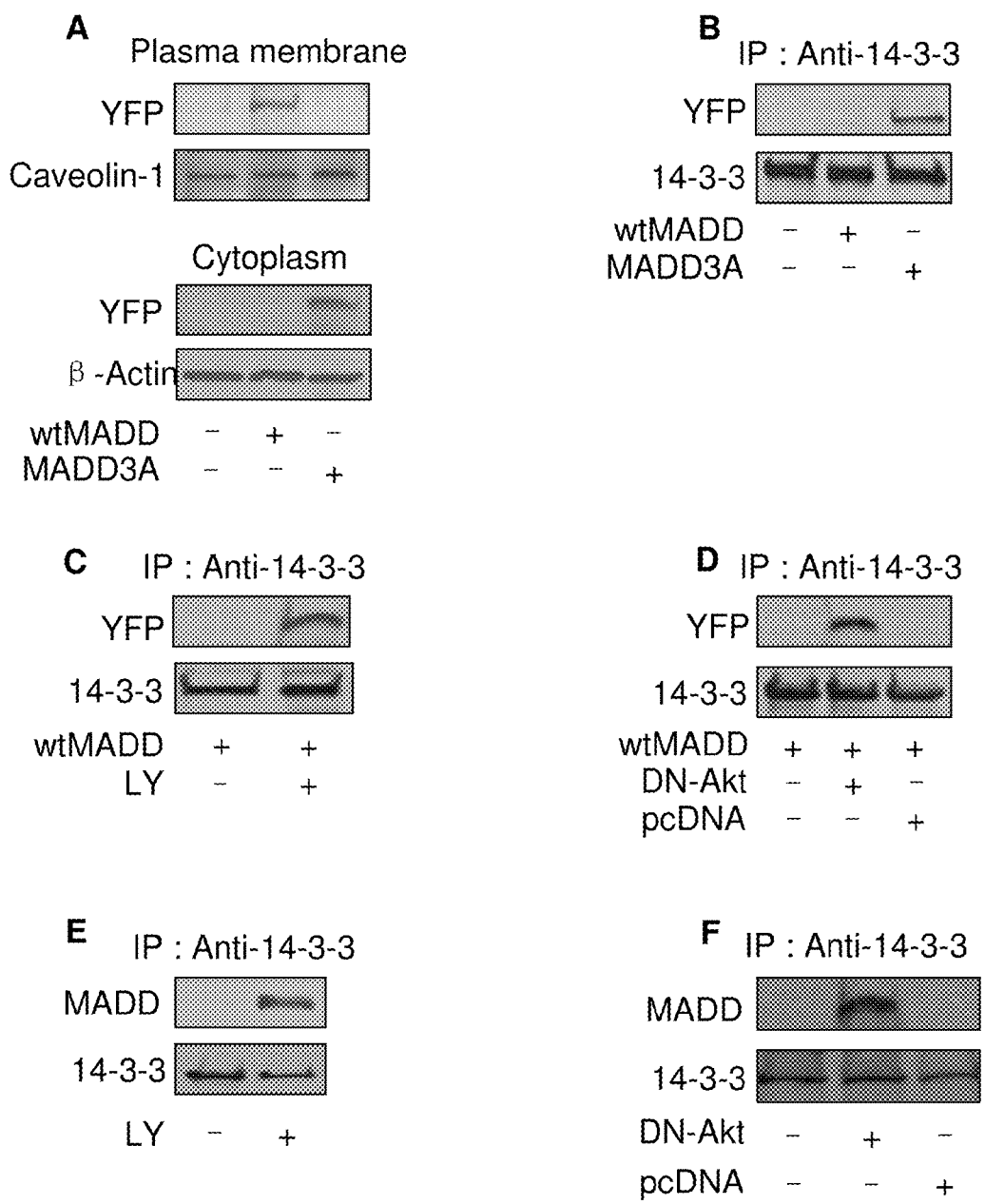
FIG. 16 shows that MADD upon nonphosphorylation, binds to 14-3-3. (A) Cellular distributions of wtMADD and MADD3A. HEK293 cells were transfected with wtMADD or MADD3A. 36 h after transfection, the cells were harvested and membrane andcytosolic fractions were prepared. Immunoblotting was performed using an anti-YFP antibody. Actin and caveolin-1 were used as loading controls. (B) MADD3A but not wtMADD binds to 14-3-3. HEK293 cells were transfected with wtMADD or MADD3A. 36 h after transfection, the cells were harvested for immunoprecipitation using an anti-14-3-3 antibody followed by immunoblotting using an anti-YFP antibody for detecting exogenous MADD. The membrane was reprobed with an anti-14-3-3 antibody to show protein loading. (C) Inhibition of PI3K can lead to the association of wtMADD with 14-3-3. HEK293 cells were transfected with wtMADD. Cells were serum starved for 20 h and treated with LY (10 µM) for 1 h. Immunoprecipitation was performed using an anti-14-3-3 antibody, followed by immunoblotting using an anti-YFP or an anti-14-3-3 antibody. (D) Inhibition of Akt can result in the association of wtMADD with 14-3-3. HEK293 cells were co-transfected with wtMADD along with DN-Akt or pcDNA. Cells were harvested for immunoprecipitation with anti-14-3-3 antibody followed by immunoblotting using the anti-YFP or anti-14-3-3 antibodies. (E) Inhibition of PI3K leads to the association of endogenous MADD with 14-3-3. HeLa cells were serum starved for 20 h, then treated with LY (10 µM) for 1 h. Immunoprecipitation with the anti-14-3-3 antibody was followed by immunoblotting using anti-MADD or anti-14-3-3 antibodies. (F) Inhibition of Akt results in the association of endogenous MADD with 14-3-3. HeLa cells were transfected with DN-Akt or pcDNA. Immunoprecipitation with the anti-14-3-3 antibody was followed by immunoblot using an anti-MADD or an anti-14-3-3 antibody.

To explore the molecular mechanism by which nonphosphorylated MADD can trigger apoptosis, the cellular localization of phosphorylated and nonphosphorylated MADD was determined. Phosphorylated wtMADD is primarily located to the plasma membrane fraction, whereas nonphosphorylated MADD3A is located in the cytosolic fraction (FIG. 16A). Since 14-3-3 is known to sequester proapoptotic factors, MADD interaction with 14-3-3 was tested. This indicated that nonphosphorylated MADD, but not wtMADD, can interact with 14-3-3 (FIG. 16B). This was confirmed when WtMADD was able to bind to 14-3-3 only in the presence of LY (FIG. 16C) or DN-Akt (FIG. 16D). This requirement was unequivocally demonstrated when the endogenous nonphosphorylated MADD could bind to 14-3-3 only in the presence, but not in the absence, of LY (FIG. 16E) or DN-Akt (FIG. 16F).

Example 14

Binding of Nonphosphorylated MADD to 14-3-3 Releases Bax

Since Bax can be sequestered by 14-3-3, it was tested whether the interaction of nonphosphorylated MADD with 14-3-3 could affect 14-3-3 and Bax interaction. Enforced expression of MADD3A, but not wtMADD, led to the disassociation of Bax from 14-3-3 (FIG. 17A). WtMADD in the presence, but not in the absence, of DN-Akt was able to induce disassociation of Bax from 14-3-3 (FIG. 17B). As shown in FIG. 17C, Decreased Bax association with 14-3-3 in the presence of DN-Akt indicated that the endogenous nonphosphorylated MADD can also interact with 14-3-3. Further, the DN-Akt could reduce Bax-14-3-3 interaction only when MADD was expressed, and not when MADD was knocked down, indicating the MADD is required for Bax dissociation from 14-3-3.

Example 15

Upon Nonphosphorylation, MADD Triggers Bax Translocation to the Mitochondria

To test whether Bax is the downstream mediator of apoptosis, Bax localization was analyzed. The Bax was translocated to the mitochondria in cells expressing MADD3A, but not wtMADD. Concomitantly, cytochrome c was released from the mitochondria into cytoplasm in cells expressing MADD3A (FIG. 18A). As shown in FIG. 18B, Bax translocation to the mitochondria could be observed in cells expressing DK-Akt only when MADD was expressed and not in the presence of MADD shRNA, indicating that MADD is necessary for Bax translocation induced by DN-Akt. Results in FIG. 18C show reduced in death in HCT116Bax$^{-/-}$ cells relative to HCT116Bax$^{+/+}$ cells indicating that MADD3A induced death, at least in part, is dependent upon Bax expression. Together, these data show that nonphosphorylated MADD can provoke the intrinsic apoptotic pathway.

Example 16

TRAIL Targets MADD to Initiate Extrinsic and Intrinsic Apoptotic Pathways

Figure 19:
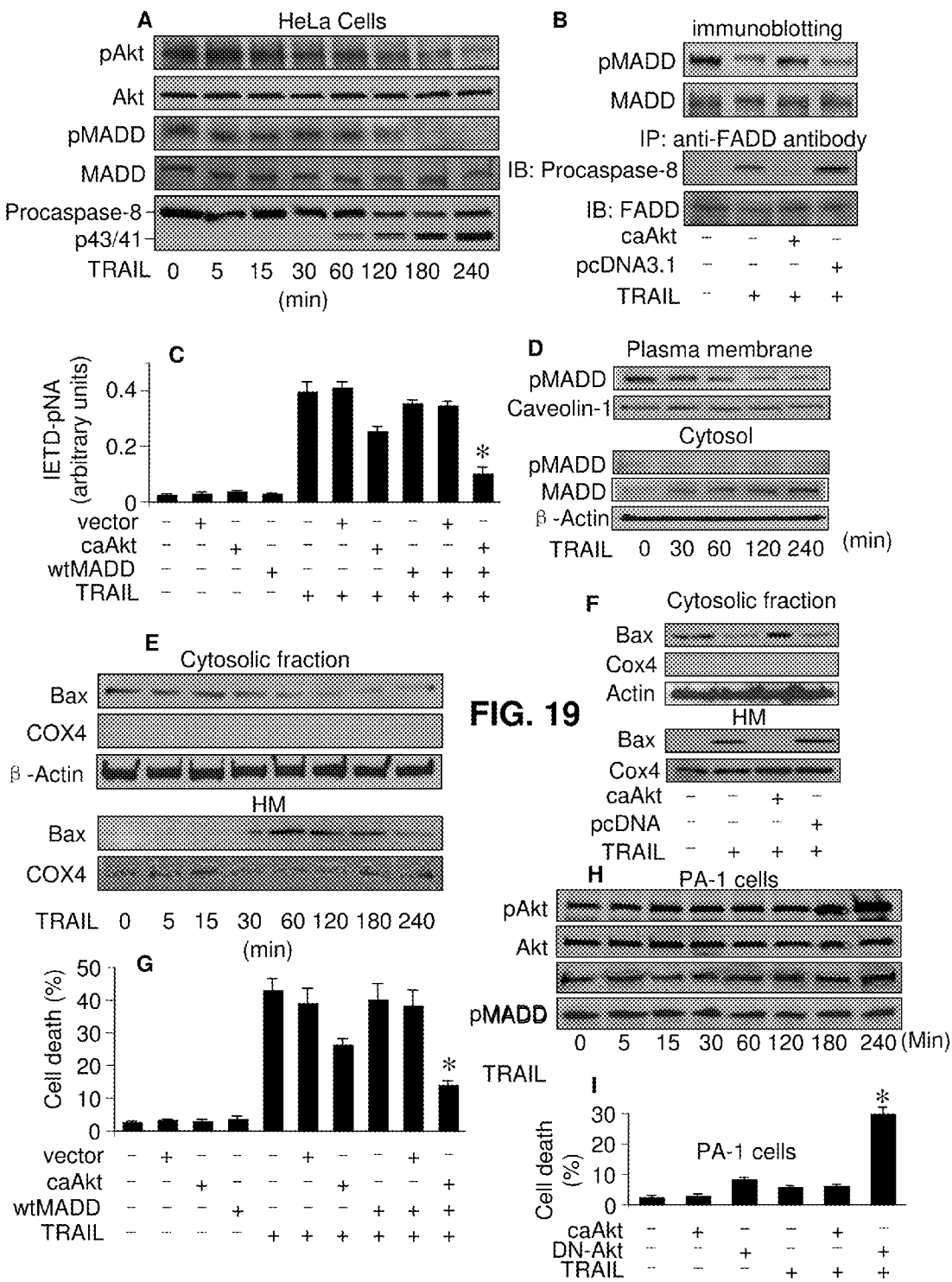
FIG. 19 shows that TRAIL-induced cell death is related to MADD phosphorylation status. (A) TRAIL treatment reduces the levels of Akt and MADD phosphorylation, and leads to caspase-8 activation. Hela cells were treated with TRAIL (50 ng/ml). The phosphorylation level of Akt was analyzed by immunoblotting using an anti-phospho Akt antibody. The phosphorylation levels of MADD was analyzed by immunoblotting using the anti-phospho T1041 antibody. Caspase-8 activation was analyzed by immunoblotting using an anti-caspase-8 antibody. (B) TRAIL induces FADD-procaspase-8 binding depending upon MADD phosphorylation status. HeLa cells were transfected either with caAkt or pcDNA3.1 empty vector. Cells were treated with TRAIL for 1 h. The MADD phosphorylation was analyzed by immunoblotting using the anti-phospho T1041 antibody. The association of procaspase-8 and FADD was analyzed by immunoprecipitation using an anti-FADD antibody followed by immunoblotting using an anti-caspase-8 antibody. (C) wtMADD in the presence of caAkt can prevent caspase-8 activation induced by TRAIL. HeLa cells were transfected with plasmids encoding caAkt and wtMADD. The empty vector (pcDNA3.1) was used as the control. 24 h later cells were treated with TRAIL (50 ng/ml) for 4 hours and caspase-8 activity was analyzed. *p<0.05 vs TRAIL+caAkt. (D) TRAIL induces MADD re-location. HeLa cells were treated with TRAIL (50 ng/ml). The localizations of phosphorylated and nonphosphorylated forms of MADD in the membrane and cytosolic fractions were analyzed by immunoblotting using the anti-phospho T1041 antibody. (E) TRAIL induces Bax translocation to mitochondria. HeLa cells were treated with TRAIL as described for (A). The Bax distribution in cytoplasm and HM was analyzed by immunoblotting using an anti-Bax antibody. COX4 served as a mitochondria marker. (F) Bax translocation to mitochondria can be inhibited by caAkt. HeLa cells were transfected with the caAkt or pcDNA3.1 empty vector. Cells were treated with TRAIL for 1 h. The distributions of Bax in cytoplasm and HM were analyzed as described for (E). (G) wtMADD in the presence of caAkt can attenuate TRAIL-induced cell death. HeLa cells were treated as described for (F). Cell death was analyzed 12 h after TRAIL treatment. *p<0.05 vs TRAIL+ caAkt. (H) Effect of TRAIL on Akt and MADD phosphorylation status in PA-1 cells. PA-1 cells were treated with TRAIL, and the phosphorylation levels of Akt and MADD were analyzed as described for (A). (I) DN-Akt can sensitize PA-1 cells to undergo TRAIL-induced apoptosis. PA-1 cells were transfected with caAkt or DN-Akt and 24 h later the cells were treated with TRAIL (50 ng/ml). Cell death was analyzed by Trypan Blue exclusion 12 h after TRAIL treatment. *p<0.05 vs TRAIL alone.

DR4 is a TRAIL receptor and the inability of nonphosphorylated MADD to bind to DR4 led to consider whether MADD is a molecular target of TRAIL. As shown in FIG. 19A, upon treatment with TRAIL the levels of phosphorylation of Akt and MADD were reduced with a concomitant activation of caspase-8. The FADD was associated with pro-caspase-8, suggesting activation of the extrinsic apoptotic pathway (FIG. 19B). To determine if MADD phosphorylation levels could influence TRAIL induced effects, the constitutively active form Akt (caAkt) was employed. CaAkt could prevent decrease in MADD phosphorylation, and block FADD and procaspase-8 association upon TRAIL treatment. Similarly, caspase-8 activity which was increased upon TRAIL treatment was attenuated by wtMADD only in the presence of caAkt (FIG. 19C) upon TRAIL treatment. Thus, it appears that TRAIL could activate the extrinsic pathway by reducing the levels of phosphorylated MADD.

The ability of non-phosphorylated MADD to induce Bax translocation led to a consideration whether MADD is involved in the intrinsic apoptotic pathway initiated by TRAIL. MADD was redistributed from the plasma membrane to cytosol upon TRAIL treatment (FIG. 19D) with a concomitant translocation of Bax from cytoplasm to mitochondria (FIG. 19E). Significantly, the caAkt could block Bax translocation to mitochondria (FIG. 19F) and allow WtMADD to inhibit TRAIL-induced cell death only in its presence (FIG. 19G). These data clearly indicated that MADD phosphorylation status is a major determinant of Bax translocation and cell death.

Example 17

Figure 20:
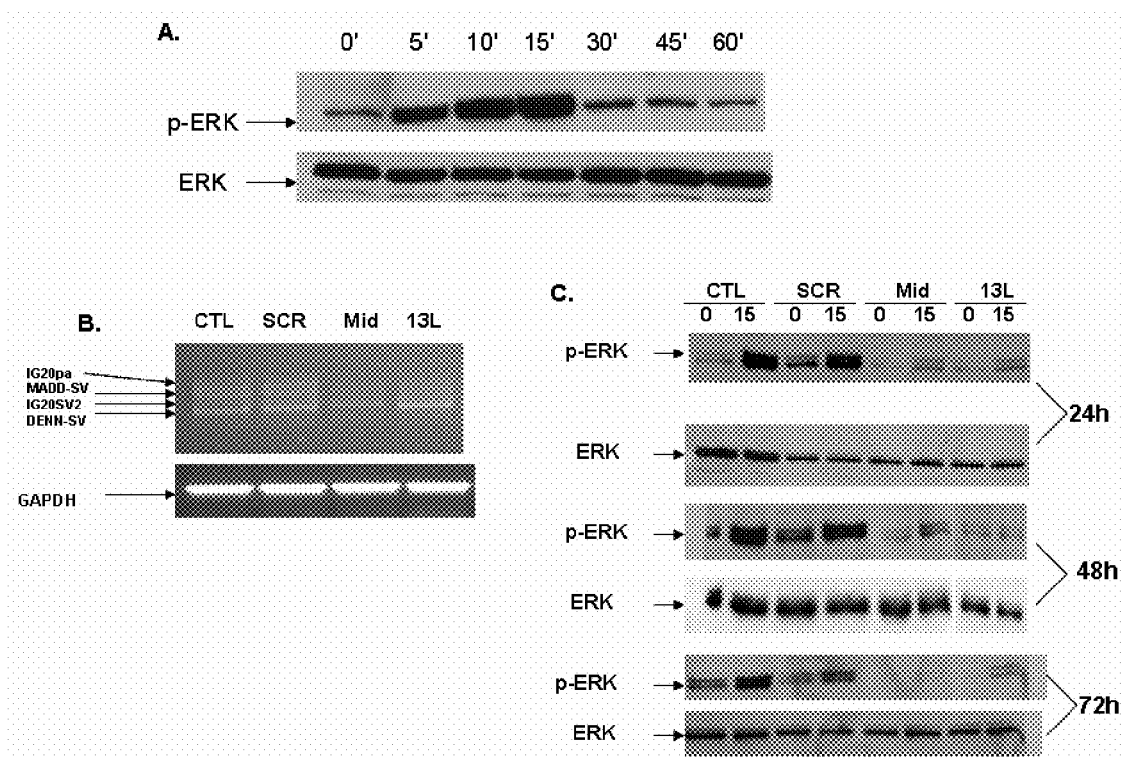
FIG. 20 shows that IG20-SVs regulate TNF-α induced ERK activation. (A) Time-kinetics of TNF-α induced ERK activation. HeLa cells ($3 \times 10^6$ per 100 mm dish) were serum starved for 6 h and were either left untreated or treated with TNF-α (50 ng/mL) for different time periods as indicated. Cell lysates were analyzed for phosphorylated ERK or total ERK by immunoblot. (B) Down-modulation of endogenous IG20-SVs in HeLa cells. One microgram of total RNA obtained from HeLa cells 48 h post-transduction was used for reverse-transcription-polymerase chain reaction. The products were separated on a 2% agarose gel. Amplification of all four IG20-SVs was done using F2-B2 primers. (C) Down-modulation of IG20-SVs or MADD-SV alone significantly decreases TNF-α induced ERK phosphorylation. HeLa cells ($3 \times 10^6$ per 100 mm dish) were either untransduced or transduced with different lentiviruses expressing SCR, Mid and 13L ShRNA for different time periods as indicated. At the end of each time period, the cells were serum starved for 6 h and were either left untreated or treated with TNF-α (50 ng/mL) for 15 min. Cell lysates were analyzed for phosphorylated ERK or total ERK by immunoblot. The data shown is representative of at least 3 independent experiments.

Down-Modulation of IG20 Gene Expression Significant Decreases TNF-α Induced ERK Activation To gain insight into the time kinetics of TNF-α induced ERK phosphorylation, HeLa cells were treated with TNF-α (50 ng/mL) for different time periods. As shown in FIG. 20A, TNF-α induced rapid phosphorylation of ERK1/2 with maximum ERK phosphorylation being seen after 15 min of TNF-α stimulation. Results showed that TNF-α is a potent activator of ERK1/2 phosphorylation in HeLa cell line and the rapidity with which it occurred indicated that new protein synthesis was not required. Down-modulation of IG20 transcripts upon treatment with different ShRNA expressing lentiviruses was monitored by RT-PCR. As evident from the result (FIG. 20B), IG20 transcripts were significantly down-modulated by 48 h of transduction. Lentivirus expressing Mid ShRNA knocked down the expression of all the four IG20-SVs whereas 13L knocked down MADD and IG20pa and 16E knocked down IG20pa and IG20-SV2. SCR was used as a vector control which does not target any IG20 isoforms. HeLa cells do not begin to undergo spontaneous apoptosis until 72 h post-transduction even though IG20 transcripts have been knocked out because of the time required for complete degradation of the remaining endogenous proteins. The effects of TNF-α induced ERK phosphorylation in HeLa cells up to 72 h post transduction were studied. Significant decrease in ERK1/2 phosphorylation (activation) was observed upon down modulation of all IG20 spice variants using Mid ShRNA or by down modulation of MADD-SV along with IG20pa employing 13L ShRNA (FIG. 20C) starting from 24 h to 72 h post transduction. Together, these data suggest that IG20 gene plays an important role in TNF-α induced ERK phosphorylation.

Example 18

Down-Modulation of IG20-SVs or MADD-SV Alone Does not Affect TNF-α Induced NF-κB Activation The NF-κB-mediated survival pathway plays an important role in the resistance of cancer cells towards apoptosis. In order to test the possibility that down-modulation of MADD-SV negatively affects NF-κB activation, the effect of TNF-α treatment in shRNA transduced cells was determined. HeLa cells were treated thirty-six hours post-transduction with 50 ng of TNF-α and collected them as indicated in FIG. 21A. The lysates were subjected to immunoblot and probed for IkB-α; an inhibitor of NF-κB activation. IkB-α degradation is facilitated by its phosphorylation, as a consequence of TNF-α stimulation. Degradation of IkB-α results in the activation of NF-kB dimers (RelA and c-Rel) and their subsequent translocation to the nucleus where they activate the transcription of anti-apoptotic molecules. Thus degradation of IkB-α is considered as an indicator of NF-kB activation. As observed in FIG. 21A, the pattern of IkB-α degradation upon MADD-SV down-modulation (in Mid and 13L cells) was similar to control (SCR). This indicated that down-modulation of MADD-SV does not affect NF-κB activation by TNF-α. This was confirmed by measuring levels of IL-6 secretion which is an NF-kB-responsive gene (FIG. 21B). The conditioned media from untreated and TNF-α treated cells were collected and the amounts of IL-6 secreted were measured by ELISA. The levels of secreted IL-6 did not appear to be affected upon MADD-SV down-modulation. These results indicate that down-modulation of MADD-SV does not significantly affect TNF-α induced NF-kB activation.

Example 19

The Role of IG20 is Specific to TNF-α Induced ERK Activation and is Not Involved in the Activation of Other MAP Kinases by TNF-α

In order to test whether IG20 gene is involved in the activation of other MAP kinases like JNK and p38, HeLa cells transduced with different ShRNA expressing lentiviruses were probed for P-JNK1/2 and P-p38. It was shown in FIG. 22A that down-modulation of all IG20-SVs or a combination of MADD-SV along with IG20pa did not affect JNK1/2 activation by TNF-α. Similarly, down-modulation of IG20-SVs has no role in TNF-α induced p38 phosphorylation (FIG. 22B). This result indicates that IG20's role is highly specific to TNF-α induced ERK activation.

Example 20

IG20 Does not Affect Growth Factor Mediated ERK Activation

All the splice variants of the IG20 gene have a C-terminal DDHR (death domain homology region) with which they interact with death domain containing receptors like TNFR1. This interaction probably facilitated IG20 to play a prominent role in TNF-α induced ERK activation. The other major ERK activation pathway relevant to cancer is by growth factors binding to receptor tyrosine kinases. The results presented in FIG. 23A indicate that down-modulation of IG20-SVs (employing Mid ShRNA) have no effect on epidermal growth factor mediated ERK1/2 phosphorylation but has considerably reduced ERK phosphorylation upon TNF-α stimulation. This is consistent with the fact that since IG20-SVs cannot interact with receptor tyrosine kinases unlike TNFR1, they should have no role in growth factor mediated ERK activation. To further substantiate the specificity of IG20 to TNF-α induced ERK pathway, the effect of other mitogens like TRAIL and LPS were studied on ERK phosphorylation upon IG20 down modulation. It was evident from FIG. 23 (B&C) that down-modulation of IG20-SVs (using Mid Sh RNA) did not effect the ERK phosphorylation upon stimulation with either TRAIL or LPS.

Example 21

MADD-SV is Necessary and Sufficient for TNF-α Induced ERK Activation

Whether MADD isoform alone is playing a critical role in TNF-α induced ERK activation was determined. Lentiviruses expressing different ShRNA can knockdown all or a select combination of IG20-SVs but not individual isoforms alone. Selective knockdown of MADD-SV and IG20pa (using 13L ShRNA expressing lentivirus) could significantly reduce ERK1/2 activation. To determine the roles of IG20pa-SV and MADD-SV in TNF-α induced ERK activation, 16E ShRNA expressing lentivirus which knocks out IG20pa-SV and IG20-SV2 but spares MADD-SV along with DENN-SV was used. The results presented in FIG. 24A indicate that knockdown of IG20pa-SV along with IG20-SV2 (using 16E ShRNA) did not reduce ERK1/2 phosphorylation. Since ERK1/2 phosphorylation using 16E ShRNA (where MADD-SV along with DENN-SV is spared from knockdown), is similar to SCR control, it indicated that MADD isoform may be important for TNF-α induced ERK phosphorylation. To delineate the role of MADD from DENN-SV, the effect of IG20 down-modulation upon TNF-α induced ERK phosphorylation was analyzed in PA-1 ovarian carcinoma cell line which expresses only two IG20 isoforms namely, MADD and DENN-SV. Knock down of both IG20 isoforms using Mid ShRNA or MADD alone (sparing DENN-SV knock down) employing 13L ShRNA has also lead to significant abrogation of ERK activation when compared to the SCR control cells (FIG. 24B). This indicated that down-modulation of MADD-SV alone is necessary and sufficient for abrogating TNF-α induced ERK phosphorylation. Whether exogenous MADD-SV rescued ERK activation upon down modulation of all endogenous IG20-SVs was verified. For this, exogenous Mid ShRNA resistant MADD (Sir-MADD) or a vector control (EYFPC1) was overexpressed followed by knock down of all endogenous IG20-SVs using Mid ShRNA. The results presented in FIG. 24C demonstrate that over-expression of Sir-MADD has rescued ERK activation after knockdown of all endogenous isoforms by Mid ShRNA to a level comparable to control untransduced cells. MADD-SV of the IG20 gene is necessary and sufficient for ERK activation.

Example 22

Down-Modulation of IG20 Affects Cancer Cell Function and Promotes Susceptibility to Undergo Apoptosis The effect of down-modulation of IG20-SVs on the phosphorylation of a downstream substrate of ERK and an important kinase, p90RSK was investigated. Down-modulation of IG20-SVs employing Mid ShRNA has led to a dramatic decrease in phosphorylation of p90RSK (FIG. 25A). The effect of down-modulation of MADD-SV on TNF-α induced apoptosis was assessed. HeLa cells, transduced with different lentiviral vectors for 36 hours were treated with TNF-α (50 ng) alone and apoptosis was assessed based on caspase-3 activation. As observed in FIG. 25B, down-modulation of all IG20-SVs or MADD-SV alone has resulted in increased susceptibility to TNF-α-induced apoptosis as evidenced by enhanced activation of effector caspase-3.

TABLE 1

Nucleic acid regions targeted for shRNA knock-down analysis.

| siRNA | Region | Targeting Exon | Targeting Isoform |
|---|---|---|---|
| SUP | Vector Control | None | None |
| Mid | 5'GTACCAGCTTCAGTCTTTC-3' (SEQ ID NO: 10) | Exon 15 | IG20, MADD, SV-2, DSV |

TABLE 1-continued

Nucleic acid regions targeted for shRNA knock-down analysis.

| siRNA | Region | Targeting Exon | Targeting Isoform |
|---|---|---|---|
| 13L | 5' CGGCGAATCTATGACAATC-3' (SEQ ID NO: 4) | Exon 13L | IG20, MADD |
| 16E | 5' CTCTAATGGAGATTGTTAC-3' (SEQ ID NO: 11) | Exon 16 | IG20, SV-2 |
| SCR control-siRNA | 5' TTTAACCGTTTACCGGCCT-3' (SEQ ID NO: 12) | None | None |

Materials and Methods

Design of siRNA. The siRNAs used to target all, or a combination of IG20-SVs, are shown in Table I. Several putative siRNA sequences to target IG20 transcripts were obtained from the Dharmacon (Lafayette, Colo.). The most suitable sequences were sorted out based on less than 50% GC content, high AU content towards the 3' end and no inverted repeats within the siRNA region (Reynolds et al. (2004), *Nat Biotechnol*, 22(3), 326-30.).

Plasmid Construction. The siRNAs were cloned into the pSUPER vector using BglII and HindIII sites (Brummelkamp et al., (2002), *Science*, 296(5567), 550-3.) to generate pS-Mid, pS-13L, pS-16E and pS-SCR plasmids. The respective shRNA cassettes (including the H1 RNA promoter and the shRNA) were excised form the pSUPER plasmids using XbaI and ClaI sites and ligated into the pNLSIN-CMV-GFP vector (Lee et al., (2003), *J Virol.* (22), 11964-72.) to generate SUP (vector control), Mid, 13L, 16E and SCR (negative control) lentivirus constructs. The pcTat, pcRev and pHIT/G were gifts from Dr. B R Cullen and Dr. T J Hope. The IG20pa-YFP plasmid (Ramaswamy et al., (2004), *Oncogene*, 23(36), 6083-94) was used as a backbone to sub-clone MADD-YFP and DENN-SV-YFP plasmids from respective pBKRSV plasmids (Al-Zoubi et al., (2001), *J Biol Chem*, 276 (50), 47202-11.) using MluI and EcoRV sites. The DENN-SV-YFP-mut, MADD-YFP-mut and IG20-YFP-mut constructs were generated using the Quickchange XL site-directed mutagenesis kit (Stratagene, La Jolla, Calif.) according to the manufacturer's protocol. Briefly, the primers 5'CGGAAC-CACAGTACAAGCTTTAGCCTCTCAAAC-CTCACACTGCC3' (SEQ ID NO: 13) (forward) and 5'GGCAGTGTGAGGTTTGAGAG-GCTAAAGCTTGTACTGTGGTTCCG3' (SEQ ID NO: 14) (reverse) were designed to insert silent mutations at four sites in the cDNAs without affecting the amino acid sequence, as shown in bold, and were used to amplify the mutant-YFP-cDNAs. HindIII site in the mutants, generated due to base substitutions, was used to identify positive clones which were subsequently confirmed by sequencing.

Cell Culture. 293T cells, HeLa cells and PA-1 cells were cultured in Dulbecco's modified Eagle's medium (Invitrogen, CA) supplemented with 10% fetal bovine serum, 2 mM L-glutamine, 100 U/mL penicillin-G and 100 µg/mL streptomycin. All cell lines were maintained at 37° C. in a humidified chamber with 5.5% $CO_2$.

Screening of shRNAs. IG20-YFP constructs were co-transfected with different pSUPER-shRNA constructs in different ratios (1:1, 1:3, 1:7) into 293T cells using Calcium phosphate. 24 hours post-transduction, cells were trypsinized, collected and washed twice in cold PBS, and analyzed for YFP expression by flow cytometry using a FACS Calibur (Becton Dickinson, N.J.).

Lentivirus production. Sub-confluent 293T cells grown in 100 mm plates were co-transfected with 10.8 µg of the respective lentivirus vector, 0.6 µg pcRev, 0.6 µg of pcTat and 0.3 µg of pHIT/G using calcium phosphate. Culture medium was replaced 16 hours later, and the supernatant was harvested 40 hours post-transfection and filtered using a 0.45 µm filter. The optimal viral titer for each cell type was determined as the least amount of viral supernatant required to transduce 80% of target cells without apparent cytotoxicity.

RT-PCR. Total RNA was extracted from $1 \times 10^6$ transduced cells using Trizol (Invitrogen Life Technologies, Carlsbad, Calif.), and 1 jig of RNA was used for RT-PCR using the Super-Script One-Step RT-PCR system (Invitrogen Life Technologies, Carlsbad, Calif.). Briefly, the cDNAs were synthesized at 50° C. for 30 minutes followed by incubation at 94° C. for 2 minutes. Subsequently, 35 cycles of PCR were carried out with de-naturation at 95° C. for 30 seconds, annealing at 55° C. for 30 seconds and extension at 72° C. for 1 minute. This was followed by a final incubation at 72° C. for 7 minutes. The sequences of F2-B2 and GAPDH primers were as published (Al-Zoubi et al., (2001), *J Biol Chem*, 276 (50), 47202-11.). 13L-Forward (5'CGCCGGCGAATCTAT-GACAAT3' (SEQ ID NO: 15)) and B2-reverse primers were used to amplify only MADD and IG20pa. The PCR products were then separated on a 2% agarose gel.

Hoechst Staining. $5 \times 10^5$ transduced cells were collected and washed in cold PBS. 1 jig/mL Hoechst 33342 and 5 jig/mL Propidium Iodide (Sigma, St. Louis, Mo.) were used to stain cells for five minutes. Cells with condensed chromatin were analyzed using a BD-LSR (Becton Dickinson, N.J.). Highly PI-positive cells which represent necrotic or late-apoptotic cells were excluded from the analysis. Only GFP-positive cells were included in the analysis.

TMRM staining. $5 \times 10^5$ transduced cells were collected and washed in cold PBS and then stained with 100 nM tetramethylrhodamine methyl ester (Molecular Probes, Invitrogen, CA) for 15 minutes at 37° C. Cells were washed with cold PBS and then subjected to FACS analysis using a FACS Calibur. Only GFP-positive (shRNA-expressing) cells were included in the analysis.

Caspase Detection. $5 \times 10^5$ transduced cells were collected and washed 3x in cold PBS and then stained with either Red-z-VAD-FMK (pan-caspases), Red-IETD-FMK (active caspase-8) or Red-LEHD-FMK (active-caspase-9) (EMD Biosciences Inc.) for 30 minutes at 37° C. Transduced GFP-positive cells were analyzed for active caspase staining using a FACS Calibur.

Cell Proliferation. 24 hours post-transduction, $5 \times 10^5$ HeLa or $8 \times 10^5$ PA-1 cells were plated into six-well plates. Every other day, cells were collected, washed and stained with trypan blue, and trypan blue-negative viable cells were counted.

CFSE Dilution Assay. 24 hours post-transduction, $5 \times 10^5$ HeLa or $8 \times 10^5$ PA-1 cells were stained with 2 µM SNARF-1 carboxylic acid, acetate, succinimidyl ester (S-22801, Molecular Probes, Invitrogen, CA) for 15 minutes at 37° C. Cells were then washed and either used immediately for FACS analysis or plated into six-well plates. Every other day, cells were collected, washed and CFSE dilution, as an indicator of cell division, was determined by FACS analysis.

Crystal Violet Staining. $5 \times 10^5$ HeLa and $8 \times 10^5$ PA-1 cells were plated into six-well plates. 24 hours later cells were treated with different shRNA-expressing lentiviruses for 4 hours. Cells were washed and replenished with fresh warm medium. Twelve days later, cells were fixed in ice-cold methanol and stained with crystal violet to assess viability and colony formation.

Antibodies and other reagents. The anti-IG20 peptide polyclonal antibody, raised against 3 different peptides from the N-terminal, middle and C-terminal region of IG20, has been previously described (Al-Zoubi et al., (2001) *J Biol Chem*, 276 (50), 47202-11). Anti-Caspase-8 antibody (C-15) was a gift from Marcus E. Peter (Ben May Institute of Cancer Research, University of Chicago, Chicago). Anti-FADD antibodies were obtained from BD PharMingen, San Diego, Calif., and anti-GFP/YFP antibody (JL-8 clone) was purchased from Clontech Palo Alto, Calif. Anti-caspase-8 (C-20) for immunoprecipitation, anti-DR5 (IMG 120), anti-DR4 (H-130), anti-caspase-3 (H-277) and anti-DR4 (B-9 monoclonal) antibodies were obtained from Santa Cruz Biotechnology, Inc., Santa Cruz, Calif. Anti-TRAIL-biotinylated antibody and recombinant human-TRAIL were obtained from Peprotech Inc., Rocky Hill, N.J. Anti-actin antibody was obtained from Sigma-Aldrich Corp, CA.

Total RNA was extracted from $1 \times 10^6$ transduced cells using Trizol (Invitrogen Life Technologies, Carlsbad, Calif.), and 1 µg of RNA was used for RT-PCR using the Super-Script One-Step RT-PCR system (Invitrogen Life Technologies, Carlsbad, Calif.). RT-PCR was carried out using F2-B2 and GAPDH primers. The PCR products were then separated on a 2% agarose gel.

FACS analysis of cell surface expression of receptors. Forty-eight hours post-transduction, HeLa cells were collected in enzyme-free cell dissociation buffer (Invitrogen, CA), washed once with PBS containing 0.5% BSA and let stand in the same buffer for 10 minutes at 4° C. PE-conjugated anti-DR4 (DJR1 clone), anti-DR5 (DJR2-4 clone), anti-DcR1 (DJR3 clone), anti-DcR2 (DJR4-1 clone), anti-TRAIL (clone RIK 2) and anti-FasL (NOK1) antibodies purchased from eBiosciences, San Diego, Calif. and anti-Fas (BD Pharmingen) were used for staining samples for 30 minutes at 4° C. A mouse IgG antibody was used as isotype control. Cells were washed with PBS and GFP-positive cells were analyzed by using a FACS Calibur (Becton Dickinson, N.J.).

Suppression of apoptosis using DN-FADD and CrmA. HeLa and PA-1 cells were transfected with either DN-FADD, CrmA or control PCDNA 3.1 vector using Super-Fect reagent (Qiagen Inc., CA). Permanently transfected cells were selected in 800 µg/mL of G418. Post-selection, stably transfected cells were grown in medium containing 400 µg/mL of G418. The stable cells were transduced with the respective lentiviruses and 72 h post-transduction, cells were assayed for spontaneous apoptosis. Cells were treated with 10 ng of TRAIL 36 h post-transduction and assayed for apoptosis by active-caspase-3 staining.

Active-caspase-3 detection by FACS. Active-caspase-3 levels were detected by analyzing PE-positive population using the active-caspase-3-PE staining kit (BD Pharmingen, San Diego, Calif.). Only GFP-positive cells were included in the analysis using a FACS Calibur.

Characterization of DISC immunoprecipitated using anti-DR4/DR5 antibody. HeLa cells ($2 \times 10^7$) and PA-1 cells ($5 \times 10^7$) transduced for 48 h were collected and washed in cold PBS. Washed cells were lysed in 1 mL of lysis buffer [30 mM Tris/HCl, pH 7.5, 150mM NaCl, 2 mM EDTA, 1 mM phenylmethylsulfonyl fluoride (PMSF), protease inhibitors cocktail (Roche, Mannheim, Germany), 1% Triton X-100 and 10% glycerol] on ice for 30 minutes and clarified by centrifugation at 12000 rpm for 30 minutes at 4° C. Supernatants were normalized for protein concentration and then immunoprecipitated using 2 µg of H-130 DR4/DR5 antibody on a rotoshaker at 4° C. for 4 h followed by addition of 25 µL of 50% slurry of Protein A/G (Amersham, Piscataway, N.J.) beads for 2 hours. The beads were then washed three times with lysis buffer and boiled in SDS lysis buffer (62.5 mM Tris-HCl, 2% SDS, 10% glycerol, 50mM DTT and bromophenol blue, pH 6.8) for 5 minutes. Eluates were then subjected to SDS-PAGE using a 12% gel for subsequent immunoblot analysis.

Characterization of DISC immunoprecipitated using anti-TRAIL antibody. HeLa ($2 \times 10^7$) cells transduced for 36 h were treated with 250 ng of TRAIL (Peprotech) for 30 minutes either at 4° C. (untreated) or at 37° C. (treated), collected, washed in cold PBS and lysed in 1 mL lysis buffer for 30 minutes on ice. The lysates were clarified and then normalized for protein concentration. The DISC was then immunoprecipitated overnight using 2 µg/mL of anti-TRAIL-biotinylated antibody. The biotinylated antibody was immunoprecipitated with 35 µL of 50% slurry of streptavidin agarose beads. The beads were washed three times with lysis buffer, boiled in SDS sample buffer and separated on a 12% SDS-PAGE gel for immunoblot analysis.

Immunoprecipitation of the MADD complex. HeLa cells were transfected with MADD-YFP. Thirty-six hours post-transduction HeLa ($2 \times 10^7$) cells were collected and left untreated or treated with 250 ng/mL TRAIL for 30 minutes at 37° C. At the end of the treatment, cells were washed in cold PBS and pelletted and then lysed in 1 mL of DISC lysis buffer for 30 minutes on ice and clarified by centrifugation. The supernatants were normalized for protein concentration, precleared and were incubated with 10 µL of polyclonal anti-IG20 antibodies on a rotoshaker overnight. The complexes were immunoprecipitated with 50% slurry of protein A/G beads. The beads were washed three times and boiled in SDS lysis buffer for 5 minutes. The eluates were then subjected to SDS-PAGE using a 12% gel for immunoblot analysis.

Immunoblotting. The membranes were blocked in 5% non-fat dry milk in PBS-Tween (PBS with 0.05% Tween 20) for 1 hour. Primary antibodies were used at a concentration of 1 µg/mL and the secondary antibodies were used at a 1:10000 concentration. The blots were developed by enhanced chemiluminescence according to the manufacturer's protocol (Pierce Biotechnology Inc., Rockford, Ill.).

Cell culture and viability assay. HEK293, HeLa and PA-1 cells were cultured. Cell death was determined by Trypan Blue exclusion and the numbers of Trypan Blue-positive and -negative cells were counted using a haemocytometer.

Constructions of MADD Mutants. The serine residues or threonine residues at the consensus Akt phosphorylation sites of MADD were mutated to the alanine residue using QuikChange II XL Site-Directed Mutagenesis Kit (Stratagene) according to the manufacturer's instructions. All constructs were sequenced to ensure that only the desired mutations had been introduced.

Virus Infection and Transfection of Cells. Construction of lentiviruses containing different ShRNAs and virus infection of target cells for MADD knockdown are described elsewhere. The cells were transfected using an Effectene Transfection Kit (Qiagen).

Phosphorylation of MADD In Vitro. Kinase assay was performed using standard procedures. In brief, 2 µg purified GST-tagged wtMADD or MADD mutants were incubated for 1 h at 30° C. with 0.2 µg rAkt, 5 µCi γATP in a kinase buffer. The reaction products were fractionated by SDS-PAGE and $^{32}$P-labelled proteins were visualized by autoradiography. Loaded GST-MADD was visualized by probing the same membrane with an anti-MADD antibody.

Metabolic Labeling. HEK293 cells were washed twice with phosphate-free DMEM supplemented with 10% dialyzed FBS and subsequently incubated with 0.3 mCi/ml [$^{32}$P] orthophosphate in the same medium for 6 h. MADD was immunoprecipitated with an anti-MADD antibody. The precipitated MADD was separated by SDS-PAGE, transferred to a nitrocellulose membrane and subjected to autoradiography. Loaded MADD was visualized by immunoblotting the same membrane using an anti-MADD antibody.

Immunoblot Analysis. Cells were lysed for 1 h at 4° C. in a lysis buffer (20 mM Tris pH 7.5, 2 mM EDTA, 3 mM EGTA, 2 mM dithiothreitol (DTT), 250 mM sucrose, 0.1 mM phenylmethylsulfonyl fluoride, 1% Triton X-100) containing a protease inhibitor cocktail (Sigma, St. Louis, Mo.). Equal protein loading was controlled by Ponceau Red staining of membranes. Blots were probed using corresponding primary antibodies followed by horseradish peroxidase-conjugated secondary antibodies, and the protein bands visualized by enhanced chemiluminescence.

Preparation of Subcellular Fractions. Mitochondrial fractions were prepared using standard procedures. Briefly, cells were washed twice with PBS and the pellet was suspended in 0.2 ml of buffer A (20 mM HEPES pH 7.5, 10 mM KCl, 1.5 mM MgCl$_2$, 1 mM EGTA, 1 mM EDTA, 1 mM DTT, 0.1 mM PMSF, 250 mM sucrose) containing a protease inhibitor cocktail. The cells were homogenized by 12 strokes in a Dounce homogenizer. The homogenates were centrifuged twice at 750 g for 5 min at 4° C. The supernatants were centrifuged at 10000 g for 15 min at 4° C. to collect mitochondria-enriched heavy membranes.

Plasma Membrane Preparations. Plasma membrane and cytosolic fractions were prepared using standard procedures. Cells were washed in ice cold buffer (160 mM NaCl, 38 mM HEPES, pH 7.4, 1 mM MgCl$_2$, 1 mM EGTA) containing protease inhibitor cocktail (Rosch). Cells were lysed by sonication (on setting 5 at 20V) with three pulses of 15 s with 15 s pauses on ice. An aliquot of total cell lysate was removed for western blotting control and the rest was subjected to low speed centrifugation at 400×g, for 10 min at 4° C., to remove unbroken cells, debris, and nuclei. Further the lysate was separated by ultracentrifugation at 117,000×g, 60 min at 4° C. into cytosol and membrane fraction. Membrane pellets were resuspended in 2× Laemlei sample buffer and boiled for 5 min. All samples were frozen at −80° C. Samples were analyzed by western blot and probed with anti-pMADD antibody. Equal loading for membrane and cytosolic fractions were monitored by re-probing the membrane with Caveolin-1 and β-actin, respectively. (Barber M A., et al. JBC, 2007 Oct. 12; 282(41):29967-76).

Immunoprecipitation. Immunoprecipitations were performed using standard procedures. The samples were precleared with 10% (vol/vol) Protein-A agarose (Roche) for 1 h on a rocking platform. Specific antibodies were added and rocked for 1 h. Immunoprecipitates were captured by incubating with 10% (vol/vol) Protein-A agarose for an hour. The agarose beads were spun down and washed three times with NET/NP40 buffer (150 mM NaCl, 2 mM EDTA, 50 mM Tris-HCl pH 7.5, 0.1% NP-40). The antigens were released and denatured by adding SDS sample buffer. Immunoblots were prepared and analysed as described above.

Generation of Anti-Phospho-S70, -T173 and -T1041 Antibodies. The anti-phospho-antibodies were produced by Eurogentec Deutschland GmbH. Cäcilienstrasse 46. 50667 Köln. GERMANY. The phosphopeptides, CRQRRMpSL-RDDTS (SEQ ID NO: 7) (S-70), GSRSRNSpTLTSL (SEQ ID NO: 8) (T-173), and KRKRSPpTESVNTP (SEQ ID NO: 9) (T-1041) were used to immunize the rabbits. The antisera were depleted of antibodies that recognize nonphosphorylated MADD.

Cell Death ELISA and Caspase-8 Activity Assay. Histone-associated DNA fragments were analyzed by a Cell death ELISA Kit (Roche). Caspase-8 activity was detected using the assay kit (R&D System). The assay procedures were followed according to the kit instructions.

Statistical Analysis. Paired data were evaluated by Student's t-test. A 1-way ANOVA was used for multiple comparisons. A value of $p<0.05$ was considered significant.

Sequences

An shRNA sequence for "mid" siRNA is GTACCAGCT-TCAGTCTTTCTTCAAGAGA GAAAGACTGAAGCTG-GTAC (SEQ ID NO: 16), with the hairpin loop region highlighted in bold.

An shRNA sequence for "13L" siRNA is CGGCGAATC-TATGACAATCTTCAAGAGA GATTGTCATAGAT-TCGCCG (SEQ ID NO: 17), with the hairpin loop region highlighted in bold.

Antisense molecules against Iab are used in treatments. Sense molecules of Iab are used to restore lost Iab function in diseased normal cells, for example, gland cells.

The cDNA sequence of MADD splice variant is as follows (SEQ ID NO: 1):

```
cacgtgcatg tgtagcatgc cttggttttt cctttggcat ctgaaaaagg cacaacctga aagacctaga acccagtgtc ggtccccagg cccttttggga caggaagaga agagccgtgt ggccgcgggg aggatgtcct gcggcggggc tgtcctcgcg gactgactgg actccatctc ccagcgggcg ccgcggcgcg gccacgcccc cccactcccc gcgcgcgccc ggtggagact tcgattttca gaattcctcc tgggaatgct gactccttgc ttggtgccct gatgcttctc tgagataaac tgatgaattg gaaccatggt gcaaaagaag aagttctgtc ctcggttact tgactatcta gtgatcgtag gggccaggca cccgagcagt gatagcgtgg cccagactcc tgaattgcta cggcgatacc ccttggagga tcacactgag tttcccctgc ccccagatgt agtgttcttc tgccagcccg agggctgcct gagcgtgcgg cagcgcgca tgagccttcg ggatgatacc tcttttgtct tcaccctcac tgacaaggac actggagtca cgcgatatgg catctgtgtt aacttctacc gctccttcca aaagcgaatc tctaaggaga aggggggaagg tggggcaggg tcccgtggga
```

-continued

```
aggaaggaac ccatgccacc tgtgcctcag aagagggtgg
cactgagagc tcagagagtg gctcatccct gcagcctctc
agtgctgact ctaccoctga tgtgaaccag tctcctcggg
gcaaacgccg ggccaaggcg gggagccgct cccgcaacag
tactctcacg tccctgtgcg tgctcagcca ctacccttc
ttctccacct tccgagagtg tttgtatact ctcaagcgcc
tggtggactg ctgtagtgag cgccttctgg gcaagaaact
gggcatccct cgaggcgtac aaagggacac catgtggcgg
atctttactg gatcgctgct ggtagaggag aagtcaagtg
cccttctgca tgaccttcga gagattgagg cctggatcta
tcgattgctg cgctccccag tacccgtctc tgggcagaag
cgagtagaca tcgaggtcct accccaagag ctccagccag
ctctgacctt tgctcttcca gacccatctc gattcaccct
agtggattt ccactgcacc ttccctttgga acttctaggt
gtggacgcct gtctccaggt gctaacctgc attctgttag
agcacaaggt ggtgctacag tcccgagact acaatgcact
ctccatgtct gtgatggcat tcgtggcaat gatctaccca
ctggaatata tgtttcctgt catcccgctg ctaccacct
gcatggcatc agcagagcag ctgctgttgg ctccaacccc
gtacatcatt ggggttcctg ccagcttctt cctctacaaa
ctggacttca aaatgcctga tgatgtatgg ctagtggatc
tggacagcaa tagggtgatt gcccccacca atgcagaagt
gctgcctatc ctgccagaac cagaatcact agagctgaaa
aagcatttaa agcaggcctt ggccagcatg agtctcaaca
cccagcccat cctcaatctg agaaatttc atgagggcca
ggagatcccc cttctcttgg gaaggccttc taatgacctg
cagtccacac cgtccactga attcaaccca ctcatctatg
gcaatgatgt ggattctgtg gatgttgcaa ccagggttgc
catggtacgg ttcttcaatt ccgccaacgt gctgcaggga
tttcagatgc acacgcgtac cctgcgcctc tttcctcggc
ctgtggtagc ttttcaagct ggctcctttc tagcctcacg
tccccggcag actccttttg ccgagaaatt ggccaggact
caggctgtgg agtactttgg ggaataaatc cttaacccca
ccaactatgc ctttcagcga attcacaaca atatgtttga
tccagccctg attggtgaca agccaaagtg gtatgctcat
cagctgcagc ctatccacta tcgcgtctat gacagcaatt
cccagctggc tgaggcctg agtgtaccac cagagcggga
ctctgactcc gaacctactg atgatagtgg cagtgatagt
atggattatg acgattcaag ctcttcttac tcctcccttg
gtgactttgt cagtgaaatg atgaaatgtg acattaatgg
```

```
tgatactccc aatgtggacc ctctgacaca tgcagcactg
ggaaatacca gcgaggtgga gattgacgag ctgcagaatc
agaaggaagc agaagagcct ggcccagaca gtgagaactc
tcaggaaaac cccccactgc gctccagctc tagcaccaca
gccagcagca gccccagcac tgtcatccac ggagccaact
ctgaacctgc tgactctacg gagatggatg ataaggcagc
agtaggcgtc tccaagcccc tcccttccgt gcctcccagc
attggcaaat cgaacatgga cagacgtcag gcagaaattg
gagagggtc agtgcgccgg cgaatctatg acaatccata
cttcgagccc caatatggct ttcccctga ggaagatgag
gatgagcagg gggaaagtta cactccccga ttcagccaac
atgtcagtgg caatcgggct caaaagctgc tgcggcccaa
cagcttgaga ctggcaagtg actcagatgc agagtcagac
tctcgggcaa gctctcccaa ctccaccgtc tccaacacca
gcaccgaggg cttcgggggc atcatgtctt tgccagcag
cctctatcgg aaccacagta ccagcttcag tctttcaaac
ctcacactgc ccaccaaagg tgcccgagag aaggccacgc
ccttccccag tctgaaagga acaggaggg cgttagtgga
tcagaagtca tctgtcatta aacacagccc aacagtgaaa
agagaacctc catcacccca gggtcgatcc agcaattcta
gtgagaacca gcagttcctg aaggaggtgg tgcacagcgt
gctggacggc cagggagttg gctggctcaa catgaaaaag
gtgcgccggc tgctggagag cgagcagctg cgagtctttg
tcctgagcaa gctgaaccgc atggtgcagt cagaggacga
tgcccggcag acatcatcc ggatgtgga gatcagtcgg
aaggtgtaca agggaatgtt agacctcctc aagtgtacag
tcctcagctt ggagcagtcc tatgcccacg cgggtctggg
tggcatggcc agcatctttg ggcttttgga gattgccag
acccactact atagtaaaga accagacaag cggaagagaa
gtccaacaga aagtgtaaat accccagttg gcaaggatcc
tggcctagct gggcggggggg acccaaaggc tatggcacaa
ctgagagttc cacaactggg acctcgggca ccaagtgcca
caggaaaggg tcctaaggaa ctggacacca gaagtttaaa
ggaagaaaat tttatagcat ctattgggcc tgaagtaatc
aaacctgtct ttgaccttgg tgagacagag gagaaaaagt
cccagatcag cgcagacagt ggtgtgagcc tgacgtctag
ttcccagagg actgatcaag actctgtcat cggcgtaagt
ccagctgtta tgatccgcag ctcaagtcag gattctgaag
ttagcaccgt ggtgagtaat agctctggag agacccttgg
agctgacagt gacttgagca gcaatgcagg tgatggacca
ggtggcgagg gcagtgttca cctggcaagc tctcggggca
```

-continued

```
ctttgtctga tagtgaaatt gagaccaact ctgccacaag
caccatcttt ggtaaagccc acagcttgaa gccaagcata
aaggagaagc tggcaggcag ccccattcgt acttctgaag
atgtgagcca gcgagtctat ctctatgagg gactcctagg
caaagagcgt tctactttat gggaccaaat gcaattctgg
gaagatgcct tcttagatgc tgtgatgttg gagagagaag
ggatgggtat ggaccagggt ccccaggaaa tgatcgacag
gtacctgtcc cttggagaac atgaccggaa gcgcctggaa
gatgatgaag atcgcttgct ggccacactt ctgcacaacc
tcatctccta catgctgctg atgaaggtaa ataagaatga
catccgcaag aaggtgaggc gcctaatggg aaagtcgcac
attgggcttg tgtacagcca gcaaatcaat gaggtgcttg
atcagctggc gaacctgaat ggacgcgatc tctctatctg
gtccagtggc agccggcaca tgaagaagca gacatttgtg
gtacatgcag ggacagatac aaacggagat atcttttca
tggaggtgtg cgatgactgt gtggtgttgc gtagtaacat
cggaacagtg tatgagcgct ggtggtacga gaagctcatc
aacatgacct actgtcccaa gacgaaggtg ttgtgcttgt
ggcgtagaaa tggctctgag acccagctca acaagttcta
tactaaaaag tgtcgggagc tgtactactg tgtgaaggac
agcatggagc gcgctgccgc ccgacagcaa agcatcaaac
ccggacctga attgggtggc gagttccctg tgcaggacct
gaagactggt gagggtggcc tgctgcaggt gaccctggaa
gggatcaacc tcaaattcat gcacaatcag gttttcatag
agctgaatca cattaaaaag tgcaatacag ttcgaggcgt
ctttgtcctg gaggaatttg ttcctgaaat taaagaagtg
gtgagccaca agtacaagac accaatggcc cacgaaatct
gctactccgt attatgtctc ttctcgtacg tggctgcagt
tcatagcagt gaggaagatc tcagaacccc gccccggcct
gtctctagct gatggagagg ggctacgcag ctgccccagc
ccagggcacg cccctggccc cttgctgttc ccaagtgcac
gatgctgctg tgactgagga gtggatgatg ctcgtgtgtc
ctctgcaagc cccctgctgt ggcttggttg gttaccggtt
atgtgtccct ctgagtgtgt cttgagcgtg tccaccttct
ccctctccac tcccagaaga ccaaactgcc ttcccctcag
ggctcaagaa tgtgtacagt ctgtggggcc ggtgtgaacc
cactattttg tgtccttgag acatttgtgt tgtggttcct
tgtccttgtc cctggcgtta taactgtcca ctgcaagagt
ctggctctcc cttctctgtg acccggcatg actgggcgcc
tggagcagtt tcactctgtg aggagtgagg gaaccctggg
gctcacccctc tcagaggaag ggcacagaga ggaagggaag
aattgggggg cagccggagt gagtggcagc ctccctgctt
ccttctgcat tcccaagccg gcagctactg cccagggccc
gcagtgttgg ctgctgcctg ccacagcctc tgtgactgca
gtggagcggc gaattccctg tggcctgcca cgccttcggc
atcagaggat ggagtggtcg aggctagtgg agtcccaggg
accgctggct gctctgcctg agcatcaggg aggggcagg
aaagaccaag ctgggtttgc acatctgtct gcaggctgtc
tctccaggca cggggtgtca ggagggagag acagcctggg
tatgggcaag aaatgactgt aaatatttca gccccacatt
atttatagaa aatgtacagt tgtgtgaatg tgaaataaat
gtcctcaact ccc
```

In the MADD cDNA sequence presented above, the highlighted portion in bold indicates nucleotides that are absent in a variation of the MADD splice variant, whose sequence is provided below (SEQ ID NO: 2):

```
atggtgcaaaagaagaagttctgtcctcggttacttgactatctagtgat
cgtaggggccaggcacccgagcagtgatagcgtggcccagactcctgaat
tgctacggcgatacccttggaggatcacactgagtttcccctgcccca
gatgtagtgttcttctgccagcccgagggctgcctgagcgtgcggcagcg
gcgcatgagccttcgggatgatacctcttttgtcttcaccctcactgaca
aggacactggagtcacgcgatatggcatctgtgttaacttctaccgctcc
ttccaaaagcgaatctctaaggagaaggggggaaggtggggcagggtcccg
tgggaaggaaggaacccatgccacctgtgcctcagaagagggtggcactg
agagctcagagagtggctcatccctgcagcctctcagtgctgactctacc
cctgatgtgaaccagtctcctcggggcaaacgccgggccaaggcgggag
ccgctcccgcaacagtactctcacgtccctgtgcgtgctcagccactacc
ctttcttctccaccttccgagagtgtttgtatactctcaagcgcctggtg
gactgctgtagtgagcgccttctgggcaagaaactgggcatccctcgagg
cgtacaaagggacaccatgtggcggatctttactggatcgctgctggtag
aggagaagtcaagtgcccttctgcatgaccttcgagagattgaggcctgg
atctatcgattgctgcgctccccagtacccgtctctgggcagaagcgagt
agacatcgaggtcctaccccaagagctccagccagctctgacctttgctc
ttccagacccatctcgattcaccctagtggatttcccactgcaccttccc
ttggaacttctaggtgtggacgcctgtctccaggtgctaacctgcattct
gttagagcacaaggtggtgctacagtcccgagactacaatgcactctcca
tgtctgtgatggcattcgtggcaatgatctacccactggaatatatgttt
cctgtcatcccgctgctacccacctgcatggcatcagcagagcagctgct
gttggctccaaccccgtacatcattgggttcctgccagcttcttcctct
acaaactggacttcaaaatgcctgatgatgtatggctagtggatctggac
agcaatagggtgattgcccccaccaatgcagaagtgctgcctatcctgcc
```

-continued

```
agaaccagaatcactagagctgaaaaagcatttaaagcaggccttggcca
gcatgagtctcaacacccagcccatcctcaatctggagaaatttcatgag
ggccaggagatccccttctcttgggaaggccttctaatgacctgcagtc
cacaccgtccactgaattcaacccactcatctatggcaatgatgtggatt
ctgtggatgttgcaaccaggggttgccatggtacggttcttcaattccgcc
aacgtgctgcagggatttcagatgcacacgcgtaccctgcgcctctttcc
tcggcctgtggtagcttttcaagctggctcctttctagcctcacgtcccc
ggcagactccttttgccgagaaattggccaggactcaggctgtggagtac
tttggggaatggatccttaaccccaccaactatgcctttcagcgaattca
caacaatatgtttgatccagccctgattggtgacaagccaaagtggtatg
ctcatcagctgcagcctatccactatcgcgtctatgacagcaattcccag
ctggctgaggccctgagtgtaccaccagagcgggactctgactccgaacc
tactgatgatagtggcagtgatagtatggattatgacgattcaagctctt
cttactcctcccttggtgactttgtcagtgaaatgatgaaatgtgacatt
aatggtgatactcccaatgtggaccctctgacacatgcagcactggggga
tgccagcgaggtggagattgacgagctgcagaatcagaaggaagcagaag
agcctggcccagacagtgagaactctcaggaaaaccccccactgcgctcc
agctctagcaccacagccagcagcagcccagcactgtcatccacggagc
caactctgaacctgctgactctacggagatggatgataaggcagcagtag
gcgtctccaagcccctcccttccgtgcctcccagcattggcaaatcgaac
atggacagacgtcaggcagaaattggagaggggtcagtgcgccggcgaat
ctatgacaatccatacttcgagccccaatatggctttccccctgaggaag
atgaggatgagcaggggaaagttacactcccgattcagccaacatgtc
agtggcaatcgggctcaaaagctgctgcggcccaacagcttgagactggc
aagtgactcagatgcagagtcagactctcgggcaagctctcccaactcca
ccgtctccaacaccagcaccgagggcttcgggggcatcatgtcttttgcc
agcagcctctatcggaaccacagtaccagcttcagtctttcaaacctcac
actgcccaccaaaggtgcccgagagaaggccacgcccttccccagtctga
aaggaaacaggagggcgttagtggatcagaagtcatctgtcattaaacac
agcccaacagtgaaaagagaacctccatcaccccagggtcgatccagcaa
ttctagtgagaaccagcagttcctgaaggaggtggtgcacagcgtgctgg
acggccagggagttggctggctcaacatgaaaaaggtgcgccggctgctg
gagagcgagcagctgcgagtctttgtcctgagcaagctgaaccgcatggt
gcagtcagaggacgatgcccggcaggacatcatcccggatgtggagatca
gtcggaaggtgtacaagggaatgttagacctcctcaagtgtacagtcctc
agcttggagcagtccatgcccacgcgggtctgggtggcatggccagcat
ctttgggcttttggagattgcccagacccactactatagtaaagaaccag
acaagcggaagagaagtccaacagaaagtgtaaataccccagttggcaag
gatcctggcctagctgggcgggggggacccaaaggctatggcacaactgag
agttccacaactgggaccctcgggcaccaagtgccacaggaaagggtccta
aggaactggacaccagaagtttaaaggaagaaaattttatagcatctatt
gggcctgaagtaatcaaacctgtcttgaccttggtgagacagaggagaa
aaagtcccagatcagcgcagacagtggtgtgagcctgacgtctagttccc
agaggactgatcaagactctgtcatcggcgtgagtccagctgttatgatc
cgcagctcaagtcaggattctgaagtgagtaatagctctggagagaccct
tggagctgacagtgacttgagcagcaatgcaggtgatggaccaggtggcg
agggcagtgttcacctggcaagctctcggggcactttgtctgatagtgaa
attgagaccaactctgccacaagcaccatctttggtaaagcccacagctt
gaagccaagcataaaggagaagctggcaggcagcccccattcgtacttctg
aagatgtgagccagcgagtctatctctatgagggactcctaggcaaagag
cgttctactttatgggaccaaatgcaattctgggaagatgccttcttaga
tgctgtgatgttggagagagaagggatgggtatggaccagggtccccagg
aaatgatcgacaggtacctgtcccttggagaacatgaccggaagcgcctg
gaagatgatgaagatcgcttgctggccacacttctgcacaacctcatctc
ctacatgctgctgatgaaggtaaataagaatgacatccgcaagaaggtga
ggcgcctaatgggaaagtcgcacattgggcttgtgtacagccagcaaatc
aatgaggtgcttgatcagctggcgaacctgaatggacgcgatctctctat
ctggtccagtggcagccggcacatgaagaagcagacatttgtggtacatg
cagggacagatacaaacggagatatctttttcatggaggtgtgcgatgac
tgtgtggtgttgcgtagtaacatcggaacagtgtatgagcgctggtggta
cgagaagctcatcaacatgacctactgtcccaagacgaaggtgttgtgct
tgtggcgtagaaatggctctgagacccagctcaacaagttctatactaaa
aagtgtcgggagctgtactactgtgtgaaggacagcatggagcgcgctgc
cgcccgacagcaaagcatcaaacccggacctgaattgggtggcgagttcc
ctgtgcaggacctgaagactggtgagggtggcctgctgcaggtgaccctg
gaagggatcaacctcaaattcatgcacaatcaggtttttcatagagctgaa
tcacattaaaaagtgcaatacagttcgaggcgtctttgtcctggaggaat
ttgttcctgaaattaaagaagtggtgagccacaagtacaagacaccaatg
gcccacgaaatctgctactccgtatatgtctcttctcgtacgtggctgc
agttcatagcagtgaggaagatctcagaaccccgccccggcctgtctcta
gctga
```

The amino acid sequence of MADD is as follows (SEQ ID NO: 3):

```
MVQKKKFCPRLLDYLVIVGARHPSSDSVAQTPELLRRYPLEDHTEFPLPP
DVVFFCQPEGCLSVRQRRMSLRDDTSFVFTLTDKDTGVTRYGICVNFYRS
FQKRISKEKGEGGAGSRGKEGTHATCASEEGGTESSESGSSLQPLSADST
PDVNQSPRGKRRAKAGSRSRNSTLTSLCVLSHYPFFSTFRECLYTLKRLV
DCCSERLLGKKLGIPRGVQRDTMWRIFTGSLLVEEKSSALLHDLREIEAW
IYRLLRSPVPVSGQKRVDIEVLPQELQPALTFALPDPSRFTLVDFPLHLP
LELLGVDACLQVLTCILLEHKVVLQSRDYNALSMSVMAFVAMIYPLEYMF
```

PVIPLLPTCMASAEQLLLAPTPYIIGVPASFFLYKLDFKMPDDVWLVDLD
SNRVIAPTNAEVLPILPEPESLELKKHLKQALASMSLNTQPILNLEKFHE
GQEIPLLLGRPSNDLQSTPSTEFNPLIYGNDVDSVDVATRVAMVRFFNSA
NVLQGFQMHTRTLRLFPRPVVAFQAGSFLASRPRQTPFAEKLARTQAVEY
FGEWILNPTNYAFQRIHNNMFDPALIGDKPKWYAHQLQPIHYRVYDSNSQ
LAEALSVPPERDSDSEPTDDSGSDSMDYDDSSSSYSSLGDFVSEMMKCDI
NGDTPNVDPLTHAALGDASEVEIDELQNQKEAEEPGPDSENSQENPPLRS
SSSTTASSSPSTVIHGANSEPADSTEMDDKAAVGVSKPLPSVPPSIGKSN
MDRRQAEIGEGSVRRRIYDNPYFEPQYGFPPEEDEDEQGESYTPRFSQHV
SGNRAQKLLRPNSLRLASDSDAESDSRASSPNSTVSNTSTEGFGGIMSFA
SSLYRNHSTSFSLSNLTLPTKGAREKATPFPSLKGNRRALVDQKSSVIKH
SPTVKREPPSPQGRSSNSSENQQFLKEVVHSVLDGQGVGWLNMKKVRRLL
ESEQLRVFVLSKLNRMVQSEDDARQDIIPDVEISRKVYKGMLDLLKCTVL

SLEQSYAHAGLGGMASIFGLLEIAQTHYYSKEPDKRKRSPTESVNTPVGK
DPGLAGRGDPKAMAQLRVPQLGPRAPSATGKGPKELDTRSLKEENFIASI
GPEVIKPVFDLGETEEKKSQISADSGVSLTSSSQRTDQDSVIGVSPAVMI
RSSSQDSEVSTVVSNSSGETLGADSDLSSNAGDGPGGEGSVHLASSRGTL
SDSEIETNSATSTIFGKAHSLKPSIKEKLAGSPIRTSEDVSQRVYLYEGL
LGKERSTLWDQMQFWEDAFLDAVMLEREGMGMDQGPQEMIDRYLSLGEHD
RKRLEDDEDRLLATLLHNLISYMLLMKVNKNDIRKKVRRLMGKSHIGLVY
SQQINEVLDQLANLNGRDLSIWSSGSRHMKKQTFVVHAGTDTNGDIFFME
VCDDCVVLRSNIGTVYERWWYEKLINMTYCPKTKVLCLWRRNGSETQLNK
FYTKKCRELYYCVKDSMERAAARQQSIKPGPELGGEFPVQDLKTGEGGLL
QVTLEGINLKFMHNQVFIELNHIKKCNTVRGVFVLEEFVPEIKEVVSHKY
KTPMAHEICYSVLCLFSYVAAVHSSEEDLRTPPRPVSS.

The invention claimed is:

1. An isolated siRNA nucleic acid that selectively down-regulates the expression of at least one splice variant of an IG20 (Insulinoma-Glucagonoma) gene, wherein the splice variant is MADD represented by the cDNA sequence of SEQ ID NO: 1, and wherein not all isoforms of IG20 are knocked down.

2. The nucleic acid of claim 1, wherein the nucleic acid encodes a short interfering RNA, the nucleic acid comprising the structure:

$X_{sense}$—hairpin loop—$X_{anti\text{-}sense}$ wherein X comprises a nucleic acid sequence CGGC-GAATCTATGACAATC (SEQ ID NO: 4).

3. The nucleic acid of claim 2, wherein the nucleic acid sequence is CGGCGAATCTATGACAATCTTCAA-GAGAGATTGTCATAGATTCGCCG (SEQ ID NO: 5), wherein the hairpin loop region is from positions 20-28 of the sequence.

4. The nucleic acid of claim 1 is synthetic.

5. The nucleic acid of claim 1 encoding an RNA molecule comprising nucleic acid sequence CGGCGAAUCUAUGA-CAAUC (SEQ ID NO: 6).

6. A pharmaceutical composition consisting essentially of the nucleic acid of claim 1 capable of selectively inhibiting the expression of a MADD splice variant in a cancer cell.

7. The pharmaceutical composition of claim 6, wherein the nucleic acid sequence comprises CGGCGAATCTATGA-CAATC (SEQ ID NO: 4).

8. The nucleic acid of claim 1, wherein the siRNA molecule is expressed from a shRNA vector.

9. The nucleic acid of claim 1, wherein the nucleic acid molecule targets exon 13L of the MADD splice variant.

* * * * *

UNITED STATES PATENT AND TRADEMARK OFFICE
CERTIFICATE OF CORRECTION

PATENT NO. : 7,910,723 B2  
APPLICATION NO. : 12/174296  
DATED : March 22, 2011  
INVENTOR(S) : Prabhakar et al.

Page 1 of 1

It is certified that error appears in the above-identified patent and that said Letters Patent is hereby corrected as shown below:

On the title page, Column 1, the paragraph beginning at line 16 should read as follows:

--This invention was made with government support under grant number CA107506 awarded by the National Institutes of Health. The government has certain rights in the invention.--

Signed and Sealed this  
Tenth Day of May, 2011

David J. Kappos  
*Director of the United States Patent and Trademark Office*

```
                       SEQUENCE LISTING

<160> NUMBER OF SEQ ID NOS: 17

<210> SEQ ID NO 1
<211> LENGTH: 5973
<212> TYPE: DNA
<213> ORGANISM: Homo sapiens

<400> SEQUENCE: 1
cacgtgcatg tgtagcatgc cttggttttt cctttggcat ctgaaaaagg cacaacctga      60
aagacctaga acccagtgtc ggtccccagg cccctttgga caggaagaga agagccgtgt     120
ggccgcgggg aggatgtcct gcggcgggc tgtcctcgcg gactgactgg actccatctc     180
ccagcgggcg ccgcggcgcg gccacgcccc cccactcccc gcgcgcgccc ggtggagact     240
tcgattttca gaattcctcc tgggaatgct gactccttgc ttggtgccct gatgcttctc     300
tgagataaac tgatgaattg gaaccatggt gcaaagaag aagttctgtc ctcggttact     360
tgactatcta gtgatcgtag gggccaggca cccgagcagt gatagcgtgg cccagactcc     420
tgaattgcta cggcgatacc ccttgaggga tcacactgag tttcccctgc ccccagatgt     480
agtgttcttc tgccagcccg agggctgcct gagcgtgcgc cagcggcgca tgagccttcg     540
ggatgatacc tcttttgtct tcaccctcac tgacaaggac actggagtca cgcgatatgg     600
catctgtgtt aacttctacc gctccttcca aaagcgaatc tctaaggaga agggggaagg     660
tggggcaggg tcccgtggga aggaaggaac ccatgccacc tgtgcctcag aagagggtgg     720
cactgagagc tcagagagtg gctcatccct gcagcctctc agtgctgact ctaccccctga     780 tgtgaaccag tctcctcggg gcaaacgccg ggccaaggcg ggagccgct cccgcaacag     840 tactctcacg tccctgtgcg tgctcagcca ctacccttc ttctccacct tccgagagtg     900
tttgtatact ctcaagcgcc tggtggactg ctgtagtgag cgccttctgg gcaagaaact     960
gggcatccct cgaggcgtac aaagggacac catgtggcgg atctttactg gatcgctgct    1020
ggtagaggag aagtcaagtg cccttctgca tgaccttcga gagattgagg cctggatcta    1080
tcgattgctg cgctccccag tacccgtctc tgggcagaag cgagtagaca tcgaggtcct    1140
accccaagag ctccagccag ctctgacctt tgctcttcca gacccatctc gattcaccct    1200
```

```
agtggatttc ccactgcacc ttcccttgga acttctaggt gtggacgcct gtctccaggt   1260
gctaacctgc attctgttag agcacaaggt ggtgctacag tcccgagact acaatgcact   1320
ctccatgtct gtgatggcat tcgtggcaat gatctaccca ctggaatata tgtttcctgt   1380
catcccgctg ctacccacct gcatggcatc agcagagcag ctgctgttgg ctccaacccc   1440
gtacatcatt gggggttcctg ccagcttctt cctctacaaa ctggacttca aaatgcctga   1500
tgatgtatgg ctagtggatc tggacagcaa tagggtgatt gcccccacca atgcagaagt   1560
gctgcctatc ctgccagaac cagaatcact agagctgaaa aagcatttaa agcaggcctt   1620
ggccagcatg agtctcaaca cccagcccat cctcaatctg agaaatttc atgagggcca   1680
ggagatcccc cttctcttgg aaggccttc taatgacctg cagtccacac cgtccactga   1740
attcaaccca ctcatctatg caatgatgt ggattctgtg gatgttgcaa ccagggttgc   1800
catggtacgg ttcttcaatt ccgccaacgt gctgcaggga tttcagatgc acacgcgtac   1860
cctgcgcctc tttcctcggc ctgtggtagc ttttcaagct ggctcctttc tagcctcacg   1920
tccccggcag actcctttg ccagaaaatt ggccaggact caggctgtgg agtactttgg   1980
ggaatggatc cttaaccca ccaactatgc cttcagcga attcacaaca atatgtttga   2040
tccagccctg attggtgaca agccaaagtg gtatgctcat cagctgcagc ctatccacta   2100
tcgcgtctat gacagcaatt cccagctggc tgaggccctg agtgtaccac cagagcggga   2160
ctctgactcc gaacctactg atgatagtgg cagtgatagt atggattatg acgattcaag   2220
ctcttcttac tcctcccttg gtgactttgt cagtgaaatg atgaaatgtg acattaatgg   2280
tgatactccc aatgtggacc ctctgacaca tgcagcactg ggggatgcca gcgaggtgga   2340
gattgacgag ctgcagaatc agaaggaagc agaagagcct ggcccagaca gtgagaactc   2400
tcaggaaaac cccccactgc gctccagctc tagcaccaca gccagcagca gccccagcac   2460
tgtcatccac ggagccaact ctgaacctgc tgactctacg gagatggatg ataaggcagc   2520
agtaggcgtc tccaagcccc tccctcctcgt gcctcccagc attggcaaat cgaacatgga   2580
cagacgtcag gcagaaattg gagaggggtc agtgcgccgg cgaatctatg acaatccata   2640
cttcgagccc caatatggct ttccccctga ggaagatgag gatgagcagg gggaaagtta   2700
cactccccga ttcagccaac atgtcagtgg caatcgggct caaaagctgc tgcggcccaa   2760
cagcttgaga ctggcaagtg actcagatgc agagtcagac tctcgggcaa gctctcccaa   2820
ctccaccgtc tccaacacca gcaccgaggg cttcggggc atcatgtctt ttgccagcag   2880
cctctatcgg aaccacagta ccagcttcag tctttcaaac ctcacactgc ccaccaaagg   2940
tgcccgagag aaggccacgc ccttcccag tctgaaagga aacaggaggg cgttagtgga   3000
tcagaagtca tctgtcatta aacacagccc aacagtgaaa agagaacctc catcaccca   3060
gggtcgatcc agcaattcta gtgagaacca gcagttcctg aaggaggtgg tgcacagcgt   3120
gctggacggc cagggagttg gctggctcaa catgaaaaag gtgcgccggc tgctggagag   3180
cgagcagctg cgagtctttg tcctgagcaa gctgaaccgc atggtgcagt cagaggacga   3240
tgcccggcag gacatcatcc cggatgtgga gatcagtcgg aaggtgtaca agggaatgtt   3300
agacctcctc aagtgtacag tcctcagctt ggagcagtcc tatgcccacg cgggtctggg   3360
tggcatggcc agcatctttg ggcttttgga gattgcccag acccactact atagtaaaga   3420
accagacaag cggaagagaa gtccaacaga aagtgtaaat accccagttg caaggatcc   3480
tggcctagct gggcgggggg acccaaaggc tatggcacaa ctgagagttc acaactggg   3540
acctcgggca ccaagtgcca caggaaaggg tcctaaggaa ctggacacca gagtttaaa   3600
```

```
ggaagaaaat tttatagcat ctattgggcc tgaagtaatc aaacctgtct ttgaccttgg   3660
tgagacagag gagaaaaagt cccagatcag cgcagacagt ggtgtgagcc tgacgtctag   3720
ttcccagagg actgatcaag actctgtcat cggcgtgagt ccagctgtta tgatccgcag   3780
ctcaagtcag gattctgaag ttagcaccgt ggtgagtaat agctctggag agacccttgg   3840
agctgacagt gacttgagca gcaatgcagg tgatggacca ggtggcgagg gcagtgttca   3900
cctggcaagc tctcggggca ctttgtctga tagtgaaatt gagaccaact ctgccacaag   3960
caccatcttt ggtaaagccc acagcttgaa gccaagcata aaggagaagc tggcaggcag   4020
ccccattcgt acttctgaag atgtgagcca gcgagtctat ctctatgagg gactcctagg   4080
caaagagcgt tctactttat gggaccaaat gcaattctgg gaagatgcct tcttagatgc   4140
tgtgatgttg gagagagaag ggatgggtat ggaccagggt cccaggaaaa tgatcgacag   4200
gtacctgtcc cttggagaac atgaccggaa gcgcctggaa gatgatgaag atcgcttgct   4260
ggccacactt ctgcacaacc tcatctccta catgctgctg atgaaggtaa ataagaatga   4320
catccgcaag aaggtgaggc gcctaatggg aaagtcgcac attgggcttg tgtacagcca   4380
gcaaatcaat gaggtgcttg atcagctggc gaacctgaat ggacgcgatc tctctatctg   4440
gtccagtggc agccggcaca tgaagaagca gacatttgtg gtacatgcag ggacagatac   4500
aaacggagat atcttttca tggaggtgtg cgatgactgt gtggtgttgc gtagtaacat   4560
cggaacagtg tatgagcgct ggtggtacga gaagctcatc aacatgacct actgtcccaa   4620
gacgaaggtg ttgtgcttgt ggcgtagaaa tggctctgag acccagctca acaagttcta   4680
tactaaaaag tgtcgggagc tgtactactg tgtgaaggac agcatggagc gcgctgccgc   4740
ccgacagcaa agcatcaaac ccggacctga attgggtggc gagttccctg tgcaggacct   4800
gaagactggt gagggtggcc tgctgcaggt gaccctggaa gggatcaacc tcaaattcat   4860
gcacaatcag gttttcatag agctgaatca cattaaaaag tgcaatacag ttcgaggcgt   4920
cttgtcctg gaggaatttg ttcctgaaat taaagaagtg gtgagccaca agtacaagac   4980
accaatggcc cacgaaatct gctactccgt attatgtctc ttctcgtacg tggctgcagt   5040
tcatagcagt gaggaagatc tcagaacccc gccccggcct gtctctagct gatggagagg   5100
ggctacgcag ctgccccagc ccagggcacg cccctggccc cttgctgttc caagtgcac   5160
gatgctgctg tgactgagga gtggatgatg ctcgtgtgtc ctctgcaagc cccctgctgt   5220
ggcttggttg gttaccggtt atgtgtccct ctgagtgtgt cttgagcgtg tccaccttct   5280
ccctctccac tcccagaaga ccaaactgcc ttcccctcag ggctcaagaa tgtgtacagt   5340
ctgtggggcc ggtgtgaacc cactattttg tgtccttgag acatttgtgt tgtggttcct   5400
tgtccttgtc cctggcgtta taactgtcca ctgcaagagt ctggctctcc cttctctgtg   5460
acccggcatg actgggcgcc tggagcagtt tcactctgtg aggagtgagg gaaccctggg   5520
gctcaccctc tcagaggaag gcacagaga ggaagggaag aattgggggg cagccggagt   5580
gagtggcagc ctccctgctt ccttctgcat tcccaagccg gcagctactg cccagggccc   5640
gcagtgttgg ctgctgcctg ccacagcctc tgtgactgca gtggagcggc gaattccctg   5700
tggcctgcca cgccttcggc atcagaggat ggagtggtcg aggctagtgg agtcccaggg   5760
accgctggct gctctgcctg agcatcaggg agggggcagg aaagaccaag ctgggttgc    5820
acatctgtct gcaggctgtc tctccaggca cggggtgtca ggaggagag acagcctggg    5880
tatgggcaag aaatgactgt aaatatttca gccccacatt atttatagaa aatgtacagt   5940
tgtgtgaatg tgaaataaat gtcctcaact ccc                                5973
```

<210> SEQ ID NO 2
<211> LENGTH: 4755
<212> TYPE: DNA
<213> ORGANISM: Homo sapiens

<400> SEQUENCE: 2

| | | | | | |
|---|---|---|---|---|---|
| atggtgcaaa | agaagaagtt | ctgtcctcgg | ttacttgact | atctagtgat | cgtaggggcc | 60 |
| aggcacccga | gcagtgatag | cgtggcccag | actcctgaat | tgctacggcg | ataccccttg | 120 |
| gaggatcaca | ctgagtttcc | cctgccccca | gatgtagtgt | tcttctgcca | gcccgagggc | 180 |
| tgcctgagcg | tgcggcagcg | cgcatgagc | cttcggatg | atacctcttt | tgtcttcacc | 240 |
| ctcactgaca | aggacactgg | agtcacgcga | tatggcatct | gtgttaactt | ctaccgctcc | 300 |
| ttccaaaagc | gaatctctaa | ggagaagggg | gaaggtgggg | cagggtcccg | tgggaaggaa | 360 |
| ggaacccatg | ccacctgtgc | ctcagaagag | ggtggcactg | agagctcaga | gagtggctca | 420 |
| tccctgcagc | ctctcagtgc | tgactctacc | cctgatgtga | accagtctcc | tcggggcaaa | 480 |
| cgccgggcca | aggcggggag | ccgctcccgc | aacagtactc | tcacgtccct | gtgcgtgctc | 540 |
| agccactacc | ctttcttctc | caccttccga | gagtgtttgt | atactctcaa | cgcctggtg | 600 |
| gactgctgta | gtgagcgcct | tctgggcaag | aaactgggca | tccctcgagg | cgtacaaagg | 660 |
| gacaccatgt | ggcggatctt | tactggatcg | ctgctggtag | aggagaagtc | aagtgccctt | 720 |
| ctgcatgacc | ttcgagagat | tgaggcctgg | atctatcgat | tgctgcgctc | cccagtaccc | 780 |
| gtctctgggc | agaagcgagt | agacatcgag | gtcctacccc | aagagctcca | gccagctctg | 840 |
| acctttgctc | ttccagaccc | atctcgattc | accctagtgg | atttcccact | gcaccttccc | 900 |
| ttggaacttc | taggtgtgga | cgcctgtctc | caggtgctaa | cctgcattct | gttagagcac | 960 |
| aaggtggtgc | tacagtcccg | agactacaat | gcactctcca | tgtctgtgat | ggcattcgtg | 1020 |
| gcaatgatct | acccactgga | atatatgttt | cctgtcatcc | cgctgctacc | cacctgcatg | 1080 |
| gcatcagcag | agcagctgct | gttggctcca | accccgtaca | tcattggggt | tcctgccagc | 1140 |
| ttcttcctct | acaaactgga | cttcaaaatg | cctgatgatg | tatggctagt | ggatctggac | 1200 |
| agcaataggg | tgattgcccc | caccaatgca | gaagtgctgc | ctatcctgcc | agaaccagaa | 1260 |
| tcactagagc | tgaaaaagca | tttaaagcag | gccttggcca | gcatgagtct | caacacccag | 1320 |
| cccatcctca | atctggagaa | atttcatgag | ggccaggaga | tcccccttct | cttgggaagg | 1380 |
| ccttctaatg | acctgcagtc | cacaccgtcc | actgaattca | cccactcat | ctatggcaat | 1440 |
| gatgtggatt | ctgtggatgt | tgcaaccagg | gttgccatgg | tacggttctt | caattccgcc | 1500 |
| aacgtgctgc | agggatttca | gatgcacacg | cgtaccctgc | gcctctttcc | tcggcctgtg | 1560 |
| gtagcttttc | aagctggctc | ctttctagcc | tcacgtcccc | ggcagactcc | ttttgccgag | 1620 |
| aaattggcca | ggactcaggc | tgtggagtac | tttggggaat | ggatccttaa | ccccaccaac | 1680 |
| tatgcctttc | agcgaattca | caacaatatg | tttgatccag | ccctgattgg | tgacaagcca | 1740 |
| aagtggtatg | ctcatcagct | gcagcctatc | cactatcgcg | tctatgacag | caattcccag | 1800 |
| ctggctgagg | ccctgagtgt | accaccagag | cgggactctg | actccgaacc | tactgatgat | 1860 |
| agtggcagtg | atagtatgga | ttatgacgat | tcaagctctt | cttactcctc | ccttggtgac | 1920 |
| tttgtcagtg | aaatgatgaa | atgtgacatt | aatggtgata | ctcccaatgt | ggaccctctg | 1980 |
| acacatgcag | cactggggga | tgccagcgag | gtggagattg | acgagctgca | gaatcagaag | 2040 |
| gaagcagaag | agcctggccc | agacagtgag | aactctcagg | aaaaccccc | actgcgctcc | 2100 |
| agctctagca | ccacagccag | cagcagcccc | agcactgtca | tccacggagc | caactctgaa | 2160 |

```
cctgctgact ctacggagat ggatgataag gcagcagtag gcgtctccaa gcccctccct    2220
tccgtgcctc ccagcattgg caaatcgaac atggacagac gtcaggcaga aattggagag    2280
gggtcagtgc gccggcgaat ctatgacaat ccatacttcg agccccaata tggctttccc    2340
cctgaggaag atgaggatga gcaggggggaa agttacactc cccgattcag ccaacatgtc    2400
agtggcaatc gggctcaaaa gctgctgcgg cccaacagct tgagactggc aagtgactca    2460
gatgcagagt cagactctcg ggcaagctct cccaactcca ccgtctccaa caccagcacc    2520
gagggcttcg ggggcatcat gtcttttgcc agcagcctct atcggaacca cagtaccagc    2580
ttcagtcttt caaacctcac actgcccacc aaaggtgccc gagagaaggc cacgcccttc    2640
cccagtctga aggaaacag gagggcgtta gtggatcaga agtcatctgt cattaaacac    2700
agcccaacag tgaaaagaga acctccatca ccccagggtc gatccagcaa ttctagtgag    2760
aaccagcagt tcctgaagga ggtggtgcac agcgtgctgg acggccaggg agttggctgg    2820
ctcaacatga aaaaggtgcg ccggctgctg gagagcgagc agctgcgagt cttttgtcctg   2880 agcaagctga accgcatggt gcagtcagag gacgatgccc ggcaggacat catcccggat    2940
gtggagatca gtcggaaggt gtacaaggga atgttagacc tcctcaagtg tacagtcctc    3000
agcttggagc agtcctatgc ccacgcgggt ctgggtggca tggccagcat ctttgggctt    3060
ttggagattg cccagaccca ctactatagt aagaaccag acaagcggaa gagaagtcca    3120
acagaaagtg taaatacccc agttggcaag gatcctggcc tagctgggcg ggggggaccca   3180 aaggctatgg cacaactgag agttccacaa ctgggacctc gggcaccaag tgccacagga    3240
aagggtccta aggaactgga caccagaagt ttaaaggaag aaaattttat agcatctatt    3300
gggcctgaag taatcaaacc tgtctttgac cttggtgaga cagaggagaa aaagtcccag    3360
atcagcgcag acagtggtgt gagcctgacg tctagttccc agaggactga tcaagactct    3420
gtcatcggcg tgagtccagc tgttatgatc cgcagctcaa gtcaggattc tgaagtgagt    3480
aatagctctg gagagaccct tggagctgac agtgacttga gcagcaatgc aggtgatgga    3540
ccaggtggcg agggcagtgt tcacctggca agctctcggg gcactttgtc tgatagtgaa    3600
attgagacca actctgccac aagcaccatc tttggtaaag cccacagctt gaagccaagc    3660
ataaaggaga agctggcagg cagccccatt cgtacttctg aagatgtgag ccagcgagtc    3720
tatctctatg agggactcct aggcaaagag cgttctactt tatgggacca aatgcaattc    3780
tgggaagatg ccttcttaga tgctgtgatg ttggagagag aagggatggg tatgaccag    3840 ggtccccagg aaatgatcga caggtacctg tcccttggag aacatgaccg gaagcgcctg    3900
gaagatgatg aagatcgctt gctggccaca cttctgcaca acctcatctc ctacatgctg    3960
ctgatgaagg taaataagaa tgacatccgc aagaaggtga ggcgcctaat gggaaagtcg    4020
cacattgggc ttgtgtacag ccagcaaatc aatgaggtgc ttgatcagct ggcgaacctg    4080
aatggacgcg atctctctat ctggtccagt ggcagccggc acatgaagaa gcagacattt    4140
gtggtacatg cagggacaga tacaaacgga gatatctttt tcatggaggt gtgcgatgac    4200
tgtgtggtgt tgcgtagtaa catcggaaca gtgtatgagc gctggtggta cgagaagctc    4260
atcaacatga cctactgtcc caagacgaag gtgttgtgct tgtggcgtag aaatggctct    4320
gagacccagc tcaacaagtt ctatactaaa agtgtcgggg agctgtacta ctgtgtgaag    4380
gacagcatgg agcgcgctgc cgcccgacag caaagcatca accccggacc tgaattgggt    4440
ggcgagttcc ctgtgcagga cctgaagact ggtgagggtg gcctgctgca ggtgaccctg    4500
gaagggatca acctcaaatt catgcacaat caggtttttca tagagctgaa tcacattaaa    4560
```

```
aagtgcaata cagttcgagg cgtctttgtc ctggaggaat ttgttcctga aattaaagaa    4620
gtggtgagcc acaagtacaa gacaccaatg gcccacgaaa tctgctactc cgtattatgt    4680
ctcttctcgt acgtggctgc agttcatagc agtgaggaag atctcagaac cccgccccgg    4740
cctgtctcta gctga                                                     4755
```

<210> SEQ ID NO 3
<211> LENGTH: 1588
<212> TYPE: PRT
<213> ORGANISM: Homo sapiens

<400> SEQUENCE: 3

```
Met Val Gln Lys Lys Phe Cys Pro Arg Leu Leu Asp Tyr Leu Val
1               5                   10                  15

Ile Val Gly Ala Arg His Pro Ser Ser Asp Ser Val Ala Gln Thr Pro
                20                  25                  30

Glu Leu Leu Arg Arg Tyr Pro Leu Glu Asp His Thr Glu Phe Pro Leu
        35                  40                  45

Pro Pro Asp Val Val Phe Phe Cys Gln Pro Glu Gly Cys Leu Ser Val
    50                  55                  60

Arg Gln Arg Arg Met Ser Leu Arg Asp Asp Thr Ser Phe Val Phe Thr
65              70                  75                  80

Leu Thr Asp Lys Asp Thr Gly Val Thr Arg Tyr Gly Ile Cys Val Asn
                85                  90                  95

Phe Tyr Arg Ser Phe Gln Lys Arg Ile Ser Lys Glu Lys Gly Glu Gly
                100                 105                 110

Gly Ala Gly Ser Arg Gly Lys Glu Gly Thr His Ala Thr Cys Ala Ser
            115                 120                 125

Glu Glu Gly Gly Thr Glu Ser Ser Glu Ser Gly Ser Ser Leu Gln Pro
        130                 135                 140

Leu Ser Ala Asp Ser Thr Pro Asp Val Asn Gln Ser Pro Arg Gly Lys
145                 150                 155                 160

Arg Arg Ala Lys Ala Gly Ser Arg Ser Arg Asn Ser Thr Leu Thr Ser
                165                 170                 175

Leu Cys Val Leu Ser His Tyr Pro Phe Phe Ser Thr Phe Arg Glu Cys
                180                 185                 190

Leu Tyr Thr Leu Lys Arg Leu Val Asp Cys Cys Ser Glu Arg Leu Leu
            195                 200                 205

Gly Lys Lys Leu Gly Ile Pro Arg Gly Val Gln Arg Asp Thr Met Trp
        210                 215                 220

Arg Ile Phe Thr Gly Ser Leu Leu Val Glu Glu Lys Ser Ser Ala Leu
225                 230                 235                 240

Leu His Asp Leu Arg Glu Ile Glu Ala Trp Ile Tyr Arg Leu Leu Arg
                245                 250                 255

Ser Pro Val Pro Val Ser Gly Gln Lys Arg Val Asp Ile Glu Val Leu
                260                 265                 270

Pro Gln Glu Leu Gln Pro Ala Leu Thr Phe Ala Leu Pro Asp Pro Ser
            275                 280                 285

Arg Phe Thr Leu Val Asp Phe Pro Leu His Leu Pro Leu Glu Leu Leu
        290                 295                 300

Gly Val Asp Ala Cys Leu Gln Val Leu Thr Cys Ile Leu Leu Glu His
305                 310                 315                 320

Lys Val Val Leu Gln Ser Arg Asp Tyr Asn Ala Leu Ser Met Ser Val
                325                 330                 335
```

-continued

Met Ala Phe Val Ala Met Ile Tyr Pro Leu Glu Tyr Met Phe Pro Val
            340                 345                 350

Ile Pro Leu Leu Pro Thr Cys Met Ala Ser Ala Glu Gln Leu Leu Leu
            355                 360                 365

Ala Pro Thr Pro Tyr Ile Ile Gly Val Pro Ala Ser Phe Phe Leu Tyr
            370                 375                 380

Lys Leu Asp Phe Lys Met Pro Asp Asp Val Trp Leu Asp Val Asp Leu Asp
385                 390                 395                 400

Ser Asn Arg Val Ile Ala Pro Thr Asn Ala Glu Val Leu Pro Ile Leu
                405                 410                 415

Pro Glu Pro Glu Ser Leu Glu Leu Lys Lys His Leu Lys Gln Ala Leu
            420                 425                 430

Ala Ser Met Ser Leu Asn Thr Gln Pro Ile Leu Asn Leu Glu Lys Phe
            435                 440                 445

His Glu Gly Gln Glu Ile Pro Leu Leu Leu Gly Arg Pro Ser Asn Asp
            450                 455                 460

Leu Gln Ser Thr Pro Ser Thr Glu Phe Asn Pro Leu Ile Tyr Gly Asn
465                 470                 475                 480

Asp Val Asp Ser Val Asp Val Ala Thr Arg Val Ala Met Val Arg Phe
                485                 490                 495

Phe Asn Ser Ala Asn Val Leu Gln Gly Phe Gln Met His Thr Arg Thr
            500                 505                 510

Leu Arg Leu Phe Pro Arg Pro Val Val Ala Phe Gln Ala Gly Ser Phe
            515                 520                 525

Leu Ala Ser Arg Pro Arg Gln Thr Pro Phe Ala Glu Lys Leu Ala Arg
            530                 535                 540

Thr Gln Ala Val Glu Tyr Phe Gly Glu Trp Ile Leu Asn Pro Thr Asn
545                 550                 555                 560

Tyr Ala Phe Gln Arg Ile His Asn Asn Met Phe Asp Pro Ala Leu Ile
                565                 570                 575

Gly Asp Lys Pro Lys Trp Tyr Ala His Gln Leu Gln Pro Ile His Tyr
            580                 585                 590

Arg Val Tyr Asp Ser Asn Ser Gln Leu Ala Glu Ala Leu Ser Val Pro
            595                 600                 605

Pro Glu Arg Asp Ser Asp Ser Glu Pro Thr Asp Asp Ser Gly Ser Asp
            610                 615                 620

Ser Met Asp Tyr Asp Asp Ser Ser Ser Tyr Ser Ser Leu Gly Asp
625                 630                 635                 640

Phe Val Ser Glu Met Met Lys Cys Asp Ile Asn Gly Asp Thr Pro Asn
                645                 650                 655

Val Asp Pro Leu Thr His Ala Ala Leu Gly Asp Ala Ser Glu Val Glu
            660                 665                 670

Ile Asp Glu Leu Gln Asn Gln Lys Glu Ala Glu Pro Gly Pro Asp
            675                 680                 685

Ser Glu Asn Ser Gln Glu Asn Pro Pro Leu Arg Ser Ser Ser Ser Thr
            690                 695                 700

Thr Ala Ser Ser Ser Pro Ser Thr Val Ile His Gly Ala Asn Ser Glu
705                 710                 715                 720

Pro Ala Asp Ser Thr Glu Met Asp Asp Lys Ala Ala Val Gly Val Ser
                725                 730                 735

Lys Pro Leu Pro Ser Val Pro Pro Ser Ile Gly Lys Ser Asn Met Asp
            740                 745                 750

Arg Arg Gln Ala Glu Ile Gly Glu Gly Ser Val Arg Arg Ile Tyr
            755                 760                 765

-continued

Asp Asn Pro Tyr Phe Glu Pro Gln Tyr Gly Phe Pro Pro Glu Glu Asp
770             775             780

Glu Asp Glu Gln Gly Glu Ser Tyr Thr Pro Arg Phe Ser Gln His Val
785             790             795             800

Ser Gly Asn Arg Ala Gln Lys Leu Leu Arg Pro Asn Ser Leu Arg Leu
                805             810             815

Ala Ser Asp Ser Asp Ala Glu Ser Asp Ser Arg Ala Ser Ser Pro Asn
                820             825             830

Ser Thr Val Ser Asn Thr Ser Thr Glu Gly Phe Gly Gly Ile Met Ser
        835             840             845

Phe Ala Ser Ser Leu Tyr Arg Asn His Ser Thr Ser Phe Ser Leu Ser
850             855             860

Asn Leu Thr Leu Pro Thr Lys Gly Ala Arg Glu Lys Ala Thr Pro Phe
865             870             875             880

Pro Ser Leu Lys Gly Asn Arg Arg Ala Leu Val Asp Gln Lys Ser Ser
                885             890             895

Val Ile Lys His Ser Pro Thr Val Lys Arg Glu Pro Pro Ser Pro Gln
                900             905             910

Gly Arg Ser Ser Asn Ser Ser Glu Asn Gln Gln Phe Leu Lys Glu Val
        915             920             925

Val His Ser Val Leu Asp Gly Gln Gly Val Gly Trp Leu Asn Met Lys
930             935             940

Lys Val Arg Arg Leu Leu Glu Ser Glu Gln Leu Arg Val Phe Val Leu
945             950             955             960

Ser Lys Leu Asn Arg Met Val Gln Ser Glu Asp Ala Arg Gln Asp
                965             970             975

Ile Ile Pro Asp Val Glu Ile Ser Arg Lys Val Tyr Lys Gly Met Leu
        980             985             990

Asp Leu Leu Lys Cys Thr Val Leu  Ser Leu Glu Gln Ser  Tyr Ala His
        995             1000             1005

Ala Gly  Leu Gly Gly Met Ala  Ser Ile Phe Gly Leu  Leu Glu Ile
    1010             1015             1020

Ala Gln  Thr His Tyr Tyr Ser  Lys Glu Pro Asp Lys  Arg Lys Arg
    1025             1030             1035

Ser Pro  Thr Glu Ser Val Asn  Thr Pro Val Gly Lys  Asp Pro Gly
    1040             1045             1050

Leu Ala  Gly Arg Gly Asp Pro  Lys Ala Met Ala Gln  Leu Arg Val
    1055             1060             1065

Pro Gln  Leu Gly Pro Arg Ala  Pro Ser Ala Thr Gly  Lys Gly Pro
    1070             1075             1080

Lys Glu  Leu Asp Thr Arg Ser  Leu Lys Glu Glu Asn  Phe Ile Ala
    1085             1090             1095

Ser Ile  Gly Pro Glu Val Ile  Lys Pro Val Phe Asp  Leu Gly Glu
    1100             1105             1110

Thr Glu  Glu Lys Lys Ser Gln  Ile Ser Ala Asp Ser  Gly Val Ser
    1115             1120             1125

Leu Thr  Ser Ser Ser Gln Arg  Thr Asp Gln Asp Ser  Val Ile Gly
    1130             1135             1140

Val Ser  Pro Ala Val Met Ile  Arg Ser Ser Gln Asp  Ser Glu
    1145             1150             1155

Val Ser  Thr Val Val Ser Asn  Ser Ser Gly Glu Thr  Leu Gly Ala
    1160             1165             1170

Asp Ser  Asp Leu Ser Ser Asn  Ala Gly Asp Gly Pro  Gly Gly Glu

```
                1175                1180                1185
Gly Ser Val His Leu Ala Ser Ser Arg Gly Thr Leu Ser Asp Ser
        1190                1195                1200
Glu Ile Glu Thr Asn Ser Ala Thr Ser Thr Ile Phe Gly Lys Ala
        1205                1210                1215
His Ser Leu Lys Pro Ser Ile Lys Glu Lys Leu Ala Gly Ser Pro
        1220                1225                1230
Ile Arg Thr Ser Glu Asp Val Ser Gln Arg Val Tyr Leu Tyr Glu
        1235                1240                1245
Gly Leu Leu Gly Lys Glu Arg Ser Thr Leu Trp Asp Gln Met Gln
        1250                1255                1260
Phe Trp Glu Asp Ala Phe Leu Asp Ala Val Met Leu Glu Arg Glu
        1265                1270                1275
Gly Met Gly Met Asp Gln Gly Pro Gln Glu Met Ile Asp Arg Tyr
        1280                1285                1290
Leu Ser Leu Gly Glu His Asp Arg Lys Arg Leu Glu Asp Asp Glu
        1295                1300                1305
Asp Arg Leu Leu Ala Thr Leu Leu His Asn Leu Ile Ser Tyr Met
        1310                1315                1320
Leu Leu Met Lys Val Asn Lys Asn Asp Ile Arg Lys Lys Val Arg
        1325                1330                1335
Arg Leu Met Gly Lys Ser His Ile Gly Leu Val Tyr Ser Gln Gln
        1340                1345                1350
Ile Asn Glu Val Leu Asp Gln Leu Ala Asn Leu Asn Gly Arg Asp
        1355                1360                1365
Leu Ser Ile Trp Ser Ser Gly Ser Arg His Met Lys Lys Gln Thr
        1370                1375                1380
Phe Val Val His Ala Gly Thr Asp Thr Asn Gly Asp Ile Phe Phe
        1385                1390                1395
Met Glu Val Cys Asp Asp Cys Val Val Leu Arg Ser Asn Ile Gly
        1400                1405                1410
Thr Val Tyr Glu Arg Trp Trp Tyr Glu Lys Leu Ile Asn Met Thr
        1415                1420                1425
Tyr Cys Pro Lys Thr Lys Val Leu Cys Leu Trp Arg Arg Asn Gly
        1430                1435                1440
Ser Glu Thr Gln Leu Asn Lys Phe Tyr Thr Lys Lys Cys Arg Glu
        1445                1450                1455
Leu Tyr Tyr Cys Val Lys Asp Ser Met Glu Arg Ala Ala Ala Arg
        1460                1465                1470
Gln Gln Ser Ile Lys Pro Gly Pro Glu Leu Gly Gly Glu Phe Pro
        1475                1480                1485
Val Gln Asp Leu Lys Thr Gly Glu Gly Gly Leu Leu Gln Val Thr
        1490                1495                1500
Leu Glu Gly Ile Asn Leu Lys Phe Met His Asn Gln Val Phe Ile
        1505                1510                1515
Glu Leu Asn His Ile Lys Lys Cys Asn Thr Val Arg Gly Val Phe
        1520                1525                1530
Val Leu Glu Glu Phe Val Pro Glu Ile Lys Glu Val Val Ser His
        1535                1540                1545
Lys Tyr Lys Thr Pro Met Ala His Glu Ile Cys Tyr Ser Val Leu
        1550                1555                1560
Cys Leu Phe Ser Tyr Val Ala Ala Val His Ser Ser Glu Glu Asp
        1565                1570                1575
```

```
Leu Arg  Thr Pro Pro Arg Pro  Val Ser Ser
    1580              1585
```

```
<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cggcgaatct atgacaatc                                                    19

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cggcgaatct atgacaatct tcaagagaga ttgtcataga ttcgccg                     47

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cggcgaaucu augacaauc                                                    19

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated-Met

<400> SEQUENCE: 7

Cys Arg Gln Arg Arg Met Ser Leu Arg Asp Asp Thr Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated-Ser

<400> SEQUENCE: 8

Gly Ser Arg Ser Arg Asn Ser Thr Leu Thr Ser Leu
1               5                   10

<210> SEQ ID NO 9
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated-Pro

<400> SEQUENCE: 9

Lys Arg Lys Arg Ser Pro Thr Glu Ser Val Asn Thr Pro
1               5                   10

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtaccagctt cagtctttc                                                  19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctctaatgga gattgttac                                                  19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttaaccgtt taccggcct                                                  19

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggaaccaca gtacaagctt tagcctctca aacctcacac tgcc                      44

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcagtgtga ggtttgagag gctaaagctt gtactgtggt tccg                      44
```

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgccggcgaa tctatgacaa t                                              21

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtaccagctt cagtctttct tcaagagaga aagactgaag ctggtac                  47

<210> SEQ ID NO 17
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggcgaatct atgacaatct tcaagagaga ttgtcataga ttcgccg                  47
```